(12) United States Patent
Coulter et al.

(10) Patent No.: US 9,980,902 B2
(45) Date of Patent: *May 29, 2018

(54) METHOD FOR TREATING INTESTINAL FIBROSIS

(71) Applicant: Sigmoid Pharma Limited, Dublin (IE)

(72) Inventors: Ivan Coulter, Dublin (IE); Vincenzo Aversa, Dublin (IE)

(73) Assignee: Sigmoid Pharma Limited, Dublin (IE)

( * ) Notice: Subject to any disclaimer, the term of this patent is extended or adjusted under 35 U.S.C. 154(b) by 22 days.

This patent is subject to a terminal disclaimer.

(21) Appl. No.: 15/090,377

(22) Filed: Apr. 4, 2016

(65) Prior Publication Data

US 2016/0213611 A1      Jul. 28, 2016

Related U.S. Application Data

(63) Continuation of application No. 14/185,786, filed on Feb. 20, 2014, now Pat. No. 9,320,746.

(Continued)

(30) Foreign Application Priority Data

Mar. 14, 2013   (GB) .................................. 1304662.8

(51) Int. Cl.
   *A61K 31/58*   (2006.01)
   *A61K 9/16*    (2006.01)
   (Continued)

(52) U.S. Cl.
   CPC .............. *A61K 9/0053* (2013.01); *A61K 9/16* (2013.01); *A61K 9/1611* (2013.01); *A61K 9/1617* (2013.01); *A61K 9/1623* (2013.01); *A61K 9/1641* (2013.01); *A61K 9/1652* (2013.01); *A61K 9/1658* (2013.01); *A61K 9/1694* (2013.01); *A61K 9/4808* (2013.01); *A61K 9/4891* (2013.01); *A61K 9/50* (2013.01); *A61K 9/5036* (2013.01); *A61K 9/5042* (2013.01);
   (Continued)

(58) Field of Classification Search
   CPC ..................................................... A61K 31/58
   See application file for complete search history.

(56) References Cited

U.S. PATENT DOCUMENTS

| | | |
|---|---|---|
| 5,645,856 A | 7/1997 | Lacy et al. |
| 5,858,401 A | 1/1999 | Bhalani et al. |

(Continued)

FOREIGN PATENT DOCUMENTS

| | | |
|---|---|---|
| AU | 31116/77 | 11/1977 |
| CA | 2376261 | 12/2000 |

(Continued)

OTHER PUBLICATIONS

The European Agency for the Evaluation of Medicinal Products, Committee for Veterinary Medicinal Products, "Polyethylene Glycol Stearates and Polyethylene Glycol 15 Hydroxystearate," Jun. 2003, 3 pages.

(Continued)

*Primary Examiner* — Benjamin Packard
(74) *Attorney, Agent, or Firm* — Klarquist Sparkman, LLP

(57) ABSTRACT

A method for treating intestinal fibrosis in a subject, comprising enterally administering a steroid to the subject. The steroid may be in a multiple minibead formulation.

34 Claims, 8 Drawing Sheets

Related U.S. Application Data

(60) Provisional application No. 61/767,632, filed on Feb. 21, 2013.

(51) Int. Cl.
  *A61K 9/00*     (2006.01)
  *A61K 31/502*    (2006.01)
  *A61K 38/13*    (2006.01)
  *A61K 31/223*    (2006.01)
  *A61K 31/56*    (2006.01)
  *A61K 9/50*     (2006.01)
  *A61K 9/48*     (2006.01)

(52) U.S. Cl.
  CPC .......... *A61K 31/223* (2013.01); *A61K 31/502* (2013.01); *A61K 31/56* (2013.01); *A61K 31/58* (2013.01); *A61K 38/13* (2013.01)

(56) References Cited

U.S. PATENT DOCUMENTS

| | | |
|---|---|---|
| 5,882,680 A | 3/1999 | Suzuki et al. |
| 5,958,876 A | 9/1999 | Woo et al. |
| 6,166,044 A | 12/2000 | Sandborn et al. |
| 6,190,692 B1 | 2/2001 | Busetti et al. |
| 6,267,985 B1 | 7/2001 | Chen et al. |
| 6,309,663 B1 | 10/2001 | Patel et al. |
| 6,451,339 B2 | 9/2002 | Patel et al. |
| 6,569,463 B2 | 5/2003 | Patel et al. |
| 6,585,997 B2 | 7/2003 | Moro et al. |
| 6,761,903 B2 | 7/2004 | Chen et al. |
| 6,923,988 B2 | 8/2005 | Patel et al. |
| 7,374,779 B2 | 5/2008 | Chen et al. |
| 7,727,551 B2 | 6/2010 | Massironi |
| 2001/0024658 A1 | 9/2001 | Chen et al. |
| 2003/0055028 A1 | 3/2003 | Stergiopoulos et al. |
| 2003/0104048 A1 | 6/2003 | Patel et al. |
| 2003/0180352 A1 | 9/2003 | Patel et al. |
| 2003/0235595 A1 | 12/2003 | Chen et al. |
| 2006/0034937 A1 | 2/2006 | Patel |
| 2008/0020018 A1 | 1/2008 | Moodley et al. |
| 2008/0113031 A1 | 5/2008 | Moodley et al. |
| 2008/0318912 A1 | 12/2008 | Fox et al. |
| 2009/0123390 A1* | 5/2009 | Hill ................. A61K 9/006 424/45 |
| 2010/0136105 A1 | 6/2010 | Chen et al. |
| 2010/0203120 A1 | 8/2010 | Coulter |
| 2010/0255087 A1 | 10/2010 | Coulter |
| 2012/0141531 A1 | 6/2012 | Coulter et al. |
| 2012/0258167 A1* | 10/2012 | Coulter ............... A61K 9/5015 424/452 |
| 2013/0243873 A1 | 9/2013 | Aversa et al. |

FOREIGN PATENT DOCUMENTS

| | | |
|---|---|---|
| EP | 0789561 | 8/1997 |
| GB | 2257359 | 1/1993 |
| JP | 07-247215 | 9/1995 |
| WO | WO 90/06775 | 6/1990 |
| WO | WO 97/02042 | 1/1997 |
| WO | WO 97/25980 | 7/1997 |
| WO | WO 01/32142 | 5/2001 |
| WO | WO 01/37808 | 5/2001 |
| WO | WO 03/018134 | 3/2003 |
| WO | WO 03/053404 | 7/2003 |
| WO | WO 03/068196 A1 | 8/2003 |
| WO | WO 2004/052339 A1 | 6/2004 |
| WO | WO 2006/002365 | 1/2006 |
| WO | WO 2006/035416 | 4/2006 |
| WO | WO 2006/110802 | 10/2006 |
| WO | WO 2007/012478 | 2/2007 |
| WO | WO 2007/018943 | 2/2007 |
| WO | WO 2008/046905 | 4/2008 |
| WO | WO 2011/088404 | 7/2011 |
| WO | WO 2011/151087 | 12/2011 |
| WO | WO 2012069658 A2 * | 5/2012 |

OTHER PUBLICATIONS

USP1547255 Polyoxyl 15 Hydroxystearate, https://www.lgcstandards.com/GB/en/Polyoxyl-15-Hydroxystearate/p/USP1547255/productPrintView, accessed Jan. 17, 2017, 2 pages.

Brooker et al., "Long-Acting Steroid Injection after Edoscopic Dilation of Anastomotic Crohn's Strictures May Improve the Outcome: A Retrospective Case Series," Endoscopy 35(4): 333-337, 2003.

Chourasia et al. "Pharmaceutical approaches to colon targeted drug delivery systems," *J. Pharm Pharmaceut Sci*, 6(1): 33-66, 2003.

Daum et al., "Therapy with Budesonide in Patietns with Refractory Sprue," *Digestion*, 73:60-68, 2006.

DeGuzman et al. "Endoscopic Treatment of Benign Extra-Esophageal Gastrointestinal Tract Strictures Via Combined Pneumatic Dilation and Interlesional Steroid Injection," *Gastrointestinal Endoscopy*, 43(4), 1996.

Fukata et al. "The effective therapy of cyclosporine A with drug delivery system in experimental colitis," *Journal of Drug Targeting*, 19(6): 458-467, 2011.

Gordon, Ilyssa O., "Fibrosis in Ulcerative Colitis: Mechanisms, Features, and Consequences of a Neglected Problem," *Inflamm Bowel Dis*, 20(11):2198-2206, Jun. 2, 2014.

Kjeldsen et al., "Seromarkers of collagen I and III metabolism in active Crohn's disease. Relation to disease activity and response to therapy," *Gut*, 37:805-810, 1995.

Lawrance, Ian, "Novel topical therapies for distal colitis," *World Journal of Gastrointestinal Pharmacology and Therapeutics*, 1(5): 87-93, Oct. 6, 2010.

Lee et al., "Preliminary experience with endoscopic intralesional steroid injection therapy for refractory upper gastrointestinal strictures," *Gastrointestinal Endoscopy*, 41(6), 1995.

Mastronardi et al. "Short onset of ulcerative colitis predicts the response to cyclosporine (Neoral) as bridge therapy in steroid-refractory ulcerative colitis," Poster presentations: Clinical: Therapy and observations, pp. S157-S158, 2013.

Navarro et al., "Treatment of Inflammatory Bowel Disease: Safety and Tolerability Issues," *The American Journal of Gastroenterology*, 98(12): S18-S23, 2003.

Office action issued for Japanese Patent Application No. 2006-507572.

Pochron et al., "A Prospective Randomized Controlled Trial of Endoscopic Steroid Injection Therapy for Recurrent Esophageal Peptic Strictures," *Gastrointestinal Endoscopy*, 59(5), 2004.

Pucilowska et al., "Fibrosis and inflammatory bowel disease: cellular mediators and animal models," *Am J Physiol Gastrointest Liver Physiol*, 279: G653-G659, 2000.

Qu, Zheng-Hai, "Inhibition airway remodeling and transforming growth factor β1/Smad signaling pathway by astragalus extract in asthmatic mice," *International Journal of Molecular Medicine*, 29: 564-568, 2012.

Rafii, Rokhsara, "A review of current and novel therapies for idiopathic pulmonary fibrosis," *J Thorac Dis*, 5(1): 48-73, Dec. 7, 2012.

Rieder et al., "Intestinal fibrosis in IBD—a dynamic, multifactorial process," *Nature Reviews: Gastroenterology & Hepatology*, 6:228-235, 2009.

Rieder et al., "Intestinal fibrosis in inflammatory bowel disease: progress in basic and clinical science," *Current Opinion in Gastroenterology*, 24(4): 462-468, Jul. 2008.

Rieder et al., "Wound Healing and Fibrosis in Intestinal Disease," *Gut*, 56:130-139, 2007.

Rodriguez et al., "Colonic budesonide delivery from ph-dependent microcapsules containing lipidic cores," *Acia Technologiae et Legis Medicamenti*, vol. XI, N. 1, 2000.

Rutgeerts et al., "A Comparison of Budesonide with Prednisolone for Active Crohn's Disease," *The New England Journal of Medicine*, 331(13): 842-845, Sep. 29, 1994.

(56) References Cited

OTHER PUBLICATIONS

Sharkey et al. "The use of Cyclosporin A in acute steroid-refractory ulcerative colitis: Long term outcomes," *Journal of Crohn's and Colitis*, 5: 91-94, 2011.
Shioji, Yusaku "Manufacturing technology of solid formulation", CMC Publishing Co. Ltd., pp. 46-48 and 174-177, Jan. 27, 2003.
Suzuki et al., "Analysis of intestinal fibrosis in chronic colitis in mice induced by dextran sulfate sodium," *Pathology International*, 61:228-238, 2011.
Suzuki et al., "Analysis of intestinal fibrosis in chronic colitis in mice induced by dextran sulfate sodium," *Pathology International*, 61: 228-238, 2011.
Van Deventer, "Small therapeutic molecules for the treatment of inflammatory bowel disease," *Gut*, 50(Suppl III):iii47-iii53, 2002.
Wakerly et al., "Pectin/Ethylcellulose Film Coating Formulations for Colonic Drug Delivery," Pharmaceutical Research, 13(8): 1210-1212, 1996.
Wen et al., "Inflammatory Bowel Disease: Autoimmune or Immune-meditated Pathogenesis?" *Clinical & Developmental Immunology*, 11(3/4): 195-204, Sep./Dec. 2004.

* cited by examiner

Healthy Control

DSS 2.5% No recovery 14 day recovery 14 day recovery with Budesonide

METHOD FOR TREATING INTESTINAL FIBROSIS

CROSS REFERENCE TO RELATED APPLICATIONS

This application is a continuation of U.S. application Ser. No. 14/185,786, filed Feb. 20, 2014, which claims the benefit of U.S. Provisional Application No. 61/767,632, filed Feb. 21, 2013, and Great Britain Application No. 1304662.8, filed Mar. 14, 2013, all of which are incorporated herein by reference in their entirety.

FIELD

This invention relates to pharmaceutical compositions useful for medical purposes relating to fibrosis of the gastrointestinal tract. The invention also relates to methods of making the compositions, methods of using them, and other subject matter.

BACKGROUND

Tissue in a living creature is continually repairing and regenerating. Normally this repair and regeneration occurs naturally without any adverse effect. However, in certain circumstances, for example following severe tissue damage or inflammation, the repair and regeneration of the tissue can become excessive, leading to fibrosis. Fibrosis is the presence of excessive connective tissue and can generically be referred to as scarring.

Within the gastrointestinal tract (GIT), fibrosis can be caused by various diseases especially inflammatory- or ischemic-induced diseases, for example cystic fibrosis, inflammatory bowel diseases, Crohn's disease, ulcerative colitis, coeliac diseases, proctitis, gastrointestinal graft-versus-host disease (GIGVHD), ischemic bowel diseases, necrotizing enterocolitis, and irritable bowel syndrome.

Patients suffering from these chronic conditions often have the added complication of intestinal fibrosis. Fibrosis causes strictures and obstruction of the intestine that require surgery to remove along with portions of the bowel. The therapeutic problems caused by bowel wall fibrosis are common: for example, about 75% of all patients with Crohn's disease have to undergo surgery at least once during the course of their disease. Such fibrosis is a long term complication in inflammatory bowel disease in general, including where therapies control the symptoms but the underlying disease continues to be active and leads to tissue damage in the form of fibrosis.

In contrast to anti-inflammatory treatment, little therapeutic progress has been made with respect to intestinal fibrosis. Current preventive attempts therefore rest primarily on long-term anti-inflammatory treatment. However, this mainly anti-inflammatory approach is often ineffective, leading to surgery and stricturoplasty, which remain the major treatment methods for intestinal fibrosis and, despite the major therapeutic advances in the treatment of Crohn's disease, the incidence of stricture formation in Crohn's disease has not markedly changed. Such observations imply that control of inflammation at the clinical level does not equate with control of fibrogenesis. Unfortunately, even the surgical approach is often only associated with short-term resolution of symptoms, as strictures tend to recur. For further information on intestinal fibrosis see "Wound Healing and Fibrosis in Intestinal Disease", F Rieder et al., *Gut* 2007; 56: 130-139 and "Intestinal fibrosis in IBD—a dynamic, multifactorial process", F Rieder et al., *Nat. Rev. Gastroenterol. Hepatol.* 6, 228-235 (2009).

There are, therefore, currently no satisfactory treatments for intestinal fibrosis. At present, the only option other than surgery to treat the obstructions and strictures caused by fibrosis is endoscopic balloon dilation.

WO 2012/069658 discloses a method of administering to a warm-blooded animal a formulation to treat, or delay the progression of, a fibrotic intestinal disorder, or of maintenance therapy of an animal which has suffered from or is suffering from a fibrotic intestinal disorder, which method comprises orally administering to the animal simultaneously, sequentially or separately an immunosuppressant and a hydroxylase inhibitor. The actives may be in a pharmaceutical composition which comprises a hydrophobic phase in which the immunosuppressant is dissolved. For example, the composition may be a multiple minibead composition wherein the immunosuppressant and the hydroxylase inhibitor are contained in the minibeads, each minibead comprising a water-soluble polymer matrix material and, dispersed within the matrix material, the hydrophobic phase. In an embodiment, the immunosuppressant is cyclosporin A and the hydroxylase inhibitor is hydralazine, in which case the hydralazine may be comprised in the matrix material of such minibeads.

Budesonide (16, 17-butylidendioxy-11β, 21-dihydroxy-1, 4-pregnadien-3,20-dione) is a topical corticosteroid characterized by potent local anti-inflammatory activity, and was initially introduced for the treatment of asthma and rhinitis. Due to an extensive first-pass elimination its systemic bioavailability is only 10-15% compared with other corticosteroid formulations, thus, improved safety and tolerability might be anticipated (Navarro F et al., Treatment of inflammatory bowel disease: safety and tolerability issues. *Am J Gastroenterol* 2003; 98 (12(Suppl): S18-23).

Orally administered budesonide (sold as Entocort®) is indicated for the treatment and maintenance therapy of Crohn's disease involving the ileum and/or the ascending colon. It is proposed also to use a budesonide formulation for the treatment of ulcerative colitis (G R D'Haens et al., *J Crohn's Colitis* (2010) 4, 153-460). Such uses of budesonide are based on the compound's anti-inflammatory activity and the compound is not indicated for the treatment of intestinal fibrosis.

A new extended release budesonide formulation, namely MMX®-budesonide tablets, has been made which is designed to release budesonide at a controlled rate throughout the whole colon for the oral treatment of inflammatory bowel diseases (IBD). See Brunner M et al., *Br J Clin Pharmacol* 61:1, 31-38.

All of the above-mentioned publications, and all other publications mentioned in this specification, are incorporated herein by reference.

SUMMARY

This specification contains data indicating that steroid formulations are efficacious in the treatment of intestinal fibrosis. See Examples 12 and 17. The present invention provides a steroid for use in the treatment of intestinal fibrosis. The steroid may be for enteral administration, for example oral administration. The present invention also provides a method of treating intestinal fibrosis comprising administering a steroid to a subject; the route of administration may be enteral, for example oral.

For all aspects and implementations of the invention, the therapy may affect the entirety of the GIT or a portion thereof. In particular, the therapy may affect one or more regions of the intestines. The entirety of the GIT may therefore be exposed to the steroid. Alternatively, one or more portions of the GIT may be exposed to the steroid, for example the small intestine and/or the large intestine. Particularly, the GIT below the small intestine may be exposed to the steroid, with or without exposure of all or a part of the small intestine to the steroid. In instances where the small intestine is exposed to the steroid, the ileum may be exposed to the steroid, optionally together with one or more other regions of the small intestine. The following region or regions of the GIT may be exposed to the steroid, optionally together with one or more other regions of the GIT: the ileum, or the colon, or the ileum and the colon. The steroid may therefore be comprised in a controlled release formulation adapted to release the steroid to all of the GIT or to one or more portions of the GIT as mentioned in this paragraph or elsewhere in this specification. It is generally understood that the GIT below the small intestine comprises the large intestine which, according to the Terminologia Anatomica (TA), the international standard on human anatomic terminology, comprises the cecum, colon, rectum and anal canal.

Delivery of the steroid to the GIT below the small intestine means that the steroid is released into the lumen of the GIT below the small intestine, and preferably into the colon.

As mentioned, the steroid may be administered enterally. It may be delivered orally. It may be administered rectally. Therefore, there is provided an enteral, e.g. oral or rectal, steroid formulation for use in the treatment of intestinal fibrosis. In one example, the enteral steroid formulation comprises minibeads (sometimes called minicapsules or minispheres) and the minicapsules comprise the steroid. In general, the formulation, especially when an oral formulation, may be a multiple mini-format formulation comprising a multiplicity of mini-format units, e.g. pellets, minibeads, mini-tablets, mini-capsules etc. A mini-format unit may have a largest cross-sectional dimension of 0.5 mm to 5 mm, e.g. 1 mm to 3 mm as in the case of 1 mm to 2 mm.

The formulation may be an immediate release formulation. The formulation may be a controlled release formulation. The formulation may comprise the steroid dissolved or dispersed in a liquid, semi-solid or a solid. In particular, the formulation may comprise the steroid dissolved in a liquid, semi-solid or a solid. The formulation may therefore comprise a liquid, semi-solid or a solid which is a solution containing the steroid. The steroid may be dissolved or dispersed in a liquid or in a wax which has a melting temperature of no more than 37° C.; in particular, the steroid may be dissolved in such a material which may, therefore, be in the form of a solution containing the steroid.

The steroid may be dissolved or dispersed in a medium which comprises or is a macrogol ester. The steroid may be dissolved in such a medium. The medium may be a liquid or a wax, in particular a wax which has a melting point of no more than 37° C. In any medium which comprises or is a macrogol ester, the macrogol ester may be, or may comprise, macrogol-15-hydroxystearate.

The steroid may be dissolved or dispersed in a medium which comprises or is a medium chain triglyceride. The steroid may be dissolved in such a medium. The medium may comprise a medium chain triglyceride and a surfactant, for example an anionic surfactant and/or a non-ionic surfactant.

The steroid may therefore be comprised in an immediate release formulation or in a controlled release formulation.

The steroid may be in solution in a formulation, for example a controlled release formulation. In another example, the steroid is in solution in an immediate release formulation.

The steroid may be comprised in an oral formulation adapted to release the steroid at least in the duodenum. The steroid may be comprised in an oral formulation adapted to release the steroid at least in the jejenum. The steroid may be comprised in an oral formulation adapted to release the steroid at least in the ileum. The steroid may be comprised in an oral formulation adapted to release the steroid at least in the cecum. The steroid may be comprised in an oral formulation adapted to release the steroid at least in the colon. The steroid may be comprised in an oral formulation adapted to release the steroid at least in the small intestine. The steroid may be comprised in an oral formulation adapted to release the steroid at least in the large intestine. The steroid may be comprised in an oral formulation adapted to release the steroid in the small intestine and in the colon. The steroid may be comprised in an oral formulation adapted to release the steroid at least in the ileum and colon. The steroid may be comprised in an oral formulation adapted to release the steroid at least in the duodenum and the colon. The steroid may be comprised in an oral formulation adapted to release the steroid at least in the duodenum, the ileum and the colon. Where a formulation is adapted to release the steroid "at least" in a specified GI region or regions, the formulation may be adapted to release at least 50% of the steroid in the specified region or regions.

The formulation may be adapted to prevent release of the steroid in the stomach and optionally to prevent release in the duodenum, and the jejenum; it may additionally be adapted to prevent release of the steroid in the ileum. The formulation may be adapted to release the steroid exclusively in the colon or in the colon and at least one other region of the intestine, for example in the ileum and colon or in the ileum, in the colon and in at least one other intestinal region. The adaptation may comprise a barrier, for example a coating. The coating may consist of a single layer or plural layers.

The formulation may be a multiple minibead formulation. The minibeads may comprise a water soluble polymer matrix in which the steroid is distributed. The steroid may be distributed in the polymer matrix in any of the following forms:

1) as a solution in the polymer matrix (i.e. the steroid is dissolved in the polymer matrix);
2) as a solid dispersion in the polymer matrix, for example as nanoparticles or microparticles;
3) dissolved in a disperse phase, for example a hydrophobic phase or a surfactant phase (i.e. the disperse phase may be a solution);
4) as particles dispersed in a disperse phase, for example a hydrophobic phase or a surfactant phase;
5) dissolved in the aqueous phase of a water-in-oil or water-in-wax emulsion dispersed in the polymer matrix.

The disperse phase may be a solid, a semi-solid or a liquid. The hydrophobic phase may be an oil or a wax; it may comprise a medium chain triglyceride, optionally in combination with at least one surfactant, e.g. selected from anionic and non-ionic surfactants. The surfactant phase may comprise, or be, a macrogol ester. The macrogol ester may be macrogol-15-hydroxystearate.

The steroid may be comprised in a formulation, for example a controlled release formulation, obtainable by a process comprising:

(i) dissolving a water-soluble polymer in water to form an aqueous solution;
(ii) dissolving or dispersing the steroid in a liquid which will mix with the water to form a colloid to form a steroid solution or dispersion (particularly a solution);
(iii) mixing the aqueous solution and the steroid solution or dispersion to form a colloid;
(iv) ejecting the colloid through a nozzle to form droplets; and
(v) causing or allowing the water-soluble polymer to gel or form a solid.

The method may further include drying the solid. The water may be comprised in an aqueous liquid, e.g. solution, containing constituents other than water. There may therefore be used water as such or another aqueous liquid.

The steroid may be comprised in a formulation, for example a controlled release formulation, obtainable by a process comprising:
(a) dissolving in water a water-soluble polymer and dissolving or dispersing in the water a steroid to form a solution or dispersion and particularly a solution (the polymer may be mixed with the water before the steroid or vice-versa, or the two may be mixed with the water at the same time);
(b) ejecting the solution or dispersion through a nozzle to form droplets; and
(c) causing or allowing the water-soluble polymer to gel or form a solid,
the process optionally further comprising between steps (a) and (b) a step (a1):
(a1) mixing the solution or dispersion and a liquid which will mix with water to form a colloid, thereby to form a colloid.

The method may further include drying the solid. The water may be comprised in an aqueous liquid, e.g. solution, containing constituents other than water. There may therefore be used water as such or another aqueous liquid.

The formulation obtainable as described in the two preceding paragraphs may be an immediate release formulation instead of a controlled release formulation.

The formulation may comprise an administrable unit comprising multiple minibeads. The administrable unit may be a capsule, in the case of oral administration, or a suppository, in the case of rectal administration. In the case of controlled release multiple minibead formulations, either the minibeads and/or a unit comprising multiple minibeads (e.g. a capsule) may be adapted to control release of the active. The formulations may therefore comprise a barrier, for example a coating, as an element of the minibeads and/or as an element of a capsule or other unit comprising multiple minibeads. In the case of multiple minibead formulations, it may be advantageous for the minibeads themselves to be adapted for controlled release, optionally to the exclusion of any unit comprising them.

In the case of multiple minibead formulations, at least some of the minibeads, e.g. all of them, may be adapted to prevent release of the steroid in at least the stomach. For example the minibeads may be adapted to prevent release of the steroid in the stomach and at least the upper small intestine (e.g. duodenum and jejunum); at least some of the minibeads, e.g. all of them, may be adapted to prevent release of the steroid in the stomach and the small intestine. The minibeads may comprise a barrier, for example a single layer coating or a plural layer coating, to prevent release of the steroid. The barrier may comprise an enteric polymer product, for example an enteric coating, or it may comprise an erodible coating. The barrier may comprise a coating which comprises a polymer, e.g. a polysaccharide, which is specifically susceptible to degradation by bacterial enzymes in the colon, i.e. is susceptible to degradation by bacterial enzymes in the colon but not by enzymes higher up the GIT; such a coating may or may not also be erodible.

In a formulation of the invention, at least a portion of the steroid may be protected against release in the stomach, and optionally in the stomach and the small intestine. The formulation may be adapted for a first portion of the steroid to be released in the upper gastrointestinal tract, for example in the small intestine, and a second portion of the steroid to be released in the colon. The second portion may comprise more than half the steroid in the formulation, e.g. at least 60%, at least 70% or at least 80% thereof. As mentioned above, therefore, the formulation may comprise minibeads and more than half of the minibeads, e.g. at least 60% of them, at least 70% of them, at least 80% of them or all of them, may comprise a barrier to prevent release of the steroid in the stomach and small intestine. The protection against release or barrier may be provided by a coating selected from: enteric coatings; coatings adapted to release the steroid in the colon (e.g. such a coating may be erodible and/or comprise a polymer specifically susceptible to degradation by bacterial enzymes in the colon); and coatings comprising a combination of an enteric coating and a coating comprising a polymer specifically susceptible to degradation by bacterial enzymes in the colon.

In a formulation of the invention, therefore, the steroid may all be comprised in minibeads. A multiplicity of such minibeads may be comprised in a unit dosage form, for example a gelatine or other capsule, a sachet, a compressed tablet or a suppository. An oral steroid formulation of the invention may therefore comprise or consist of a multiplicity of minibeads and optionally a capsule or other container for the minibeads. For all aspects and implementations of the invention, an oral formulation may comprise a first population of minibeads adapted to release the steroid in the upper gastrointestinal tract, e.g. in the small intestine, and a second population of minibeads adapted to release the steroid in the colon. The first population of minibeads may be coated with an enteric coating which dissolves in the small intestine; all the minibeads of the formulation may have such a coating or a portion thereof. The second population of minibeads may comprise more than half said steroid in the formulation, e.g. at least 60%, at least 70% or at least 80% thereof. The second population of minibeads may have a coating adapted to release the steroid in the colon; the coating may be an erodible coating and/or may comprise a polymer specifically susceptible to degradation by bacterial enzymes in the colon, i.e. susceptible to degradation by bacterial enzymes in the colon but not by enzymes higher up the GIT.

The formulations of the invention may comprise multiple seamless minibeads (also known as seamless minicapsules or seamless minispheres) comprising the steroid. The seamless minibeads may comprise a water-soluble polymer encapsulating the steroid; such minibeads may comprise a water-soluble polymer matrix also referred to herein as the polymer matrix or the matrix and, dispersed in the matrix, a dispersed phase comprising materials selected from hydrophobic and amphiphilic materials, and combinations thereof. The minibeads may comprise a composition having the characteristics of a dried state of a colloidal system having a continuous aqueous phase comprising a hydrogel-forming polymer. The colloidal system may have a dispersed phase selected from a hydrophobic phase, a water-in-oil emulsion, and a phase comprising self-assembly structures, for example formed primarily by surfactant. The phase comprising self-assembly structures may be selected from a micellar phase selected from micelles, promicelles and combinations thereof. The matrix, or the hydrogel-forming polymer of the dried colloid, may comprise a hydrophilic surfactant. The dispersed phase may comprise a hydrophobic surfactant. For all aspects and implementations of the invention, the matrix (the hydrogel-forming polymer, in the case of minibeads comprising such a polymer) may comprise a hydrophilic surfactant having an HLB value of at least 15 and the dispersed phase may be a hydrophobic phase comprising a non-ionic surfactant having an HLB value of at least 10 but less than that of the hydrophilic surfactant.

The formulation may comprise minibeads coated with an enteric coating which dissolves in the small intestine; all the minibeads of the formulation may have such a coating or a portion thereof.

The hydrogel-forming polymer or water-soluble polymer may comprise or consist of gelatin or another thermotropic hydrogel-forming polymer, or a combination thereof.

The dispersed phase may comprise an excipient selected from medium chain triglycerides and polyglycol mono- and di-esters of 12-hydroxystearic acid, and combinations thereof.

The steroid may be in the form of a liquid solution, semi-solid solution or solid solution e.g. in a hydrophobic or amphiphilic medium.

The invention provides a method of treating a subject, preferably a warm-blooded animal, e.g. a mammal such as a human, to treat intestinal fibrosis, which method comprises enterally, e.g. orally, administering to said animal a steroid. Particular embodiments of this method comprise the administration of a formulation as described herein. The formulation may be administered in a therapeutically effective amount or in a prophylactically effective amount. The formulation may be administered to a human patient in need thereof.

The invention further provides a method of treating a warm-blooded animal, e.g. a mammal such as a human, to inhibit, inhibit, reduce or delay the initiation and/or progression of intestinal fibrosis, which method comprises enterally, e.g. orally, administering to said animal a steroid. Particular embodiments of this method comprise the administration of a formulation as described herein. The formulation may be administered to a human patient in need thereof.

The subject treated with the steroid may have at least one fibrosis-associated disease, condition or state described herein, for example selected from inflammatory bowel diseases and enteropathies, and combinations thereof.

The treatment with the steroid may be to inhibit, delay and/or reduce progression of intestinal fibrosis, and/or to inhibit, delay and/or reduce initiation of intestinal fibrosis. The treatment with the steroid may be to delay and/or reduce progression of intestinal fibrosis, and/or to delay and/or reduce initiation of intestinal fibrosis.

The invention also contemplates combination therapy. It is to be understood that the combination therapies contemplated herein may be achieved by way of the simultaneous, sequential or separate administration of the individual components of the combination(s) disclosed herein. The individual components may be combined in a single composition, for example in a single minibead or in a unit dosage form, e.g. capsule or sachet, containing two or more populations of mini-units, e.g. minibeads, containing different actives/combinations of actives.

The formulations incorporating the steroid may additionally include a hydroxylase inhibitor or be for use in combination therapy with a hydroxylase inhibitor. The methods of the invention may further comprise simultaneous, sequential or separate administration of a hydroxylase inhibitor, e.g. simultaneously as part of the same formulation or separately as part of a kit.

The hydroxylase inhibitor may be selected from DMOG, hydralazine, FG-4497, FG4095, AGN-2979, metirosine, 3-iodotyrosine, aquayamycin, bulbocapnine, oudenone, TM 6008, TM 6089, siRNAs against hydroxylases and antisense therapeutics against hydroxylases, e.g. against PHD1, and combinations thereof. The hydroxylase inhibitor may be DMOG. The hydroxylase inhibitor in particular may be hydralazine. May wish to mention agents that induce hypoxia-inducible factors, of which hydroxylase inhibitors as some.

The formulations incorporating the steroid may additionally include an immunosuppressant or be for use in combination therapy with an immunosuppressant. The methods of the invention may further comprise simultaneous, sequential or separate administration of an immunosuppressant, e.g. simultaneously as part of the same formulation or separately as part of a kit.

The immunosuppressant may be selected from cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides, and combinations thereof. Preferably, the immunosuppressant is a cyclosporin, particularly cyclosporin A.

Those formulations of the invention which include or are for use in combination therapy with a hydroxylase inhibitor may include, or be for use in combination therapy with, an immunosuppressant. The hydroxylase inhibitor and the immunosuppressant may be as described elsewhere herein. The immunosuppressant may be a cyclosporin, particularly cyclosporin A. The hydroxylase inhibitor may be hydralazine or DMOG, in particular it may be hydralazine.

Those formulations of the invention which include or are for use in combination therapy with an immunosuppressant may include, or be for use in combination therapy with, a hydroxylase inhibitor. The hydroxylase inhibitor and the immunosuppressant may be as described elsewhere herein. The immunosuppressant may be a cyclosporin, particularly cyclosporin A. The hydroxylase inhibitor may be hydralazine or DMOG, in particular it may be hydralazine.

The formulations of the invention comprising a steroid may therefore further comprise a hydroxylase inhibitor and an immunosuppressant. The hydroxylase inhibitor and the immunosuppressant may be as described elsewhere herein. The immunosuppressant may be a cyclosporin, particularly cyclosporin A. The hydroxylase inhibitor may be hydralazine or DMOG, in particular it may be hydralazine.

The steroid may be any steroid selected from natural or synthetic steroids.

In particular, the steroid is budesonide.

Included in the invention is an enteral formulation, for example an oral formulation, comprising a steroid and for use in the treatment of intestinal fibrosis.

BRIEF DESCRIPTION OF THE DRAWINGS

Embodiments of the invention are further described hereinafter with reference to the accompanying drawings, in which.

DETAILED DESCRIPTION

Figure 1:
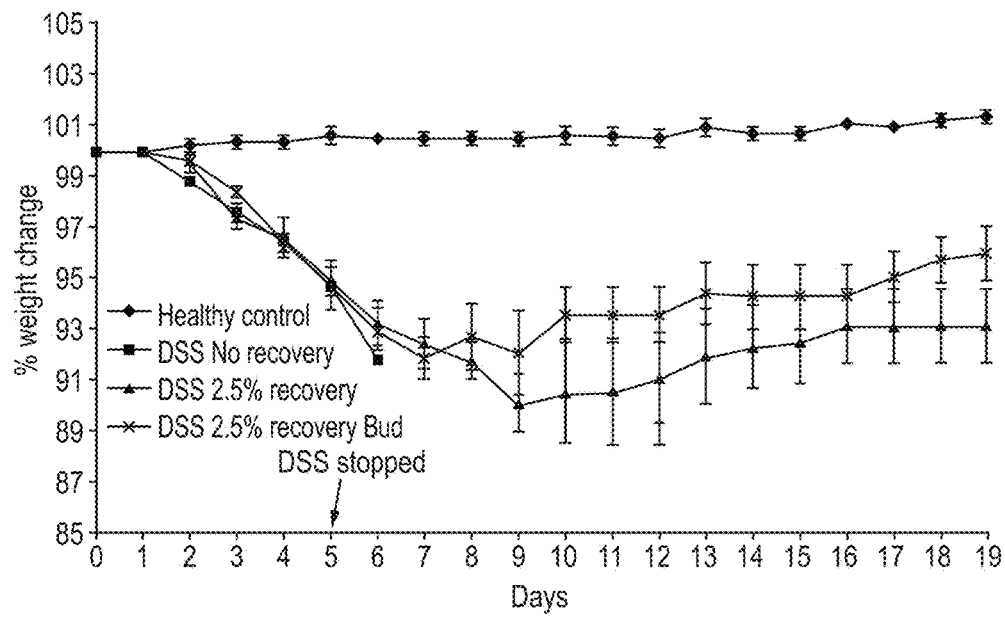
FIG. 1 is a plot of weight change showing the effect of a budesonide formulation of the invention (DSS recovery—Bud), see Example 12.

The present products (steroids, formulations, compositions) and methods are as previously described for use in the treatment of intestinal fibrosis. They are therefore for use in the treatment of fibrotic disorders. The treatments include by way of example maintenance therapy or prophylaxis as well as treatment to improve the condition of a patient.

The invention is predicated on the use of a steroid, particularly a corticosteroid or an anti-inflammatory steroid or a first pass metabolised steroid, to treat intestinal fibrosis. The invention is to be understood accordingly and it not limited, therefore, to being performed using the formulations described in this specification, since the choice of formulation is not critical to the invention.

Nonetheless, all the formulations described herein themselves form part of the invention without limitation to the use to which they are put. The applicant therefore reserves the right to claim all the formulations described herein in composition of matter claims. For example, formulations described herein may be useful for treating celiac disease or other conditions that have inflammation and fibrosis and part of their pathology. The use of the formulations described herein to treat intestinal fibrosis is of course included also in the invention.

The invention will now be described in detail by reference to the various components which the composition of the invention may comprise. The term "excipient" may be used occasionally to describe all or some of the components other than the active principle(s) bearing in mind that some excipients can be active and that some active principles can have excipient character.

If not otherwise stated, ingredients, components, excipients etc of the composition of the invention are suitable for one or more of the intended purposes discussed elsewhere herein.

For the avoidance of doubt, it is hereby stated that the information disclosed earlier in this specification under the heading "Background" is relevant to the invention and is to be read as part of the disclosure of the invention.

The terms "active", "active ingredient", "active compound", etc are used throughout this specification to refer to compounds that possess a beneficial effect on the human or animal body when administered thereto. The terms are also used to describe the steroid of the invention as well as any other active ingredient that may be used in combination with the steroid. Therefore, where a feature of the description is referred to as being relevant to an "active", etc then this feature is applicable to the steroid and any active ingredients combined with the steroid.

The terms "dry" and "dried" as applied to compositions of the disclosure may each include reference to compositions containing less than 5% free water by weight, e.g. less than 1% free water by weight. Primarily, however, "dry" and "dried" as applied to compositions of the disclosure mean that the hydrogel present in the initial solidified composition has dried sufficiently to form a rigid composition.

"Medium chain triglyceride" means a C6-C12 fatty acid tri-ester of glycerol. Commercially available formulations of medium chain triglycerides (MCTs) are typically derived from natural products and contain minor amounts of other components, for example glycerides of differing chain length, mono- and di-glycerides and free fatty acid. Such commercially available formulations are medium chain triglycerides within the meaning of this specification.

The term "subject" includes humans and other mammals such as domestic animals (e.g., dogs and cats), as well as fish. In particular implementations, the term "subject" denotes a human.

The term "self-assembly structure" refers to any type of micelle, -liposome, vesicle, microemulsion, lyotropic phase, laminar or other self-organised structure that forms spontaneously in the presence of an aqueous environment, or combination thereof. As is known, such self-assembly structures form when a self-assembly structure-forming substance, e.g. comprising or consisting of a surfactant, is present above a certain critical concentration. The term includes, for example, micelles, inverted micelles and liposomes, and combinations thereof. The self-assembly structures referred to in this specification may comprise, or be, micelles. More information on self-assembly structures can be found in "Dynamics of Surfactant Self-assemblies Micelles, Microemulsions, Vesicles and Lyotropic Phases" by Raoul Zana, particularly Chapter 1, all of which is incorporated herein by reference. The release of self-assembly structures from a bead or other composition may be determined by contacting the composition with water and observing for such structures by dynamic light scattering.

"Effective amount" means an amount sufficient to result in the desired therapeutic or prophylactic response. The therapeutic or prophylactic response can be any response that a user (e.g., a clinician) will recognize as an effective response to the therapy. It is further within the skill of one of ordinary skill in the art to determine appropriate treatment duration, appropriate doses, and any potential combination treatments, based upon an evaluation of therapeutic or prophylactic response.

The term "fibrosis" includes reference to conditions in which excessive connective tissue is present and, therefore, to conditions in which there is increased collagen deposition compared to healthy individuals. The term "fibrosis" also includes reference to conditions in which there is increased deposition of other extracellular matrix ("ECM") proteins. In this invention, such collagen and/or other ECM proteins may be deposited in any tissue of the GIT. In this invention, fibrosis may be induced by any mechanism and may be associated with any disease or condition effecting the GIT. Intestinal fibrosis is usually considered to be a common complication of enteropathies, often with distinct initiating pathophysiology, for example inflammatory bowel disease (IBD), radiation enteropathy, graft-versus-host disease, collagenous colitis, eosinophilic enteropathy, drug-induced enteropathy, sigmoid diverticulitis, solitary rectal ulcer, cystic fibrosis, intra-peritoneal fibrotic adhesions, desmoplastic reaction in gastrointestinal tumors (familial adenomatous polyposis-FAP), desmoid tumors, gastrointestinal (GI) stromal tumors (GISTs) and post-surgical intestinal adhesions and strictures leading to intestinal stenosis and obstruction. The list of enteropathies in the previous sentence is not a comprehensive list of enteropathies in which fibrosis may occur: in general all or most enteropathies may be associated with fibrosis. Fibrosis associated with these and all other enteropathies is included in this specification. Fibrosis may be pathogenic or non-pathogenic in origin. The reader is further referred to the discussion of fibrosis earlier in this specification under the heading "Background" and the publications mentioned in that connection, all of which disclosures are comprised in the meaning of the term "fibrosis" as used herein. In any event, the term "fibrosis" includes reference to any condition, state or disorder which is considered to be fibrosis within the scope of sound medical judgment.

The term "enteropathy" refers to a disease or disorder of the intestinal tract, for example of any one or more regions of the intestinal tract. The term therefore includes references to all diseases and disorders of the small intestine, or any of its regions, and/or of the large intestine, or any of its regions. An enteropathy may occur as part of, or in the setting of, a systemic disease or disorder and/or of a disease or disorder which affects one or more other organs and/or tissues of the body. An enteropathy may be pathogenic or non-pathogenic in origin. Pathogenic enteropathies are a particular problem in developing countries where children infected by various pathogens including GI pathogens, develop enteropathy with resulting stunted growth, mental development, risk of infection and other deleterious consequences. A non-limiting list of examples of enteropathies which are associated with fibrosis is given in the preceding paragraph. In any event, the term "enteropathy" includes reference to any condition, state or disorder which is considered to be an enteropathy within the scope of sound medical judgment.

The term "a steroid susceptible to first pass metabolism" means a steroid which within sound medical judgment, is considered to undergo first pass metabolism. Therefore, only a part of an initial steroid dosage becomes systemically available.

The treatments provided by this invention may include any one or more of: maintaining the gastrointestinal health of a subject who has or is at risk of having gastrointestinal fibrosis; restoring or improving the gastrointestinal health of a subject who has or is at risk of having gastrointestinal fibrosis; reducing or controlling gastrointestinal fibrosis; delaying the progression of gastrointestinal fibrosis; delaying, avoiding the need for or reducing the likelihood of surgical intervention to treat gastrointestinal fibrosis, for e.g. to treat strictures. Such treatments of gastrointestinal fibrosis may be part of a combination therapy regime for the treatment of a gastrointestinal disorder having, or at risk of having, a fibrotic aspect.

The term "treatment", and the therapies encompassed by this invention, include the following and combinations thereof: (1) inhibiting, e.g. delaying initiation and/or progression of a state, disorder or condition; (2) preventing or delaying the appearance of clinical symptoms of a state, disorder or condition developing in an animal (e.g. human) that may be afflicted with or predisposed to the state, disorder or condition but does not yet experience or display clinical or subclinical symptoms of the state, disorder or condition; (3) inhibiting the state, disorder or condition (e.g., arresting, reducing or delaying the development of the disease, or a relapse thereof in case of maintenance treatment, of at least one clinical or subclinical symptom thereof); and/or (4) relieving a state disorder or condition (i.e., causing regression of the state, disorder or condition or at least one of its clinical or subclinical symptoms). The benefit to a patient to be treated may be either statistically significant or at least perceptible to the patient or to the physician. It will be understood that a medicament will not necessarily produce a clinical effect in every patient to whom it is administered, and this paragraph is to be understood accordingly. The compositions and methods described herein are of use for therapy and/or prophylaxis of the conditions mentioned herein. The terms "state", "disorder" and "condition" refer herein to a state, disorder or condition which is associated with gastrointestinal fibrosis, for example which carries with it an increased risk of gastrointestinal fibrosis as compared to the risk of a normal population. In particular, the state, order or condition treated by a steroid in accordance with the invention is gastrointestinal fibrosis; the gastrointestinal fibrosis may be treated prophylactically in a subject who has not experienced gastrointestinal fibrosis but is at increased risk of suffering from it, for example because the subject suffers at least intermittently, e.g. continuously, from an inflammatory bowel disease. Alternatively, the gastrointestinal fibrosis may be treated therapeutically or prophylactically in a subject who suffers from gastrointestinal fibrosis, in particular to arrest, inhibit, reduce or delay progression of such gastrointestinal fibrosis.

The treatments may include maintenance therapy of patients who have suffered a GI tract disorder and whose condition has subsequently improved, e.g. because of treatment. Such patients may or may not suffer a symptomatic GIT disorder. Maintenance therapy aims to arrest, inhibit, reduce or delay (re-)occurrence or progression of a GIT disorder.

The invention primarily concerns the treatment of humans but other warm-blooded animals, e.g. mammals, are also embraced by the invention, for example agricultural mammals and domesticated mammals. Examples are pigs, dogs and cats. For example, the compositions and methods of the invention may be applied to porcine proliferative enteropathy.

The subject may be suffering from an inflammatory bowel disease. The subject may be suffering from Crohn's disease. The subject may be suffering from ulcerative colitis. The subject may be suffering from irritable bowel syndrome (e.g. with constipation, diarrhea and/or pain symptoms), celiac disease, stomach ulcers, diverticulitis, pouchitis, proctitis, mucositis, radiation-associated enteritis, short bowel disease, or chronic diarrhea. The subject may be suffering from GVHD. As used herein, "GVHD" in particular means GI-GVHD (gastrointestinal graft-versus-host disease). The subject may be suffering from diversion colitis, ischemic colitis, infectious colitis, chemical colitis, microscopic colitis (including collagenous colitis and lymphocytic colitis), atypical colitis, pseudomembraneous colitis, fulminant colitis, autistic enterocolitis, interdeminate colitis, Behcet's disease, jejunoiletis, ileitis, ileocolitis and granulomatous colitis. The invention in its aspects and implementations is applicable to subjects having the disorders mentioned in this paragraph, therefore.

The subject may be suffering from an enteropathy, for example gluten-sensitive enteropathy, hemorrhagic enteropathy, protein-losing enteropathy, radiation enteropathy, enteropathy associated with T-cell lymphoma, autoimmune enteropathy or porcine proliferative enteropathy, or any other enteropathy mentioned in this specification. The subject may be suffering from an enteropathy not mentioned in this specification. Colorectal carcinoma and adenocarcinoma are inflammation-related diseases. The treatments and products described herein are useful for patients who have suffered from, do suffer from or have risk factors for, such cancers. The disclosed therapies and products may be used in (e.g. as part of) the treatment of colorectal carcinomas or as part of the maintenance therapies of patients who have suffered from such carcinomas (in this regard, there is considered to be a strong inflammation component in the aetiology of colorectal cancer). The invention in its aspects and implementations is applicable to subjects having the disorders mentioned in this paragraph.

Solubilities of compounds, e.g. actives, in a solvent (for example water) may be defined as follows, the solubility being measured at 25° C. and parts being by weight:

| Descriptive Team | Parts of Solvent for 1 part of solute |
|---|---|
| Very Soluble | Less than 1 |
| Freely Soluble | From 1 to 10 |
| Soluble | From 10 to 30 |
| Sparingly Soluble | From 30 to 100 |
| Slightly Soluble | From 100 to 1000 |
| Very Slightly Soluble | From 1000 to 10,000 |
| Practically Insoluble | More than 10,000 |

Typically, but not necessarily, the invention provides that active agents which are practically insoluble, very slightly soluble or sparingly soluble in water are in the form of a liquid, semi-solid or solid solution in a hydrophobic or amphiphilic environment, e.g. medium.

Actives which are not particularly water-soluble, e.g. are practically insoluble, very slightly soluble or slightly soluble, perhaps even are sparingly soluble, may be more soluble in a suitable dispersed phase of a minibead than in the aqueous phase, and may therefore advantageously be incorporated in the dispersed phase. Steroids are typical examples of such actives.

Active Agents

The invention is based on the use of a steroid to treat gastrointestinal fibrosis.

The steroid may be a corticosteroid. Such corticosteroids generally may be any steroid produced by the adrenal cortex, including glucocorticoids and mineralocorticoids, and synthetic analogues and derivatives of naturally occurring corticosteroids having anti-inflammatory activity. Examples of corticosteroids that can be used are aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph.

The steroids used in the present invention may be water-soluble, water-insoluble or water-dispersible. The steroids used in the present invention may be oil-soluble, oil-insoluble or oil-dispersible. Water-soluble corticosteroids may be salts, for example alkali metal or ammonium salts, prepared from a corticosteroid having a free hydroxyl group and an acid. The acid may be an organic acid, for example a C2-C12 aliphatic, saturated or unsaturated dicarboxylic acid, or an inorganic acid, for example phosphoric acid or sulphuric acid. Also, acid-addition salts of corticosteroids may be used. If more than one group in the corticosteroid molecule is available for salt formation, mono-, as well as di-, salts may be useful. As alkaline metal salts, the potassium and sodium salts are preferred. Other positively or negatively charged derivatives of corticosteroids can also be used. Specific examples of water-soluble corticosteroids are betamethasone sodium phosphate, desonide sodium phosphate, dexamethasone sodium phosphate, hydrocortisone sodium phosphate, hydrocortisone sodium succinate, methylprednisolone disodium phosphate, methylprednisolone sodium succinate, prednisolone sodium phosphate, prednisolone sodium succinate, prednisolamate hydrochloride, prednisone disodium phosphate, prednisone sodium succinate, triamcinolone acetonide disodium phosphate and triamcinolone acetonide disodium phosphate.

Water-soluble steroids may be salts, for example betamethasone phosphate, dexamethasone phosphate, prednisolone phosphate, prednisolone succinate, hydrocortisone succinate.

Of these water-soluble steroids, prednisolone disodium phosphate, prednisolone sodium succinate, methylprednisolone disodium phosphate, methylprednisolone sodium succinate, dexamethasone disodium phosphate and betamethasone disodium phosphate may be mentioned in particular.

Topical corticosteroids which are susceptible to first pass metabolism are of special interest. Examples thereof are budesonide, flunisolide, fluticasone proprionate, rimexolone, butixocort, tixocortol and beclomethasone. It will be understood that these compounds may be in the form of the salts, esters, conjugates and prodrugs thereof, for example one mentioned elsewhere in this specification.

Salts, prodrugs, esters, conjugates, stereoisomers, enantiomers and solvates of the steroids mentioned herein may be used to perform the invention. Esters may be esters of aliphatic acids, for example fatty acids. Prodrugs, esters and conjugates may be in the form of salts. In this case of steroid salts mentioned herein, instead of being used as the mentioned salt, the steroid may be used as another salt, as the free compound or as a conjugate, ester or prodrug, which conjugates, esters and prodrugs may be in salt form.

The steroid may be budesonide. The steroid may be a combination of steroids comprising budesonide.

Budesonide may be in the form of the free molecule or it may be as a conjugate or prodrug thereof, which conjugates and prodrugs may, where they have an acidic or basic group, be in salt form. As an example may be mentioned budesonide-beta-D-glucuronide, which is not absorbed in the small intestine but is hydrolysed by colonic bacterial and mucosal beta-glucuronidase to release free budesonide into the colon. Also to be mentioned are budesonide-dextran conjugates and budesonide esters.

The formulations useful in performing the invention include any enteral formulations whose administration results in release of a corticosteroid, for example budesonide or another corticosteroid mentioned in this specification.

In particular, therefore, the invention provides budesonide for use in treating intestinal fibrosis. Also provided is the use of budesonide for the manufacture of a medicament for treating intestinal fibrosis.

The steroid, which in particular may be budesonide, may be used in combination therapy with one or more other active agents.

The steroid may be used in combination therapy with another steroid, e.g. a plurality of other steroids or a single other steroid, and optionally with one or more active agents other than steroids.

In the case of combination therapy, the active agents may be administered simultaneously, separately or sequentially. The combination of active agents may be in the form of a fixed combination, i.e. all included in the same formulation. Where three or more active agents are administered in combination therapy, a sub-combination of e.g. two of the active agents may be in the form of a fixed combination.

The steroid may be used in combination therapy with a methylxanthene, for example theophylline, to overcome, modulate, treat or inhibit steroid resistance. The steroid may be used in combination therapy with a single methylxanthene or a combination of methylxanthenes.

In the case of combination therapy, the active agent(s) administered as well as the steroid may be selected from active agents useful for treating inflammatory bowel diseases. For example such active agents may be selected from immunosuppressants and direct or indirect promoters of the activity or expression of hypoxia-inducible factor (HIF), particularly HIF-1, and combinations of the aforegoing. Promoters of the activity or expression of hypoxia-inducible factor (HIF), particularly HIF-1

The steroid may therefore be used in combination therapy with an immunosuppressant. The identity of the immunosuppressant is not critical. It may be, or comprise, any one or more of: a calcineurin inhibitor, cyclosporin A (ciclosporin); mTOR inhibitors, e.g. sirolimus (rapamycin), sirolimus derivatives for example everolimus, 32-deoxorapamycin; a mycophenolate, eg. mycophenolic acid; methotrexate; azathioprine or mercaptopurine; mitoxantrone; cyclophosphamide; macrolide immunosuppressant, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

The steroid may be used in combination therapy with an active agent selected from calcineurin inhibitors, macrolide immunosuppressants and mTOR inhibitors.

Exemplary calcineurin inhibitors are cyclosporins, tacrolimus, and pimecrolimus.

For examples of mTOR inhibitors useful in the invention the reader is referred to WO2007/068462, which is incorporated herein by reference in its entirety. Particular examples are rapamycin, 40-O-(2-hydroxy)-ethyl-rapamycin, 32-deoxorapamycin, 40-[3-hydroxy-2-(hydroxymethyl)-2-methylpropanoate]-rapamycin, ABT578 and AP23573.

As examples of macrolide immunosuppressants may be mentioned tacrolimus, ascomycins, sirolimus, cyclosporin, pimecrolimus.

It will be recalled that the steroid may be used in combination therapy with a direct or indirect promoters of the activity or expression of HIF-1. To be mentioned as indirect promoters of the activity or expression of HIF-1 are hydroxylase inhibitors. Such hydroxylase inhibitors may inhibit an asparaginyl hydroxylase; it may inhibit a prolyl hydroxylase; it may inhibit both. The hydroxylase inhibitor may be selected from, or comprise, DMOG, hydralazine, FG-4497, FG4095, AGN-2979, metirosine, 3-iodotyrosine, aquayamycin, bulbocapnine, oudenone, TM 6008, TM 6089, siRNAs against hydroxylases and antisense therapeutics against hydroxylases, e.g. against PHD1, and combinations thereof. In any event, two or more hydroxylase inhibitors may be used.

The steroid, in particular budesonide, may be used in combination therapy with another anti-fibrotic agent, for example selected from caspase inhibitors, peroxisome proliferator-activated receptor-g (PPAR-g) agonists such as pioglitazone, TGF-b blockers, colchicines, relaxin, adiponectin, endothelin A, angiotensin receptor blockers, cannabinoids and agents altering the MMP-TIMP balance, and wound healing agent (Ilodecakin, Mannose-6-Phosphate).

The steroid, in particular budesonide, may therefore be used in combination therapy with one, two or three of (a), (b) and (c) below:
  (a) an immunosuppressants;
  (b) a promoter of the expression or activity of HIF, for example a hydroxylase inhibitor;
  (c) another anti-fibrotic agent.

In particular, such combination therapy may use the steroid, particularly budesonide, an immunosuppressant and a hydroxylase inhibitor. The immunosuppressant may be cyclosporin A. The hydroxylase inhibitor may DMOG or hydralazine.

The disclosure therefore includes a steroid, in particular budesonide, for use in treating intestinal fibrosis in combination therapy with:
(i) cyclosporin A; or
(ii) DMOG; or
(iii) hydralazine; or
(iv) cyclosporin A and DMOG; or
(v) cyclosporin A and hydralazine.

The combination therapy may include use of one or more additional active agents.

In those instances where the steroid is for use in combination therapy, the steroid and the active agent or agents with which the steroid is for use in combination therapy are all comprised in a fixed combination.

This specification describes elsewhere steroid formulations in the form of minibeads which comprise a water-soluble polymer matrix and, dispersed in the matrix, a dispersed phase comprising materials selected from hydrophobic and amphiphilic materials, and combinations thereof. In particular, such minibeads may comprise a dried aqueous colloid. The steroids of the disclosure are generally included in the dispersed phase, typically in solution in the dispersed phase. Such minibeads may contain one or more active agents in addition to the steroid.

An active agent used in combination therapy with the steroid may be water-soluble or water-dispersible and dissolved or dispersed in a water-soluble polymer, e.g. a hydrogel-forming polymer, comprised in the formulation in which the steroid is incorporated. The polymer may constitute the polymer matrix of a minibead or dried colloidal formulation as extensively described herein.

An active agent used in combination therapy with the steroid may be hydrophobic and dissolved in a hydrophobic medium, e.g. an oil, a wax or the interior of a micelle or other self-assembly structure comprised in the formulation in which the steroid is incorporated. The oil, wax or micelle may form the dispersed phase of a minibead or dried colloidal formulation as extensively described herein.

The steroid and active agent(s) may be in solution in a liquid (e.g. an oil or a self-assembly structure) or in a solid or semi-solid medium (e.g. a wax or a water-soluble polymer). However, water-soluble or water-dispersible active agents in particular may be included in the polymer matrix of a minibead in particulate form, for example as a dried aqueous dispersion. Solid particulate forms may be microparticles or nanoparticles.

In certain formulations of the invention the steroid is a water-soluble steroid. Where the steroid is water soluble it is dissolved and/or dispersed in the water soluble polymer matrix of a minibead. The water-soluble steroid may be in combination with a further water-soluble active ingredient, for example another steroid or a hydroxylase inhibitor, such as hydralazine. In this case both water-soluble actives may be present in the water-soluble polymer matrix. Where the steroid is water-soluble the formulation may not contain a dispersed phase. Formulations of the present invention may contain a water-soluble steroid present in solution in the water-soluble polymer matrix and an oil soluble active ingredient present in the dispersed phase, for example another steroid or an immunosuppressant, such as cyclosporin A.

The minibeads of the disclosure, therefore, provide a hydrophilic environment (the water-soluble polymer) for hydrophilic drugs and a hydrophobic environment (the dispersed phase) for hydrophobic drugs. Hydrophobic drugs are typically in solution in the dispersed phase but suspensions are not excluded. Hydrophilic drugs are often also in solution in the matrix phase, but may be particulate, e.g. as nanoparticles, in the matrix phase.

It will be understood that, where the steroid and one or more other actives are used in combination therapy they may be in a combination formulation. For example, two or more actives may be included in a single population of minibeads (each minibead contains the combination of actives), as already described. Alternatively a composition (e.g. capsule or other container) may comprise two or more different populations of minibead, the minibeads of each population having one or more actives not found in the other population; for example, there may be two minibead populations, each containing a single active agent different from that in the other population. As another alternative, any two actives which are co-administered may be administered in separate formulations, e.g. simultaneously, separately or sequentially and often simultaneously (i.e. more or less at the same time).

Formulations

The invention provides amongst other things pharmaceutical formulations comprising a steroid and for use in a treatment as mentioned herein. The formulations may be for enteral use, for example oral or rectal use. The formulations comprise at least one steroid and optionally another active agent as specified herein. The identity of the formulation used to administer the steroid is not critical to the invention. By way of example, the formulations may be multiple mini-unit formulations, e.g. multiple minitablet or multiple minibead formulations, i.e. comprise a multiplicity of minibeads, for example at least 25 minibeads, e.g. at least 50 minibeads.

The active compounds may be in finely divided form, for example it may be micronised.

The formulations may comprise minibeads and the minibeads may comprise or consist of minibeads in which the content of at least hydrophobic active agent(s) is in dissolved form, i.e. is in solution.

The formulations may comprise a water-soluble polymeric matrix in which said active agent(s) is or are dispersed or dissolved, the matrix in particular forming minibeads which may additionally comprise one or more coatings. The polymer material constituting the matrix may be, or may comprise, a hydrogel-forming polymer. The polymer part of the matrix may therefore consist of a hydrogel-forming polymer. The formulations may comprise minibeads comprising a polymeric matrix phase and a dispersed phase. Thus the formulations may comprise minibeads comprising a hydrogel-forming polymer and a dispersed phase. Water-soluble actives may be dissolved in the polymeric matrix or dispersed in the polymeric matrix in particulate form, e.g. as micro- or nano-particles. The term "water-soluble" in this paragraph and elsewhere in the specification includes reference to substances which are categorised as soluble, freely soluble and very soluble. It may include reference to substances which are sparingly soluble.

The matrix may include in addition to the water-soluble polymer and any dissolved active(s), other ingredients such as, for example, excipients which may, for example, modulate the behaviour of the matrix phase and/or of other constituents during manufacture and/or after administration.

The matrix advantageously comprises a hydrophilic surfactant having an HLB value of at least 10 and particularly of at least 15.

The hydrophilic surfactant may have an HLB value of at least 15, and optionally of at least 18, e.g. of at least 20 or at least 25.

The hydrophilic surfactant may be an anionic surfactant. The anionic surfactant may have an HLB value of at least 30, e.g. at least 35, for example of 40±2. The anionic surfactant may comprise or be an alkyl sulfate salt. The alkyl sulfate salt may be sodium dodecyl sulfate (SDS). The water-soluble polymer matrix material may further contain a non-ionic surfactant having an HLB value of at least 10 but less than that of the hydrophilic surfactant. The non-ionic surfactant may comprise a poly(oxyethylene) group, e.g. comprise a glycerol polyethylene glycol ricinoleate (as in the case of Cremophor EL).

The hydrophilic surfactant may be selected from cationic and non-ionic surfactants, and combinations thereof.

The formulations may comprise gelatin as a water-soluble polymer. The gelatin may be the sole water-soluble polymer.

The water-soluble matrix material may be selected from a hydrocolloid, a non-hydrocolloid gum and chitosan and derivatives thereof.

The formulations may comprise a unit solid which may be a minibead having a diameter of not more than 10 mm, e.g. of not more than 5 mm, the formulation optionally comprising a plurality of such minibeads. The minibead may be monolithic, optionally with layers thereon. The one or more minibeads may comprise a controlled-release polymer, e.g. incorporated in the matrix and/or coated on it. The minibeads may comprise plural controlled release polymers, which may be present as a mixture or be separated, e.g. a first controlled-release polymer may be comprised in a coat and a second (different) controlled-release polymer may be comprised in the matrix. The or each polymer may be associated with one or more excipients, e.g. a pore former. At least one controlled-release polymer may be an extended release polymer or an enteric polymer. The minibead(s) may have a coat which comprises the controlled release polymer and optionally a polymer specifically susceptible of degradation by bacterial enzymes.

In embodiments, the or each minibead comprises a controlled-release polymer which is ethylcellulose comprised in a coating on the minibead and optionally in association with an emulsification agent, for example ammonium oleate. The ethylcellulose may also be in association with a plasticizer, e.g. dibutyl sebacate or medium chain triglycerides. The coating may further comprise a polymer specifically susceptible of degradation by bacterial enzymes. The polymer susceptible of degradation by bacterial enzymes may be water-soluble, and preferably is pectin.

The dispersed phase may be composed of, or predominantly of, hydrophobic and/or amphiphilic materials in which hydrophobic active(s) may be dissolved. Generally, the dispersed phase may provide a hydrophobic environment either in a hydrophobic material or within a hydrophobic part of a self-assembly structure. The dispersed phase may comprise a water-immiscible liquid. The water-immiscible liquid may be present in the minicapsules as droplets. The water-immiscible liquid may comprise a liquid lipid and optionally a solvent miscible therewith, in which solvent a water-insoluble active ingredient is soluble. The liquid lipid may be a medium chain triglyceride (MCT) composition, the medium chain triglyceride(s) being one or more triglycerides of at least one fatty acid selected from $C_6$-$C_{12}$ fatty acids The liquid lipid may be a caprylic/capric triglyceride, i.e. a caprylic/capric triglyceride composition (which it will be understood may contain minor amounts of compounds which are not caprylic/capric triglycerides).

For all embodiments of the invention, a water-insoluble active ingredient may have a solubility in the water-immiscible liquid of at least 5 mg/ml, and often of at least 10 mg/ml, e.g. at least 25 mg/ml, for example at least 50 mg/ml.

The solvent which is optionally included in a water-immiscible liquid may be miscible with both the liquid lipid and with water, e.g. it may be 2-(2-ethoxy)ethanol.

The dispersed phase, e.g. water-immiscible phase (water-immiscible droplets), may represent from 10-85% by dry weight of the composition.

The unit solid or minibead may have a low water content.

In an embodiment the pharmaceutical formulation is a capsule or other unit comprising a population of minibeads which have a diameter of at most 10 mm and which comprise a hydrophilic surfactant-containing water-soluble polymer matrix material and a coating on the matrix material, wherein the hydrophilic surfactant has an HLB value of at least 15, and wherein the coating comprises a controlled-release polymer. The coating may be a barrier membrane for extended release of the active agent(s) and/or may be a coating which resists becoming degraded or becoming of increased permeability in the conditions of the GI tract above the colon but which becomes degraded or of increased permeability in the conditions of the colon. The minibeads may further comprise in the polymer matrix part a non-ionic surfactant comprising a poly(oxyethylene) group and the hydrophilic surfactant may be an anionic surfactant. The capsule or other unit may comprise a second population of minibeads.

For all embodiments of the invention, the formulation may further comprise another active pharmaceutical ingredient, in addition to a steroid.

The formulation may comprise a gelatin or other capsule containing a plurality of minibeads into which the water-soluble polymer matrix material is formed.

Also disclosed is a method of making dried colloid formulations of the disclosure, which method comprises mixing a water immiscible phase, the dispersed phase, with an aqueous phase, the continuous phase, comprising a water-soluble polymer matrix material to form a liquid colloid and then causing the liquid colloid to solidify. The liquid colloid may be formed into droplets which are then exposed to a solidification medium (e.g. a liquid colloid in which the water-soluble polymer is a thermotropic hydrogel-forming polymer is exposed to a cool water-immiscible oil to cool the polymer so that it gels). In the case of a dried emulsion formulation, the water-immiscible phase is hydrophobic. In the case of a dried self-assembly structure composition, the water-immiscible phase is usually a surfactant phase (also normally containing components additional to the surfactant).

The invention includes a colloidal composition, e.g. an emulsion or aqueous self-assembly structure composition, useful in making the formulations of the invention and comprising a steroid, for example in solution in the water-immiscible phase of the colloid.

Further provided is an emulsion for use in manufacturing a minibead of the disclosure, the emulsion comprising a water immiscible phase (e.g. oil droplets or micelles or other self-assembly structures) dispersed in an aqueous phase, wherein the aqueous phase comprises a water-soluble polymer matrix material and in that the emulsion comprises a steroid, e.g. in solution.

The invention further includes a pharmaceutical formulation for oral administration, obtainable by:
(A) mixing together at least the following materials to form a colloid:
   i) a steroid;
   ii) an aqueous phase comprising water and a water-soluble polymer material;
   iii) a hydrophobic liquid or a self-assembly structure-forming surfactant;
   iv) optionally a hydrophilic surfactant having an HLB value of at least 10;
   v) optionally one or more excipients which are miscible with or soluble in the hydrophobic liquid or the self-assembly structure-forming surfactant to increase the solubility of the steroid in said liquid or surfactant, wherein the steroid is soluble in the hydrophobic liquid or self-assembly structure-forming surfactant when combined with any said one or more excipients; and
(B) formulating the colloid into a pharmaceutical composition comprising a unit solid which comprises the colloid in a dry state. The composition may be adapted to release the steroid at least into the colon.

The mixing together may comprise mixing the steroid, the hydrophobic liquid or self-assembly structure-forming surfactant, any said one or more excipients and any other constituents soluble in the hydrophobic liquid or self-assembly structure-forming surfactant to form a clear solution. Similarly, the water is mixed with the water-soluble polymer material, the hydrophilic surfactant (where present) and any other constituents of the aqueous phase of the colloid. The clear solution is then mixed with the aqueous mix to form the colloid.

The formulating may comprise ejecting the emulsion through a single-orifice nozzle, e.g. having a diameter of from 0.5-5 mm, to form drops which are then caused or allowed to fall into a cooling oil or other hardening medium and allowed to harden to form minibeads, after which the minibeads are recovered from the cooling oil and dried.

All optional features previously described in relation to the invention are applicable to the below described methods and all other aspects and embodiments of the invention. Likewise, optional features described in relation to the below described methods are applicable to embodiments and aspects of the invention described earlier and later in this specification.

Surfactants

In the description and claims of this specification, the term "surfactant" is employed as a contraction for "surface active agent". For the purposes of this description and claims, it is assumed that there are four major classifications of surfactants: anionic, cationic, non-ionic, and amphoteric (zwitterionic). The non-ionic surfactant remains whole, has no charge in aqueous solutions, and does not dissociate into positive and negative ions. Anionic surfactants are water-soluble, have a negative charge and dissociate into positive and negative ions when placed in water. The negative charge lowers the surface tension of water and acts as the surface-active agent. Cationic surfactants have a positive charge, and also dissociate into positive and negative ions when placed in water. In this case, the positive ions lower the surface tension of the water and act as the surfactant. The amphoteric (zwitterionic) surfactant assumes a positive charge in acidic solutions and performs as a cationic surfactant, or it assumes a negative charge in an alkaline solution and acts as an anionic surfactant.

Surfactants can also be classified according to their hydrophilic-lipophilic balance (HLB) which is a measure of the degree to which the surfactant is hydrophilic or lipophilic, determined by calculating values for the different regions of the molecule, as described (originally for non-ionic surfactants) by Griffin in 1949 and 1954 and later by Davies. The methods apply a formula to the molecular weight of the whole molecule and of the hydrophilic and lipophilic portions to give an arbitrary (semi-empirical) scale up to 40 although the usual range is between 0 and 20. An HLB value of 0 corresponds to a completely hydrophobic molecule, and a value of 20 would correspond to a molecule made up completely of hydrophilic components. The HLB value can be used to predict the surfactant properties of a molecule:

| HLB Value | Expected properties |
| --- | --- |
| 0 to 3 | antifoaming agent |
| from 4 to 6 | W/O emulsifier |
| from 7 to 9 | wetting agent |
| from 8 to 18 | an O/W emulsifier |
| from 13 to 15 | typical of detergents |
| 10 to 18 | solubiliser or hydrotrope |

Although HLB numbers are assigned to surfactants other than the non-ionic, for which the system was invented, HLB numbers for anionic, cationic, and amphoteric (zwitterionic) surfactants can have less significance and often represent a relative or comparative number and not the result of a mathematical calculation. This is why it is possible to have surfactants above the "maximum" of 20. HLB numbers can however be useful to describe the HLB requirement of a desired application for a given emulsion system in order to achieve good performance.

Dried Colloid Compositions

The formulations of the invention may comprise unit solids comprising an optionally coated dried colloid composition. The dried colloid may be a dried emulsion or a dried aqueous micellar composition. The colloid in its wet liquid form comprises an aqueous phase comprising a water-soluble polymer and, dispersed therein, a liquid water-immiscible phase. The liquid water-immiscible phase may also be referred to herein as the dispersed phase. In the dry form, the water-soluble polymer forms a polymeric matrix containing other components of the dried colloid composition. For convenience, the dried aqueous phase may be referred to as e.g. the "aqueous phase", the "matrix phase" or the "polymer phase".

Hydrophilic Surfactants for the Aqueous Phase

In embodiments of the invention, the unit solid comprises a hydrophilic surfactant which, without being bound by theory, is believed at least partially to partition in the aqueous phase (polymer matrix). In a typical manufacturing process, the hydrophilic surfactant and other hydrophilic constituents of the colloid are combined with the water to form an aqueous premix, which is then combined with a premix of the constituents of the water-immiscible phase of the colloid to form the liquid colloid.

Surfactants for such inclusion in the aqueous phase are preferably readily diffusing or diffusible surfactants to facilitate manufacturing and processing of the composition of the invention. The surfactant may have an HLB of at least 10 and optionally of at least 15, e.g. at least 30 and optionally of 38-42, e.g. 40. Such surfactants can be of any particular type (cationic, anionic, non-ionic, zwitterionic) and may comprise as a proportion of dry weight of the composition from 0.1% to 6%, e.g. 0.1% to 5%. 0.1% to 4% or 0.1% to 3%, e.g. in a proportion of at least 1% and in particular between 1.0 and 4.5 or 5%, for example within or just outside the 2-4% range, for example from 2 to 3% or approximately 2% or approximately 4%. The invention includes formulations in which the hydrophilic surfactant is, or comprises, an anionic surfactant, e.g. a single anionic surfactant or a mixture thereof. Therefore, the hydrophilic surfactant may be an anionic surfactant.

Unless otherwise stated or required, all percentages and ratios are by weight.

Preferred anionic surfactants for inclusion in the aqueous phase include perfluoro-octanoate (PFOA or PFO), perfluoro-octanesulfonate (PFOS), sodium dodecyl sulfate (SDS), ammonium lauryl sulfate, and other alkyl sulfate salts, sodium laureth sulfate, also known as sodium lauryl ether sulfate (SLES) and alkyl benzene sulfonate. A particular class of surfactant comprises sulfate salts. A preferred anionic surfactant in the aqueous phase is SDS. A single anionic surfactant may be included in the aqueous phase or a combination of anionic surfactants.

The physical form of the surfactant at the point of introduction into the aqueous phase during preparation plays a role in the ease of manufacture of the composition according to the invention. As such, although liquid surfactants can be employed, it is preferred to utilize a surfactant which is in solid form (e.g. crystalline, granules or powder) at room temperature, particularly when the aqueous phase comprises gelatin.

Possible non-ionic surfactants for the aqueous phase include perfluorocarbons, polyoxyethyleneglycol dodecyl ether (e.g. Brij such as, for example, Brij 35), Myrj (e.g. Myrj 49, 52 or 59), Tween 20 or 80 (also known as Polysorbate). Brij, Myrj and Tween products are available commercially from Croda.

In general, mixtures of surfactants can be utilised e.g. to achieve optimum long term stability of the composition of the invention with shorter chain surfactants in general facilitating shorter term stability (an aid to processing) and longer chain surfactants facilitating longer term stability (an aid to shelf life). In some embodiments, shorter chain surfactants have up to $C_{10}$ alkyl (e.g. $C_6$-$C_{10}$ alkyl) as the hydrophobic portion of the surfactant whilst longer chain surfactants have $C_{10}$ or higher alkyl (e.g. $C_{10}$-$C_{22}$ alkyl) as the hydrophobic portion of the surfactant. It is envisaged that $C_{10}$ alkyl surfactants may facilitate processing or facilitate prolongation of shelf life, or both, depending on the identity of the other excipients and of the active principle(s). Higher alkyl may in particular implementations of the invention be $C_{11}$-$C_{22}$ or $C_{12}$-$C_{22}$ alkyl, and in some embodiments has a length of no greater than $C_{18}$.

Instead of (or as complement to) the surfactant in the aqueous phase, the invention also contemplates use of surfactant-like emulsifiers (also known as crystallisation inhibitors) such as, for example, HPMC (also known as hypromellose) although their use is generally contemplated in relatively smaller amounts to avoid high viscosity which may constrain processing options.

Other non-ionic surfactants which may be included in the aqueous phase include poloxamers which are non-ionic triblock copolymers composed of a central hydrophobic chain of polyoxypropylene (poly(propylene oxide)) flanked by two hydrophilic chains of polyoxyethylene (poly(ethylene oxide)). Poloxamers are available commercially under the trade name Pluronics™. Such surfactants or similar larger polymeric surfactants are aqueously soluble and are therefore presented here as optional components of the aqueous phase. However, they may be used to reduce the amount of or to replace a higher HLB polymeric component of the oil phase (see also separate section) such as, for example, polyethoxylated castor oils (polyethylene glycol ethers) exemplified commercially as Cremophor™. Diblock, tetrablock, multiblock, etc copolymers (poloxomers) are also included.

Another type of polymeric aqueous soluble surfactant which may be used in a similar way are anionic copolymers based on methacrylic acid and methyl methacrylate in which the ratio of the free carboxyl groups to ester groups is approx. 1:1 and with average molecular weight is approx. 135,000. Such a polymeric surfactant is available from Degussa under the trade name EUDRAGIT® L 100.

The surfactant included in the aqueous phase is preferably present within ranges noted above. In the minibead embodiment, avoidance of excess surfactant is desirable to avoid a "golf ball effect" whereby minibeads when dried have a plurality of point-sized dimples in their surface (visible under a microscope). While not necessarily a major concern, such dimples can lead to variability in coating if it is desired to apply for example a polymer coat to the minibeads. Although higher values within the preferred range generally increase the rate of egress/dissolution of minibeads, in certain circumstances higher levels of surfactant included in the composition may cause a counterintuitive drop in the in vitro dissolution profile including a drop in the total amount dissolved of the composition according to the invention. The concentration of surfactant above which the dissolution profile dropped (or total amount of dissolved composition dropped) may be approximately 5% by dry weight of the composition, for example when SDS is selected as the surfactant. In certain embodiments, it is therefore preferred to have in the aqueous phase a surfactant, whether non-ionic or ionic, for example anionic e.g. SDS, in an amount of less than 5% by dry weight of the total composition (for example, the composition may be in the form of beads or minibeads, wherein the aqueous phase contains SDS or another surfactant in an amount of less than 5% by dry weight of the beads/minibeads). In embodiments of the invention, the composition, e.g. in the form of beads or minibeads, comprises in the aqueous phase surfactant in an amount of no more than 5%, no more than 4.5%, no more than 4% or no more than 3% by dry weight of the beads or minibeads. In one class of embodiments, the surfactant is in an amount of at least 0.1% by dry weight of the beads or minibeads. In another class of embodiments, the surfactant is in an amount of at least 1% by dry weight of the beads or minibeads. In a further class of embodiments, the surfactant is in an amount of at least 2% by dry weight of the beads or minibeads. Higher levels of surfactant in the aqueous phase (e.g. above 5% by weight of the total composition) restrict the processing parameters for manufacturing when certain manufacturing approaches are followed.

It is noteworthy that surfactants are used in dissolution testing media when complete dissolution of the composition being studied is otherwise not achievable. In respect of the amount of surfactant included in the aqueous phase of the composition of the present invention as described above, it has been found that such (small) quantities included in the composition have a much greater effect than larger quantities included in the dissolution medium.

In the case of the minibead embodiment, the present inventors hypothesise that the local concentration of surfactant in and around the minibead as it dissolves or disperses is more effective than an otherwise greater concentration in the medium as a whole. It is also believed, although the inventors/applicants do not necessarily intend to be bound by this or other hypotheses advanced in this text, that the surfactant in the beads assists egress of active agent from within the polymer coat (if a coat is afterwards added to the minibeads) and also possibly to shield the active agent from crystallisation and/or precipitation after release from the bead.

In certain embodiments complete or substantially complete dissolution of steroid in USP/EP/JP etc dissolution apparatus using standard media can be achieved, using no or only minor amounts of surfactant in the dissolution medium, by incorporating into the formulation (e.g. dosage form) one or more surfactants even when the quantity of surfactant incorporated into the formulation is much smaller than would have been required in the medium to achieve a comparable degree of dissolution of a formulation containing no surfactant. The one or more surfactants may be comprised in the aqueous phase (the polymer matrix) or the oil phase, or both, and are in particular comprised in at least the aqueous phase and optionally also in the oil phase.

These observations are particularly relevant to the class of minibead embodiments of the invention, in particular where an oil-soluble active agent is incorporated in an oil phase or surfactant (self-assembly structure) phase and the minibead comprises a surfactant, e.g. in at least the aqueous phase (polymer matrix). On full dissolution of the composition of the invention in standard 900-1000 mL dissolution pots using compendial medium, the concentration of surfactant in an exemplary embodiment would be of the order of 0.001% i.e. much lower than the amount (around 0.5%-1%) typically added to the dissolution medium. Putting it another way, very significantly greater amounts of surfactant would need to be included in this embodiment of the composition of the invention in order to achieve a fully diluted equivalent concentration of surfactant typically used in 900-1000 mL dissolution pots.

High surfactant concentrations in the dissolution medium can generate very good in vitro data but which is not necessarily predictive of in vivo performance (e.g. pharmacokinetic profile). In contrast, incorporation of (much lower overall quantities of) surfactant in one embodiment of the minibeads of the invention produces unexpectedly superior in-vivo performance. The inventors/applicants hypothesise (without wishing to be bound by the hypothesis) that surfactant in the dissolution medium is more playing the role of a dispersing agent (bringing other components into the dissolution medium) rather than its classical role as an aid to dissolution and that it is the surfactant included in the aqueous phase of this embodiment of the composition of the invention which ensures or enables dissolution. In this setting, the small amount of surfactant included in the dissolution medium therefore makes the test more a dispersion test than a dissolution test and achieves dissolution/dispersion maintenance for the purposes of compendial methods.

Surfactants for the Hydrophobic Phase

The formulations mentioned in this specification may comprise a water-immiscible phase, hydrophobic phase or oil phase which may comprise the steroid(s). The water-immiscible phase, where present, may also include surfactant more hydrophobic than that chosen for the aqueous phase, e.g. a non-ionic surfactant. The surfactant usually has an HLB value of at least 10 but, in any event, less than that of the hydrophilic surfactant. The non-ionic surfactant typically comprises a poly(oxyethylene) group, e.g. comprises a glycerol polyethylene glycol ricinoleate.

Examples include polyethoxylated castor oils (polyethylene glycol ethers) which can be prepared by reacting ethylene oxide with castor oil. Commercial preparations may also be used as the surfactant e.g. those commercial preparations which contain minor components such as, for example, polyethylene glycol esters of ricinoleic acid, polyethylene glycols and polyethylene glycol ethers of glycerol. The preferred example is Cremophor by BASF Corp. also known as Cremophor EL. Alternative or additional surfactants include phospholipids such as, for example, phosphatidylcholine. In embodiments of the composition of the invention which comprise a phospholipid surfactant, the phospholipid surfactant may be incorporated either in the aqueous phase or in the oil phase or both. If at least one phospholipid surfactant is incorporated in each phase, it may be the same phospholipid surfactant in both phases or different in each.

The HLB of the surfactant for the water-immiscible phase, where present, may be from 10-20, e.g. 10-15, and optionally 11-20 (preferably 11-15).

The Dispersed Phase: The Hydrophobic Phase (Oil Phase)

The hydrophobic phase may comprise an oil. Such oil may itself be the continuous phase of a water-in-oil emulsion.

Any pharmaceutically suitable oil may be used to constitute a hydrophobic phase (oil drops, in this case), optionally in combination with one or more other oil-miscible and/or oil-soluble excipients. In terms of dry weight of the composition of the invention, the oil phase generally comprises a proportion from 10% to 85%, preferably 15% to 50%, more preferably 20% to 30% or from 35% to 45% e.g. for vaccine formulations. The term "oil" means any substance that is wholly or partially liquid at ambient temperature or close-to-ambient temperature e.g. between 10° C. and 40° C. or between 15° C. and 35° C., and which is hydrophobic but soluble in at least one organic solvent. Oils include vegetable oils (e.g. neem oil), petrochemical oils, and volatile essential oils. The hydrophobic phase in particular comprises a liquid lipid, e.g. a liquid composition comprising triglycerides and/or diglycerides, for example medium chain ($C_6$, $C_7$, $C_8$, $C_8$, $C_9$, $C_{10}$, $C_{11}$ or $C_{12}$) diglycerides or triglycerides or combinations thereof.

Oils which may be included in the oil phase include poly-unsaturated fatty acids such as, for example, omega-3 oils for example eicosapentanoic acid (EPA), docosohexaenoic acid (DHA), alpha-linoleic acid (ALA), conjugated linoleic acid (CLA). Preferably ultrapure EPA, DHA or ALA or CLA are used e.g. purity up to or above 98%. Omega oils may be sourced e.g. from any appropriate plant e.g. sacha inchi. Such oils may be used singly e.g. EPA or DHA or ALA or CLA or in any combination. Combinations of such components including binary, tertiary etc combinations in any ratio are also contemplated e.g. a binary mixture of EPA and DHA in a ratio of 1:5 available commercially under the trade name Epax 6000.

Oils which may be included in the oil phase are particularly natural triglyceride-based oils which include olive oil, sesame oil, coconut oil, palm kernel oil. Oils which are particularly preferred include saturated coconut and palm kernel oil-derived caprylic and capric fatty acids and glycerin e.g. as supplied under the trade name Miglyol™ a range of which are available and from which one or more components of the oil phase of the invention may be selected including Miglyol™ 810, 812 (caprylic/capric triglyceride); Miglyol™ 818: (caprylic/capric/linoleic triglyceride); Miglyol™ 829: (caprylic/capric/succinic triglyceride; Miglyol™ 840: (propylene glycol dicaprylate/dicaprate). Note that Miglyol™ 810/812 differ only in $C_8/C_{10}$-ratio and because of its low $C_{10}$-content, the viscosity and cloud point of Miglyol™ 810 are lower. The Miglyol™ range is available commercially from Sasol Industries. As noted above, oils which may be included in the oil phase need not necessarily be liquid or fully liquid at room temperature.

Waxy-type oils are also possible: these are liquid at manufacturing temperatures but solid or semi-solid at normal ambient temperatures. The oil phase may therefore be a solid or semi-solid wax phase at normal ambient temperatures.

Alternative or additional oils which may be included in the oil phase according to the invention are medium chain triglyceride compositions such as for example Labrafac™ Lipophile manufactured by Gattefosse in particular product number WL1349. Miglyol™ 810, 812 are also medium chain triglyceride compositions. The medium chain triglyceride(s) mentioned herein are those which comprise one or more triglycerides of at least one fatty acid selected from fatty acids having 6, 7, 8, 9, 10, 11 or 12 carbon atoms, e.g. $C_8$-$C_{10}$ fatty acids.

Other possible (alternative or additional) oils include linoleoyl macrogolglycerides (polyoxylglycerides) such as, for example, Labrafil (e.g. product number M2125CS by Gattefosse) and caprylocaproyl macrogolglycerides such as, for example, Labrasol by Gattefosse.

In one embodiment of the invention, the oil phase comprises more than one component. For example, as just mentioned, the oil phase may comprise a surfactant.

Within this preferred embodiment, it is further preferred that the HLB of the oil be in the range 0-10 (optionally 1-8, e.g. 1-6 and sometimes 1-5) and the HLB of the surfactant be in the range 10-20 and optionally 11-20 (preferably 11-15).

Particularly preferred oils in the lower HLB category include medium chain triglycerides, linoleoyl macrogolglycerides (polyoxylglycerides), caprylocaproyl macrogolglycerides and caprylic/capric triglyceride. In terms of commercial products, particularly preferred oils in the lower HLB range are Labrafac™ Lipophile (e.g. 1349 WL), Labrafil, Labrasol, Captex 355 and Miglyol 810.

Particularly preferred surfactants in the higher HLB category include polyethoxylated castor oils (polyethylene glycol ethers). The preferred commercial product for example is Cremophor.

While higher HLB surfactants can be considered surfactants, the invention also contemplates, additionally or alternatively, inclusion of any other appropriate (non-ionic or other) surfactant in the oil phase.

For certain active principles, particularly hydrophobic/lipophilic agents such as cyclosporin A for example, the present inventors/applicants have observed to their surprise that incorporation into the oil phase of a surfactant of high HLB and an oil of low HLB in a ratio of 1-4:1 by weight, e.g. 1.2-3.0:1 by weight, preferably 1.5-2.5:1 by weight and most preferably 1.8-2.2:1 by weight (high HLB: low HLB) advantageously stabilizes the emulsion before and after immobilization of the oil droplets in the aqueous phase. In this context "stabilize" means in particular that the embodiment improves dissolution and/or dispersion of the composition in vitro.

By "high" HLB in this context is generally intended above 10, preferably from 10-16, e.g. from 12 and 16 or 12 to 14. By "low" HLB is generally intended below 10, preferably in the range 1 to 4, more preferably 1 to 2.

The oil phase may also comprise a solvent, miscible with the oil, for the active principle. The oil phase may therefore comprise a liquid lipid and a solvent miscible therewith, in which solvent the water-insoluble active ingredient is soluble. The solvent for the active principle may be miscible with both the liquid lipid and with water.

Examples of suitable solvents are 2-(2-ethoxyethoxy) ethanol available commercially under trade names Carbitol™, Carbitol cellosolve, Transcutol™, Dioxitol™, Polysolv DE™, and Dowanal DE™; or the purer Transcutol™ HP (99.9). Transcutol P or HP, which are available commercially from Gattefosse, are preferred. Another possible co-solvent is poly(ethylene glycol). PEGs of molecular weight 190-210 (e.g. PEG 200) or 380-420 (e.g. PEG 400) are preferred in this embodiment. Suitable PEGs can be obtained commercially under the name "Carbowax" manufactured by Union Carbide Corporation although many alternative manufacturers or suppliers are possible.

A particularly preferred oil phase according to the invention is made up of an oil (low HLB), a surfactant (high HLB) and a solvent for the active principle. The oil may be a liquid lipid e.g. an MCT composition. For example the following three commercial products: Transcutol P (as solvent), Miglyol 810 (as oil) and Cremophor e.g. Cremophor EL (as surfactant) is particularly preferred. Miglyol 810 has a low HLB and Cremophor has a high HLB. This particularly preferred oil phase is preferably used to prepare (and is preferably a component of) a composition of the invention comprising cyclosporin. In one embodiment, the composition comprises an oil-soluble or hydrophobic antioxidant e.g. hydralazine or BHT or carnosic acid or vitamin E.

The oil phase may also be a water-in-oil (w/o) emulsion so that the composition of the invention becomes a water-in-oil-in-water (w/o/w) emulsion.

The oil phase may include a steroid (i.e. at least one steroid) and/or one or more other active principles and may also include one or more volatile or non-volatile solvents, which may be the same as or different from the solvent or oil phase surfactant previously mentioned. Such solvents may for example remain in the composition of the invention following processing e.g. initial dissolution of the active principle, and have no particular function in the final composition. Alternatively, such solvents if present may function to maintain the steroid active principle in a dissolved state (in solution) within the oil phase or to facilitate dispersion, egress etc. In other embodiments, the solvent may have partly or fully evaporated during processing and therefore be present in only minor quantities if at all. In a related embodiment, the solvent, particularly when a solvent which is both oil and water-soluble is used, may be partly or completely present in the aqueous phase of the composition according to the invention. An example of such a solvent is ethanol. Another example is Transcutol which is already mentioned as a solvent.

It will be appreciated, therefore, that the invention provides inter alia a bead or minibead comprising a water-soluble polymer matrix material in which are dispersed droplets of oil, the composition comprising a steroid and the oil optionally comprising a combination of a high HLB compound, e.g. a surfactant, and a low HLB compound, e.g. an oil, and optionally including a solvent.

The oil droplets in the aqueous phase in its wet state during manufacture may be small enough (e.g. <100 nm) not to refract light, hence forming a transparent dispersion. This is termed a microemulsion, as is well known in the art.

The Dispersed Phase: The Self-Assembly Phase

As an alternative to an oil or wax phase as described above, the dispersed phase of the colloidal formulations of the invention may comprise self-assembly structures, e.g. micelles, vesicles, liposomes or nanoparticles, or at least the structures which result from drying aqueous colloids comprising such types of self-assembly structures. The invention in particular includes formulations in which the dispersed phase is micellar, i.e. formed of micelles and/or promicelles. The term "promicelle" refers to a part of a formulation which will form a micelle upon contact with water, e.g. gastrointestinal contents.

A self-assembly structure-forming surfactant is present as self-assembly structures dispersed within the hydrogel-forming polymer in a "wet" (not yet dried) composition made as an intermediate in the manufacturing process described herein. It is believed also to be present as self-assembly structures in the dried composition but observability of self-assembly structures in the dried composition is not a requirement of the invention. It is mentioned at this point that the presence of a surfactant in self-assembly structure form does not require that the entire surfactant content of a composition is in self-assembly structure form as it is considered more probable that a portion of the surfactant will be outside the self-assembly structures. Thus in the "wet" composition, whether the hydrogel-forming polymer is in the gel state or the sol (liquid) state it may comprise a micelle-forming surfactant at a concentration above the critical micelle concentration.

The diameter of the dispersed self-assembly structures may be between 0.5 nm and 200 nm, 1 nm and 50 nm, or 5 nm and 25 nm. The size of the self-assembly structures may be determined by dynamic light scattering or diffusion NMR techniques known within the art. Although the size of the self-assembly structures is given as a diameter this does not imply that the self-assembly structures must be purely spherical species only that they may possess some approximately circular dimension.

The self-assembly structure-forming surfactant may be, or comprise, a non-ionic surfactant. The surfactant may be a polyoxyethylated surfactant. The surfactant has a hydrophilic head which may be a hydrophilic chain, for example a polyoxyethylene chain or a polyhydroxylated chain.

The surfactant of course has a hydrophobic part and in particular a hydrophobic chain. The hydrophobic chain may be a hydrocarbon chain, for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ hydrocarbon chains. It may be an alkyl chain, e.g. having a number of carbon atoms just mentioned. It may be an alkenyl chain comprising one or more carbon-carbon double bonds, e.g. having a number of carbon atoms just mentioned. The surfactant may comprise a hydrocarbon chain, e.g. alkyl chain or alkenyl chain, that is substituted provided that it maintains a hydrophobic characteristic. There may for example be one or two substituents, for example a single substituent, e.g. selected from halogen (e.g. F or Cl), hydroxy, thiol oxo, nitro, cyano; hydroxy or thiol substituents may be esterified by for example a fatty acid. One class of surfactants comprise a hydrocarbon monosubstituted by hydroxy; optionally, at least a portion of the hydroxy groups of an aliquot of surfactant, e.g. of the surfactant in a bead, may be esterified by a fatty acid or mono-hydroxy fatty acid as disclosed herein or etherified by a fatty alcohol for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ fatty alcohols.

The hydrophobic chain may be part of an esterified fatty acid $R^1$—COOH or of an etherified or esterified fatty ether $R^1$—COH where $R^1$ is the hydrophobic chain, e.g. as mentioned in the preceding paragraph. The ester-forming or, as the case may be, ether-forming group will typically comprise a hydrophilic chain.

As mentioned, the surfactant may have a hydrophilic chain and may be a non-ionic surfactant, and may satisfy both requirements. The hydrophilic chain may be a poly(ethyleneglycol), also known as poly(oxyethylene) or macrogol. The hydrophilic chain may be of the formula —(O—$CH_2$—$CH_2$)$_n$—OR where n is 5 or 6 to 50 and R is H or alkyl, e.g. ethyl or methyl. The invention includes implementations in which n is from 6 to 40, e.g. from 6 to 35. In some embodiments, n is from 6 to 25 and optionally is from 8 to 25 or from 8 to 15. In other embodiments, n is from 8 to 50 or from 8 to 40, e.g. is from 10 to 50, 10 to 40 or 10 to 35. In a particular embodiment, n is 15. For all hydrophilic chains of the formula —(O—$CH_2$—$CH_2$)$_n$—OR, in one class of embodiments R is H.

The hydrophilic chain may be a polyhydroxylated chain (for example a $C_5$-$C_{20}$ e.g. $C_5$-$C_{10}$ chain), e.g. having a hydroxy group on the carbon atoms of the chain, for example a glucamide.

The self-assembly structure-forming surfactant may comprise a combination of a hydrophobic chain as described above and a hydrophilic chain as described above. It may therefore be, or comprise, a macrogol ester of a fatty acid as described herein or a macrogol ether of a fatty alcohol as described herein.

Self-assembly structure-forming surfactants comprising a hydrophobic chain and a hydrophilic chain can be selected from the group consisting of: macrogol esters; macrogol ethers; diblock copolymers; triblock copolymers; and amphiphilic polymers. In certain embodiments of the invention any combinations of the group are included within the invention.

Examples of macrogol esters which are suitable for use in the present invention are macrogol esters of fatty acids having at least 6 carbon atoms and optionally at least 10 carbon atoms, and particularly of at least 12 carbon atoms; some fatty acids have no more than 22 carbon atoms, for example $C_{10}$-$C_{20}$, $C_{12}$-$C_{20}$ or $C_{15}$-$C_{20}$ fatty acids. The fatty acids may be saturated or unsaturated but are in particular saturated. To be mentioned are macrogol 25 cetostearyl ether (Cremophor® A25); macrogol 6 cetostearyl ether (Cremophor® A6); macrogol glycerol ricinoleate 35 (Cremophor® EL); macrogol-glycerol hydroxystearate 40 (Cremophor® RH 40); macrogol-15-hydroxystearate (Kolliphor® HS 15, previously known as Solutol® HS 15). Examples of macrogol ethers which are suitable for use in the present invention are macrogol ethers of fatty alcohols having at least 6 carbon atoms and optionally at least 10 carbon atoms, and particularly of at least 12 carbon atoms; some fatty alcohols have no more than 22 carbon atoms, for example $C_{10}$-$C_{20}$, $C_{12}$-$C_{20}$ or $C_{15}$-$C_{20}$ fatty alcohols. The fatty alcohols may be saturated or unsaturated but are in one embodiment saturated.

Examples of amphiphilic polymers which are suitable for use in the present invention are: alkyl glucamides; fatty alcohol poly(ethoxyl)ates also known as polyethoxylated alkyl ethers; poly(ethoxyl)ated fatty acid esters (Myrj or Kolliphor® HS 15); fatty amide polyethoxylate; fatty amine ethoxylate; alkylphenol ethoxylate; polyethoxylated sorbitan esters (polysorbates); polyethoxylated glycerides; or poly-glycerol esters.

Examples of copolymers, which are suitable for use in the present invention are: pluronics(poloxamers); polyvinylpyrrolidone-polyvinylacetate (Plasdone S630); aminoalkyl methacrylate copolymer (Eudragit EPO); methacrylic acid-methyl methacrylate copolymer (Eudragit S100, L100); polycaprolactone-PEG; polycaprolactone-methoxy-PEG; poly(aspartic acid)-PEG; poly(benzyl-L-glutamate)-PEG; poly(D,L-lactide)methoxy-PEG; poly(benzyl-L-aspartate-PEG; or poly(L-lysine)-PEG In a preferred embodiment the self-assembly structure-forming surfactant is a macrogol ester, more preferably a macrogol ester that conforms to the European Pharmacopoeia monograph number 2052 macrogol-15-hydroxystearate, such as Kolliphor® HS 15 marketed by BASF.

Suitable surfactants comprise those which during manufacture combine with the aqueous phase (including hydrogel-forming polymer) in an amount above their CMC to form a clear liquid. Kolliphor® HS 15 is such a surfactant.

In certain embodiments the weight ratio of the self-assembly structure-forming surfactant to the antigen is from 10:1 to 100:1, optionally from 50:1 to 100:1. In some embodiments, the ratio is from 80:1 to 90:1. In particular embodiments, the ratio is from 50:1 to 60:1.

In particular embodiments, the compositions of the invention comprise a combination of self-assembly structure-forming compounds. Such a combination of self-assembly structure-forming compounds may consist of two or more surfactants as mentioned in the preceding section of this specification. Alternatively, a surfactant may be combined with one or more other compounds at least potentially able to form self-assembly structures with the surfactant, optionally selected from cationic lipids and glycolipids, amongst others. As an additional option, a composition may comprise a plurality of surfactants as mentioned in the preceding section of this specification and one or more other compounds at least potentially able to form self-assembly structures with the surfactant, optionally selected from cationic lipids and glycolipids, amongst others.

The invention therefore includes compositions as described herein which comprise:

- two or more self-assembly structure-forming surfactants, e.g. two or more surfactants having a hydrophobic chain and a hydrophilic chain
- a compound, e.g. a single compound or two or more compounds, selected from cationic lipids and glycolipids
- two or more self-assembly structure-forming surfactants and a compound, e.g. a single compound or two or more compounds, selected from cationic lipids and glycolipids The Aqueous Phase The principal component of the aqueous phase of the dried colloidal formulations according to the invention (preferably between 20% and 70%, more preferably between 30% and 60%, still more preferably between 35% and 55%, by dry weight thereof) is a water-soluble polymer matrix material although other components may also be included as described below. The inclusion of too little of the water-soluble polymer matrix material can for certain active principles lead to non-incorporation or leaching of the active out of the composition, particularly when in the form of minibeads. For certain embodiments, for example micellar compositions, e.g. comprising Kolliphor® HS 15, or those comprising a retardant (see below), it is preferred that the water-soluble polymer matrix material constitute from 55% and 65% of the dry weight of the composition.

While mixtures of water-soluble polymer matrix materials are contemplated by the invention, the matrix material may be substantially a single material or type of material among those described herein. Where the matrix material is a single type of material, that type may be thermotropic hydrogel-forming polymers; for example, a combination of such polymers may be used. However, mixtures may be preferred to achieve certain performance characteristics. Thus it may be desired to incorporate certain controlled release or retarding substances (retardants) into the water-soluble polymer matrix. In certain embodiments, such incorporation permits a coat (or coating) to be dispensed with. In other embodiments where a controlled release or retarding agent is included into the water-soluble polymer matrix, a coat (or coating) may be present and desirable. For example, incorporation of a retarding agent which is insoluble in acid milieu (such as the stomach) is selected to prevent or retard release in the stomach and a coating may not be needed i.e. the composition may be free of a coat/coating. Alternatively, incorporation of a retarding agent which is soluble in acid media may be selected to retard release in the intestine distal to the stomach. Again a coating may not be needed i.e. the composition may be free of a coat/coating. However, a composition according to the invention which incorporates a retarding agent soluble in acid media may optionally be coated e.g. with an acid-resistant polymer to achieve particular advantage. Such a composition is protected from (complete) gastric release (or gastric release is retarded) owing to the effect of the acid-resistant polymer coat. Distal to the stomach, following loss of the coat, the acid-soluble agent retards release because the milieu of the small and large intestine is no longer acid. Retarding or controlled release agents insoluble in acid milieu include polymers whose solubility is pH-dependent i.e. soluble at higher pH. Such polymers are described in detail in the section below entitled “Coating” and such polymers may be used either as coats/coatings or as retarding agents or controlled release agents incorporated into the water-soluble polymer matrix. An example of a suitable retarding agent mentioned in the section below entitled “Coating” is HPMCP (hydroxy-propyl-methyl-cellulosephthalate also known as hypromellose phthalate) which is used to prevent release in the gastric environment since it is soluble above pH 5.5—see that section for other examples of polymers soluble in non-acid (basic) media. HPMCP may also be used as a pore-former. Retarding or controlled release agents soluble in acid milieu include polymers whose solubility is pH-dependent i.e. soluble at lower pH. Such polymers include cationic polymers such as for example copolymers based on dimethylaminoethyl methacrylate, butyl methacrylate, and methyl methacrylate. An example of such a cationic co-polymer which may be used according to the invention is Eudragit E PO commercially available from Evonik Industries.

In one embodiment, the water-soluble polymer matrix material may be of one or more of (e.g. two of) those selected from gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, hydroxypropylmethyl cellulose, polymerisates of acrylic or methacrylic esters and polyvinylacetate-phthalate and any derivative of any of the foregoing. If a single polymer material is used, it may be gelatin. If a mixture of polymer materials is used, the mixture may comprise gelatine, e.g. in combination with one or more members of the list earlier in this paragraph. In specific embodiments binary or tertiary etc combinations of any of the above substances are foreseen. An advantage of combining certain water-soluble polymers, e.g. gelatin and agar, to form the matrix is that it allows for a reduction in the total amount of water-soluble polymer employed. This may have cost advantages or may allow greater loading of other materials such as, for example, one or more active principles. Inclusion of (addition of) a second water-soluble polymer to form the matrix may also give more strength to the composition of the invention e.g. beads.

In a preferred embodiment, the polymer matrix material is a hydrocolloid i.e. a colloid system wherein the colloid particles are dispersed in water and depending on the quantity of water available can take on different states, e.g., gel or sol (liquid). It is preferred to use reversible hydrocolloids (e.g. agar, gelatin etc) as opposed to irreversible (single-state) hydrocolloids. Thermotropic hydrocolloids (also known as thermoreversable hydrocolloids) can exist in a gel and sol state, and alternate between states with the addition or elimination of heat. Gelatin is a thermo-reversible, rehydratable colloid and is particularly preferred. Gelatin derivatives such as, for example, succinated or phthalated gelatins are also contemplated. Hydrocolloids which may be used according to the invention include those derived from natural sources such as, for example, carrageenan (extracted from seaweed), gelatin (extracted from bovine, porcine, fish or vegetal sources), agar (from seaweed) and pectin (extracted from citrus peel, apple and other fruits). A non-animal based hydrocolloid may be preferred for certain applications e.g. administration to vegetarians or to individuals not wishing to ingest animal products for religious or health reasons. In relation to the use of carrageenan, reference is made to US patent application 2006/0029660 A1 (Fonkwe et al), the entirety of which is incorporated herein by reference.

The water-soluble polymer may therefore be gelatin. The water-soluble polymer may comprise gelatin The immobilized aqueous phase of the composition according to one embodiment of the invention is preferably a gel i.e. a substantially dilute crosslinked system, which exhibits no flow when in the steady-state. The internal network structure of the solidified aqueous phase may result from physical or chemical bonds, as well as crystallites or other junctions that remain intact within an extending fluid e.g. water.

In an alternative preferred embodiment, the polymer matrix is a non-hydrocolloid gum. Examples are the cross-linked salts of alginic acid. For example, aqueous solutions of sodium alginate gums extracted from the walls of brown algae have the well known property of gelling when exposed to di- and trivalent cations. A typical divalent cation is calcium, often in the form of aqueous calcium chloride solution. It is preferred in this embodiment that the cross-linking or gelling have arisen through reaction with such a multivalent cation, particularly calcium.

In an alternative preferred embodiment, the polymer matrix is chitosan which can exist in the form of biogels with or without additives as described e.g. in U.S. Pat. No. 4,659,700 (Johnson & Johnson); by Kumar Majeti N. V. Ravi in Reactive and Functional Polymers, 46, 1, 2000; and by Paul et al. in ST.P. Pharma Science, 10, 5, 2000 the entirety of all 3 of which is incorporated herein by reference. Chitosan derivatives e.g. thiolated entities are also contemplated.

As regards gelatin, reference is hereby made to "bloom strength", a measure of the strength of a gel or gelatin developed in 1925 by O. T. Bloom. The test determines the weight (in grams) needed by a probe (normally with a diameter of 0.5 inch) to deflect the surface of the gel 4 mm without breaking it. The result is expressed in Bloom (grades) and usually ranges between 30 and 300 Bloom. To perform the Bloom test on gelatin, a 6.67% gelatin solution is kept for 17-18 hours at 10° C. prior to being tested.

Where the polymer matrix comprises gelatin, e.g. is gelatin, it is preferred to use gelatin with bloom strength between 200 and 300, preferably between 210 and 280.

Where the polymer matrix comprises gelatin, e.g. is gelatin, the gelatin may be obtained from a variety of sources. For example, it can be obtained by the partial hydrolysis of collagenous material, such as the skin, white connective tissues, or bones of animals. Type A gelatin is derived mainly from porcine skins by acid processing, and exhibits an isoelectric point between pH 7 and pH 9, while Type B gelatin is derived from alkaline processing of bones and animal (bovine) skins and exhibits an isoelectric point between pH 4.7 and pH 5.2. Type A gelatin is somewhat preferred. Gelatin for use in the invention may also be derived from the skin of cold water fish. Blends of Type A and Type B gelatins can be used in the invention to obtain a gelatin with the requisite viscosity and bloom strength characteristics for minibead manufacture.

Commercially gelatin can be obtained from the Sigma Chemical Company, St. Louis, Mo. USA or from Nitta (http://www.nitta-gelatin.com).

Lower temperature gelatin (or gelatin derivatives or mixtures of gelatins with melting point reducers) or other polymer matrices able to be solidified at lower temperatures (e.g. sodium alginate described above) are preferred for example when the active principle to be incorporated in the composition of the invention is temperature-labile or whose activity may be affected by exposure to higher temperatures.

Where the polymer matrix comprises gelatin, e.g. is gelatin, the starting gelatin material is preferably modified before manufacture to produce "soft gelatin" by the addition of a plasticizer or softener to the gelatin to adjust the hardness of the composition of the invention. The addition of plasticizer achieves enhanced softness and flexibility as may be desirable to optimise dissolution and/or further processing such as, for example, coating. Useful plasticizers of the present invention include glycerin (1,2,3-propanetriol), D-sorbitol (D-glucitol), sorbitol BP (a non-crystallizing sorbitol solution) or an aqueous solution of D-sorbitol and sorbitans (e.g. Andidriborb 85/70). Other or similar low molecular weight polyols are also contemplated. Polyethylene glycol may also be used although this is less preferred and indeed particularly preferred compositions of the invention are free or substantially free of PEG or derivatives thereof. Glycerin and D-sorbitol may be obtained from the Sigma Chemical Company, St. Louis, Mo. USA or Roquette, France.

As noted above, some constituents of the present invention may play more than one role. For example when one of the active principles (see below) is ibuprofen, it may also act as a plasticiser owing to its particular physico-chemical properties. Choice of ibuprofen has particular advantages in relation to higher loading as "conventional" plasticiser, for example dibutyl sebacate or DBS, may be reduced in quantity. Alternatively it is contemplated that the surfactants discussed above may be selected for their plasticiser characteristics to achieve particular advantage.

Softeners, if utilized, can be ideally incorporated in a proportion rising to 30%, preferably up to 20% and more preferably up to 10% by dry weight of the composition of the invention, even more preferably between 3 and 8%, and most preferably between 4% and 6%.

As noted in more detail above in the section on surfactants, it is preferred to include one or more surfactants in the aqueous phase. Certain surfactants may also act as plasticisers or softeners or vice versa.

Although not essential, the aqueous phase may also optionally contain a disintegrant where it is particularly desired to enhance the rate of disintegration of the composition of the invention.

Examples of disintegrants which may be included are alginic acid, croscarmellose sodium, crospovidone, low-substituted hydroxypropyl cellulose and sodium starch glycolate.

A crystallisation inhibitor (e.g. approximately 1% by dry weight of the composition) may also be included in the composition of the invention, preferably in the aqueous phase. An example is hydroxy propyl/methyl cellulose (HMC or HPMC, hypromellose etc) which may play other roles such as, for example, emulsifier (see above). In addition, the aqueous phase may include some or all of a solvent used during processing to dissolve, or facilitate dissolution of, an active principle e.g. an active principle comprised in the oil phase. An example is ethanol (see discussion above on use of solvents in oil phase).

The invention includes compositions comprising a solid phase comprising a water-soluble polymer matrix material and an oil phase dispersed in the solid phase.

Shape, Size and Geometry of Dried Colloidal Formulations

The dried colloidal compositions (i.e. those obtainable by drying a colloid can be formed into a limitless number of shapes and sizes. In the section below describing the process for making the composition, various methods are given including pouring or introducing a fluid emulsion into a mould where it hardens or can be caused to harden. Thus the composition can be created in whichever form is desired by creating an appropriate mould (e.g. in the shape of a disc, pill or tablet). However, it is not essential to use a mould. For example, the composition may be in the form of a sheet e.g. resulting from pouring a fluid emulsion onto a flat surface where it hardens or can be caused to harden.

Alternatively, the composition may be in the form of spheres or spherical-like shapes made as described below. Preferably, the composition of the invention is in the form of spherical, seamless beads, especially minibeads. (It will be understood that the terms "sphere" and "spherical" as applied to beads/minibeads do not refer to precise geometric spheres but to shapes which, to the human eye, approximate to spheres). The absence of seams on the minibead surface is an advantage e.g. in further processing, for example coating, since it allows more consistent coating, flowability etc. The absence of seams on the minibeads also enhances consistency of dissolution of the minibeads.

The preferred size or diameter range of minibeads according to the invention can be chosen to avoid retention in the stomach upon oral administration of the minibeads. Larger dosage forms are retained for variable periods in the stomach and pass the pyloric sphincter only with food whereas smaller particles pass the pylorus independently of food. Selection of the appropriate size range (see below) thus makes the prediction of therapeutic effect post-dosing more accurate. Compared to a single large monolithic oral format such as, for example, a traditional compressed tablet, a plurality of minibeads released into the GI tract (as foreseen by the present invention) permits greater intestinal lumen dispersion so enhancing absorption via exposure to greater epithelial area, prevents irritation (e.g. as otherwise seen with NSAIDs) and achieves greater topical coating (e.g. as may be desired for local drug effect in certain parts of the GI tract for example the colon). Reduction of residence time in the ileo-caecal junction is another advantage.

The dried colloidal composition is preferably monolithic meaning internally (i.e. cross-sectionally) homogeneous. This is particularly preferred for the minibead embodiment.

The minibeads mentioned herein generally range in diameter from 0.5 mm to 10 mm with the upper limit preferably 5 mm, e.g. 3 mm or 2.5 mm. A particularly convenient upper limit is 2 mm or 1.7 mm. The lower limit can preferably be 1 mm, e.g. 1.2 mm, more preferably from 1.3 mm, most preferably from 1.4 mm. In one embodiment the diameter is from 0.5 to 2.5 mm, for example from 1 mm to 3 mm, 1 mm to 2 mm, 1.2 mm to 3 mm or 1.2 mm to 2 mm. The minibeads may have a diameter of no more than 2.5 mm, irrespective of their minimum size. The minibeads may have a diameter of no more than 2 mm, irrespective of their minimum size.

A minibead as described herein may have an aspect ratio of no more than 1.5, e.g. of no more than 1.3, for example of no more than 1.2 and, in particular, of from 1.1 to 1.5, 1.1 to 1.3 or, 1.1 to 1.2. A population of minibeads as described herein, e.g. at least 10 minibeads, may have an average aspect ratio of no more than 1.5, e.g. of no more than 1.3, for example of no more than 1.2 and, in particular, of from 1 to 1.5, 1 to 1.3 or 1 to 1.2. The aspect ratios mentioned in this paragraph optionally apply to coated minibeads and optionally apply to uncoated minibeads. Average aspect ratio is suitably determined for a population of beads, e.g. at least 10 beads, using a particle size analyser, for example an Eyecon™ particle characteriser of Innopharma Labs, Dublin 18, Ireland.

Minibead size (diameter) may be measured by any suitable technique, for example microscopy, sieving, sedimentation, optical sensing zone method, electrical sensing zone method or laser light scattering. Minibead size is in particular measured by optical microscopy or sieving.

In embodiments, the minibeads are monodisperse. In other embodiments, the minibeads are not monodisperse. By "monodisperse" is meant that for a plurality of minibeads (e.g. at least 100, more preferably at least 1000) the minibeads have a coefficient of variation (CV) of their diameters of 35% or less, optionally 25% or less, for example 15% or less, such as e.g. of 10% or less and optionally of 8% or less, e.g. 5% or less. A particular class of polymer minibeads has a CV of 25% or less. CV when referred to in this specification is defined as 100 times (standard deviation) divided by average where "average" is mean particle diameter and standard deviation is standard deviation in particle size. Such a determination of CV is performable using a sieve.

The minibeads may have a CV of 35% and a mean diameter of 1 mm to 2 mm, e.g. 1.5 mm. The minibeads may have a CV of 20% and a mean diameter of 1 mm to 2 mm, e.g. 1.5 mm, e.g. a CV of 10% and a mean diameter of 1 mm to 2 mm, e.g. 1.5 mm. In one class of embodiments, 90% of beads have a diameter of from 0.5 mm to 2.5 mm, e.g. of from 1 mm to 2 mm.

Another possible form of the composition is as hemispherical beads two of which may optionally be joined at the flat face to create a single minibead with two distinct halves, each having a distinct composition, if that is desired, e.g. each containing different active principles or the same active principles but different excipients e.g. to achieve differing permeability, solubilization or release profiles as between the two hemispheres.

The embodiment in which the composition takes the form of minibeads can be further developed to create a larger mass of minibeads e.g. via compression (with appropriate oil or powder-based binder and/or filler known to persons skilled in the art of pharmaceutical formulation) and with the option of including additional quantities of the same active ingredient as in the composition of the invention or a different active ingredient. For example, the composition of the invention may take the form of beads which comprise an active agent or combination of active agents as disclosed herein and the binder or filler comprises an active agent mentioned previously herein in the context of combination therapy with a steroid. A compressed mass of minibeads may disintegrate at a different rate in different conditions than a unitary moulded form of the same shape. The larger (e.g. compressed) mass may itself take a variety of shapes including pill shapes, tablet shapes, capsule shapes etc. A particular problem which this version of the minibead embodiment solves is the "dead space" (above the settled particulate contents) and/or "void space" (between the particulate content elements) typically found in hard gel capsules filled with powders or pellets. In such pellet- or powder-filled capsules with dead/void space, a patient is required to swallow a larger capsule than would be necessary if the capsules contained no such dead space. The minibeads of this embodiment of the invention may readily be compressed into a capsule to adopt the inner form of whichever capsule or shell may be desired leaving much reduced, e.g. essentially no, dead/void space. Alternatively the dead or void space can be used to advantage by suspending minibeads in a vehicle such as, for example, an oil which may be inert or may have functional properties such as, for example, permeability enhancement or enhanced dissolution or may comprise an active ingredient being the same or different from any active ingredients in the bead. For example, hard gelatin capsules may be filled with a liquid medium combined with uncoated and/or coated beads. The liquid medium may be or comprise one or more of the oil phase constituents described herein or it may be one or more surfactants. Particularly preferred but non-limiting examples are corn oil and the commercial products known as Span 85, Labrafac, Transcutol P and Tween 80.

Another possible form of the dried colloidal compositions is as a capsule in which the core of the composition is a solid (e.g. gastro-retentive float material such as, for example, bicarbonate salts) or a fluid (a gas or a liquid). If the core is a liquid, it may contain an active principle and/or excipients which may be the same or different from those described above. Like the hemispherical beads described above, such capsules may have two halves of different constitution and sealed hermetically to retain the internal fluid. An internal layer e.g. internal film layer of non-aqueous material on the inner face of the sphere, may be included if it is desired that the core be an aqueous liquid such that the internal layer prevents the aqueous core from coming into contact with the inner surface of the capsule. With or without an intermediate layer, the core may be a variant of the dried colloidal compositions so that the composition of the invention, in the minibead embodiment, comprises a core made from a first composition according to the invention and a capsule made from a second composition according to the invention.

The minibead embodiment of the invention, while by itself offering a range of solutions to the issues identified above, may also be used as a starting point for creation of further e.g. pharmaceutical or forms for example by using the minibead as a seed on which additional layers of material can be applied as is well known to a person skilled in the art e.g. of pharmaceutical science. The material of the additional layers may comprise the same or different active principle and/or the same or different excipients as are described in this document. Such variants allow differential release of the same or different active principles and facilitate inclusion of multiple fixed-dose combination products as for example discussed in connection with the popularly termed "polypill" which denotes a single pill comprising more than one active principle in a fixed dose combination.

The formulations, whether or not dried colloidal formulations, may have a coat of additional material on its outer surface. This coat may be applied in a number of ways, including drug layering, as described more particularly in the section below entitled "coating". In one such embodiment, the formulation comprises an acid within the formulation, for example within a bead, e.g. included within the water-soluble polymer matrix or as a liquid core in minibead format and bicarbonate applied as a coat e.g. by drug layering. If the formulation, e.g. minibead, has a polymeric coat, e.g. to control release into the colon, the bicarbonate may optionally or additionally be included in or be absent from the coating polymer. This composition is intended to release carbon dioxide in the GI tract e.g. to reduce pain or to reduce inflammation. The formulation may comprise an acid to enhance the solubility of active principles of various pKa (acid dissociation constant) in the small intestine or colon. Alternatively, the formulation may comprise a base to enhance the solubility of active principles of various pKa in the stomach.

Other Characteristics of Dried Colloidal Formulations

The colloidal compositions, in certain embodiments, comprises one or more elements, components, excipients, structural features, functional features or other aspects of the prior art described above.

To summarise a limited number of embodiments of the invention, the composition as described above and elsewhere herein may additionally be one or more of the following: substantially water-free, in a gel state, in a solid state, undissolved, non-powdered, formed, shaped, and not in solution.

Unless geometrically designed to comprise inner aqueous compartments (e.g. w/o/w format or capsular format with liquid core), it is desirable that the colloidal formulations of the invention are essentially or substantially dry, e.g. contains less than 5%, preferably less than 1% of free water by weight. Minibeads are preferably homogeneous although processing conditions may be varied (see below) to achieve for example heterogeneity such as, for example, a harder skin and softer core with less than complete immobilization of oil droplets towards the core as opposed to the surface of the bead. Larger (e.g. non-beaded) forms or shapes of the composition according to the invention may particularly be engineered to embody such heterogeneity.

The low free-water content is a distinguishing feature of certain embodiments of the colloidal compositions i.e. dried colloidal compositions. The free-water content can be measured using thermogravimetic analysis (TGA), for example with commercially available instrumentation, e.g. using a TGA Q 500 of TA Q series instrument. TGA measures changes in weight in relation to a change in temperature. For example, a TGA method can comprise a temperature scan, e.g. from 20 to 400° C. at 20° C. per minute, where the moisture content is obtained from the sample weight loss at about 100 degrees Celsius.

In one embodiment, the dispersed phase, e.g. oil droplets is homogeneously dispersed in the solidified aqueous phase (or in some embodiments the water-soluble polymer matrix material) with substantial absence of coalescence between adjacent oil droplets. Thus the colloid is preferably maintained during solidification. Coalescence of neighbouring oil droplets or self-assembly structures, preferably only occurs, if at all, on rehydration of the composition of the invention.

Depending on process parameters, oil droplet size can vary broadly e.g. from 10 nm to 10 μm (diameter). However, the inventors/applicants have found that it is beneficial to maintain droplet size in the range from 100 nm to 1 μm, e.g. from 300-700 nm. The term "emulsion" therefore includes microemulsions and nanoemulsions.

The colloidal compositions may comprise multiple drops or droplets of water-immiscible liquid (or solid or semi-solid) within a moulded or shaped form e.g. a minibead which might typically contain many hundreds or thousands of droplets or self-assembly structures as distinct from a powder which generally derives from micron-sized particles incorporating a single or a small number of oil droplets often following coalescence of smaller droplets during spray-drying. While powder embodiments are not excluded, the composition of the invention, if particulate, preferably comprises particles larger than powder particles such that the composition is in a non-powdered form.

Where the formulation is in the form of minibeads, a plurality of minibeads may be presented in a single format e.g. contained in a single capsule, e.g. hard gel capsule, which releases the minibeads e.g. in the stomach. Alternatively the minibeads may be presented in a sachet or other container which permits the minibeads to be sprinkled onto food or into a drink or to be administered via a feeding tube for example a naso-gastric tube or a duodenal feeding tube. Alternatively, the minibeads may be administered as a tablet for example if a plurality of minibeads are compressed into a single tablet as described elsewhere herein. Alternatively, the minibeads may be filled e.g. compressed into a specialist bottle cap or otherwise fill a space in a specialised bottle cap or other element of a sealed container (or container to be sealed) such that e.g. on twisting the bottle cap, the minibeads are released into a fluid or other contents of the bottle or vial such that the beads are dispersed (or dissolve) with or without agitation in such contents. An example is the Smart Delivery Cap manufactured by Humana Pharma International (HPI) S.p.A., Milan, Italy. A related or similar approach is also contemplated for e.g. timed release of mini-capsules into a reactor, feeding environment e.g. tank, incubator etc.

The minibeads so-presented may be of a single type (or population) or may be of multiple types (or populations) differing between populations in relation to one or more features described herein e.g. different API or different excipients or different physical geometry, coated, multiply coated, uncoated etc.

In one embodiment, the invention allows for minibeads having immediate release (IR) characteristics e.g. bearing no coat, enteric-only coat or coat designed to prevent release and/or dissolution of the bead only for a limited time or lacking a retardant in the aqueous phase. In another embodiment, the invention allows for minibeads having delayed or sustained release (SR) characteristics e.g. bearing a coat (or more than one coat) as described in more detail elsewhere herein, particularly in the section entitled "coating". The invention also provides for an embodiment in which immediate release minibeads are produced in combination with a Sustained Release or Controlled Release (CR) minibeads in varying ratios of IR:SR/CR. The immediate release minibeads can be combined with a Sustained or Controlled release minibead component in the following ratios (w/w by potency) e.g. 10% Immediate Release (IR)+90% Sustained (SR)/Controlled Release (CR) minibeads; 20% IR+80% SR/CR; 30% IR+70% SR/CR; 40% IR+60% SR/CR and 50% IR+50% SR/CR.

Other Active Excipients

The heading of this section is for convenience only and does not imply strict categorisation. For example, a category, substance or active principle described within this "other active excipients" may also be considered to fall within another section or category in this patent application. One (non-limiting) example is the group of substances known as phospholipids which, according to the invention may be excipients, permeability enhancers or active principles (e.g. phosphatidylcholine which is useful for instance in the treatment of inflammatory bowel disease).

However, in general terms, the invention foresees optional incorporation into the formulation of one or more of the following substances or categories of substances in addition to the primary active agent. For example, the composition may contain a protectant such as, for example, a proteolytic enzyme inhibitor or a protector against acid degradation or both (e.g. an alkali for example sodium hydroxide); an adhesive entity such as, for example, a muco- or bio-adhesive; excipients to maximize solubility of active pharmaceutical compound(s); an antigen(s) and/or an adjuvant(s) to induce an intestinal mucosal or a systemic immune response.

The composition may further comprise excipients to enhance the therapeutic potential of active agents in the ileum and colon including, but not limited to absorption limiters, essential oils such as, for example, omega 3 oils, natural plant extracts such as, for example, neem, ion-exchange resins, bacteria degradable conjugation linkers such as, for example, azo bonds, polysaccharides such as, for example, amylose, guar gum, pectin, chitosan, inulin, cyclodextrins, chondroitin sulphate, dextrans, guar gum and locust bean gum, nuclear factor kappa B inhibitors, acids such as, for example, fumeric acid, citric acid and others, as well as modifications thereof.

The composition may further comprise excipients to reduce systemic side effects associated with absorption in the small intestine including, but not limited to, antioxidants, such as, for example, curcuminoids, flavanoids or more specifically including curcumin, beta-carotene, α-tocopherol, ascorbate or lazaroid.

The composition may further or separately comprise antioxidants (such as, for example, ascorbic acid or BHT—butyl hydroxy toluene) taste-masking or photosensitive components or photoprotective components. Antioxidants may be incorporated in the aqueous phase (e.g. hydrophilic antioxidants) or in the oil phase (e.g. hydrophobic antioxidants such as, for example, vitamin E) for example up to 1% by weight, preferably between 0.01 and 0.50% by weight, more preferably between 0.10 to 0.20% by weight.

Process for Making Colloidal Formulations

The reader is notified that it is important to refer to this section in relation to the Examples.

A basic method for making colloidal formulations is to mix a fluid form (preferably a solution) of the polymer (or mixture of polymers) chosen to be the water-soluble polymer matrix material (e.g. gelatin, gum, alginate etc as described more generally elsewhere herein and in any event optionally in admixture with other components described above) with a dispersed phase material, e.g. a surfactant phase or an oil phase, to form a homogeneous fluid colloid e.g. an emulsion. Taking account of the final composition required (as described elsewhere herein), the dispersed phase and the aqueous phase may be mixed in a proportion in the range 1:6-10, particularly approximately 1:7 or 1:8 for an oily disperse phase or 1:1 to 1:4 for a surfactant (micellar) dispersed phase. In general, only gentle stirring of the components is required using a magnetic or mechanical system e.g. overhead stirrer as would be familiar to a person skilled in the art to achieve emulsification. Continuous stirring is preferred. Any appropriate laboratory stirring apparatus or industrial scale mixer may be utilized for this purpose for example the Magnetic Stirrer (manufactured by Stuart) or Overhead Stirrer (by KNF or Fisher). It is preferred to set up the equipment in such a way as to minimise evaporation of contents such as, for example, water. In one embodiment of the process of the invention, it is preferred to utilise a closed system for stirring in order to achieve this aim.

Where the polymer matrix is substantially constituted by gelatin with the addition of sorbitol, the aqueous phase of polymer matrix is prepared by adding the appropriate quantities of sorbitol (and surfactant and/or active agent, if desired) to water, heating to approximately 60-75° C. until in solution and then adding gelatin although the precise order and timing of addition is not critical. A typical "gelatin solution" comprises 15-25% (preferably 17-18%) gelatin; 75%-85% (preferably 77-82%) of water plus from 1-5% (preferably 1.5 to 3%) sorbitol.

The choice of temperature at which the colloid is formed depends however on various factors include the temperature lability of the active pharmaceutical ingredient and the amount of plasticiser included in the gelatin, the type of gelatin, as well as other factors. Generally however, the gelatin solution (especially in the case of standard or normal gelatin) is maintained at 60° C.-70° C. to maintain it in a fluid state.

The processing temperature can be reduced to a desirable target temperature e.g. 37° C. by use of lower melting-point gelatin (or gelatin derivatives or mixtures of gelatins with melting point reducers) or other polymer matrix material such as, for example, sodium alginate for example when the active principle to be incorporated in the composition of the invention is temperature-labile. Alternatively, temperature-labile active principles may be processed at higher temperatures by using appropriate apparatus or machinery which limits the time during which the temperature-labile active principle is in contact with the higher temperature medium. For example, if gelatin droplets are being formed by machine extrusion and immediately cooled e.g. in a cooling bath, additional appropriate inlet tubing can be used to introduce temperature-sensitive active principle into the fluid gelatin solution (and the mixture can be immediately homogenized) very shortly before ejection from a beading nozzle or other droplet process such that the duration of exposure of the active principle to the higher temperature gelatin is limited so reducing the degree of any heat-dependent degradation of the active principle. This process may use any appropriate device such as, for example, a homogenizer, e.g. a screw homogenizer, in conjunction with an extrusion-type apparatus as described for example in WO 2008/132707 (Sigmoid Pharma) the entirety of which is incorporated herein by reference.

Hydrophobic surfactant, if included, is added to the aqueous phase conveniently at the same time the other components are added e.g. polymer matrix material and plasticiser if included e.g. at the beginning of the processing session. The physical form of the surfactant at the point of introduction into the aqueous phase during preparation may play a role in the ease of manufacture of the composition according to the invention. As such, although liquid surfactants can be employed, it is preferred to utilize a surfactant which is in solid form (e.g. crystalline or powder) at room temperature, particularly when the aqueous phase comprises gelatin. Surfactant is added in the appropriate amount required to achieve the proportion desired and as described above. In general this leads to presence of surfactant in an amount between 0.8% and 1% (by weight) of the aqueous phase.

The dispersed phase material need not be heated unless it is (semi-)solid at ambient temperature and any active principle and in this case other dispersed phase components are usually added at ambient temperature with stirring until clear. These other components may include a volatile (or non-volatile) solvent in addition to the solvent and/or surfactant if selected. The appropriate amount of oil phase active principle (if any) is added to achieve the target proportion. Stirring can continue for a few minutes to a few hours, even overnight, depending on the active principle (for example, an active may take several hours to be fully dissolved). Where it is desired to include an oil e.g. a wax oil which is not liquid or fully liquid at room temperature (e.g. Solutol or Cremophor RH40) in the dispersed phase, slight warming e.g. to 40-50° C. is appropriate.

The colloid may be formed by addition of the dispersed phase to the heated aqueous phase with stirring as described above. The resultant colloid then has the composition of the solidified minibeads described above but with water still present.

The colloid is then poured or introduced into a mould or other vessel or poured onto sheets or between sheets or delivered dropwise (or extruded) into another fluid such that the polymer matrix-containing aqueous phase, on solidification, takes the form of the mould, vessel, sheet or droplet/bead intended. It is preferred to progress to mould-forming e.g. beading, without delay.

Alternatively to moulding, specialised machinery can be employed for example to create the hemispherical beads described above (see section above entitled "Shape, Size and Geometry") in which the invention takes the form of hemispherical beads. It is possible to manufacture a single bead made from joining two such hemispheres (i.e. a single bead having two distinct halves) by using specialist apparatus in which two tubes through which two different emulsions are flowing, normally of circular cross section, are joined shortly before an extrusion point or nozzle (which may be vibrating) into a single dual lumen tube with a flat wall separating the two emulsion flows and which prevents the two emulsions from coming into contact until the point of extrusion. The cross-section of the joined dual-lumen tube up to the point of extrusion therefore appears as two semi-circles. In operation, the two hemispherical emulsion flows combine to form a single, substantially spherical, bead on extrusion such that normal droplets are ejected/extruded for solidification.

Solidification can occur in a variety of ways depending on the polymer of the matrix, for example by changing the temperature around the mould, vessel, sheet, droplet/bead etc or by applying a solidification fluid or hardening solution so that the moulded shape is gelled or solidified. In certain embodiments both temperature change and application of a solidifying fluid or hardening solution are employed together or simultaneously.

In the preferred embodiment in which the composition of the invention takes the form of minibeads, the minibeads may be formed for example by dropping the liquid colloid dropwise into a fluid which effects solidification. Where the viscosity of the colloid to be beaded reaches a certain point, drop formation becomes more difficult and specialised apparatus is then preferred.

In the case where solidification can be achieved by raising or reducing temperature, the temperature of the solidification fluid can be adapted to achieve solidification at the desired rate. For example, when gelatin is used as the polymer matrix, the solidification fluid is at a lower temperature than the temperature of the emulsion thus causing solidification of the polymer matrix. In this case, the solidification fluid is termed a cooling fluid.

In the case where solidification can be achieved chemically, e.g. by induction of cross-linking on exposure to a component of the solidification fluid, the concentration of such component in the solidification fluid and/or its temperature (or other characteristic or content) can be adjusted to achieve the desired rate and degree of solidification. For example, if alginate is chosen as the polymer matrix, one component of the solidification fluid may be a calcium-containing entity (such as, for example, calcium chloride) able to induce cross-linking of the alginate and consequent solidification. Alternatively, the same or similar calcium-containing entity may be included (e.g. dispersed) in the aqueous phase of the liquid colloid prior to beading and triggered to induce cross-linking e.g. by applying a higher or lower pH to a solidification fluid into which droplets of emulsion fall dropwise or are introduced. Such electrostatic cross-linking can be varied as to the resulting characteristics of the minibead by control of calcium ion availability (concentration) and other physical conditions (notably temperature). The solidification fluid may be a gas (for example air) or a liquid or both. For example, when gelatin is used as the polymer matrix, the solidification fluid can be initially gaseous (e.g. droplets passing through cooling air) and then subsequently liquid (e.g. droplets passing into a cooling liquid). The reverse sequence may also be applied while gaseous or liquid cooling fluids alone may also be used. Alternatively, the fluid may be spray-cooled in which the colloid is sprayed into a cooling gas to effect solidification.

In the case of gelatin or other water-soluble polymer destined to form the immobilization matrix, it is preferred that the solidification fluid be a non-aqueous liquid (such as, for example, medium chain triglycerides, mineral oil or similar preferably with low HLB to ensure minimal wetting) which can conveniently be placed in a bath (cooling bath) to receive the droplets of emulsion as they solidify to form beads. Use of a non-aqueous liquid allows greater flexibility in choice of the temperature at which cooling is conducted.

Where a liquid cooling bath is employed, it is generally maintained at less than 20° C., preferably maintained in the range 5-15° C., more preferably 8-12° C. when standard gelatin is used as the polymer matrix. If a triglyceride is chosen as the cooling fluid in the cooling bath, a preferred example is Miglyol 810 from Sasol.

If gelatin is selected as the polymer matrix, respect for appropriate temperature ranges ensures solidification of the gelatin at an appropriate rate to avoid destruction e.g. of tertiary protein structure in the case where the active principle is a protein.

If alginate is selected as the polymer matrix, a typical method of making minibeads involves dropwise addition of a 3% sodium alginate solution in which oil droplets are dispersed as described above into a 4° C. crosslinking bath containing 0.1 M calcium chloride to produce calcium alginate (this method can be referred to as "diffusion setting" because the calcium is believed to diffuse into the minibeads to effect cross-linking or setting). Using a syringe pump, or Inotech machine, droplets can be generated or extruded (e.g. at 5 mL/h if a pump is used) through a sterile needle or other nozzle (described elsewhere herein) which can be vibrating as discussed elsewhere herein. Airflow of between 15 and 20 L/min through 4.5 mm tubing can be applied downwards over the needle to reduce droplet size if desired. Newly formed minibeads can then be stirred in the calcium chloride bath for up to an hour. If carrageenan is used as the polymer matrix both salt and reduction in temperature e.g. by dropping into cooling oil may be used to obtain solidification.

An alternative approach when using alginate is internal gelation in which the calcium ions are dispersed in the aqueous phase prior to their activation in order to cause gelation of hydrocolloid particles. For example, this can be achieved by the addition of an inactive form of the ion that will cause crosslinking of the alginate, which is then activated by a change in e.g. pH after sufficient dispersion of the ion is complete (see Glicksman, 1983a; Hoefler, 2004 which are both incorporated herein by reference). This approach is particularly useful where rapid gelation is desired and/or where the diffusion approach may lead to loss of API by diffusion thereof into the crosslinking bath.

Following shape-forming, moulding or beading, the resultant shapes or forms may be washed then dried if appropriate. In the case of minibeads solidified in a solidification fluid, an optional final step in the method of production described above therefore comprises removal of the solidified minibeads from the solidification fluid. This may be achieved e.g. by collection in a mesh basket through which the solidification fluid (e.g. MCT) is drained and the beads retained and is preferably conducted without delay e.g. as soon as the beads have formed or within 5, 10, 15, 20, 25 or 30 minutes of their formation. Excess solidification fluid may then be removed using a centrifuge (or other apparatus or machine adapted to remove excess fluid) followed by drying of the beads to remove water or free water and/or removal of some or all of any additional solvent e.g. ethanol or isopropyl alcohol used to dissolve or facilitate dissolution of the active principle in preceding steps optionally followed by washing (e.g. using ethyl acetate) and a subsequent "drying" step to remove excess solvent (e.g. ethyl acetate). Isopropyl alcohol is an example of a solvent which is preferably removed later in processing to reduce residues in the oil or aqueous phase. Drying can be achieved by any suitable process known in the art such as use of a drum drier (e.g. Freund Drum dryer which may be part of the Spherex equipment train if used) with warm air at between 15° C. and 25° C., preferably around 20° C. leading to evaporation or entrainment of the water by the air. Use of gelatin as the polymer matrix (e.g. as principal constituent of the aqueous immobilisation phase) in most cases requires a drying step and for minibeads this is preferably achieved by drying in air as above described. The resultant composition (the composition of the invention) is essentially dry as described in more detail above.

In terms of the way in which colloid droplets may be formed in the first step of the beading process described above, variations of the above described method are possible including introducing droplets into a variety of solidification fluids.

In general, the minibeads may be generated by the application of surface tension between the fluid colloid having an aqueous continuous phase and an appropriate solidification fluid such as, for example, gas or liquid in order to create the spherical or substantially spherical shape of the ultimate beads.

Alternatively, the minibeads may be produced through ejection or extrusion of the liquid colloid through an orifice or nozzle with a certain diameter and optionally subject to selected vibrational frequencies and/or gravitational flow. Examples of machines which may be used are the Freund Spherex, ITAS/Lambo, Globex or Inotech processing equipment. Operation of the Spherex machine manufactured by Freund as may be desired to manufacture minibeads according to the present invention is described in U.S. Pat. No. 5,882,680 (Freund), the entire contents of which are incorporated herein by reference. It is preferred to select a vibrational frequency in the region of 10-15 RPM although the ultimate choice (and separately the amplitude of vibration selected) depends on the viscosity of the colloid to be beaded. If the polymer matrix is chosen to solidify at lower temperature, it may be appropriate to maintain the lines to the orifice/nozzle at a certain temperature to maintain the fluidity of the solution.

The Spherex machine (and others) may be adapted to make use of a dual concentric lumen nozzle to ensure simultaneous extrusion of two fluids, the fluid in the inner lumen forming a core and the fluid of the outer lumen forming a capsule. The fluid forming the capsule is solidified according to one of the methods described. It may or may not be desirable for the fluid forming the core to be susceptible of solidification to yield a particular embodiment of the composition of the invention. The machinery adapted in this way can be used to manufacture the composition of the invention in the form of a capsule in which the core of the composition is filled with a fluid (a gas or a liquid) as described in the section above entitled "Shape, Size and Geometry" (noting that the core, like the capsular material, may be a composition, albeit optionally a distinct composition, according to the invention i.e. susceptible of solidification according to one of the methods described above). A three-lumen nozzle and appropriate tubing may be employed if it is desired to include an intermediate internal layer e.g. internal film layer of non-aqueous material on the inner face of the sphere with the intermediate layer conveniently being solid at room temperature. Thus, in terms of the softness/hardness of successive layers, the composition may for example be described as solid:solid in the case of two layers or solid:solid:solid in the case of 3 layers or liquid/semi-liquid:solid:solid in the case of 3 layers.

The preceding paragraphs describe the formation of uncoated beads. It is a preferred embodiment of the present invention to have coated beads which are described in more detail elsewhere herein. Such coatings may be single or multiple and may be applied in a number of ways (see separate section).

With regard to one of the methods described above (ejection of colloid through an optionally vibrating nozzle) with two concentric orifices (centre and outer), the outer fluid may form a coat (outside the minibead) of e.g. polymeric material (polymeric coating) which may contain an active principle or may impart controlled release characteristics to the minibead and the inner layer (core) may be a colloid as described herein. The Spherex machine manufactured by Freund (see U.S. Pat. No. 5,882,680 to Freund) is preferably used (the entire contents of this patent is incorporated herein by reference).

Use of the Spherex machine achieves very high monodispersity. For example, in a typical 100 g, batch 97 g of minibeads were between 1.4 to 2 mm diameter or between 1 and 2 mm. Desired size ranges can be achieved by methods known in the art for rejecting/screening different sized particles. For example, it is possible to reject/screen out the larger/smaller beads by passing a batch first through e.g. a 2 mm mesh and subsequently through a 1.4 mm mesh.

The 1.4 to 2 mm diameter range is a good size if it is desired to coat the minibeads (if smaller, the spray of the coating machine may bypass the minibead; if too large hard, the beads may be harder to fluidise which is necessary to achieve consistent coating).

The minibeads are preferably internally (i.e. cross-sectionally) homogeneous i.e. monolithic although processing conditions may be varied for example by altering the temperature of the liquid colloid, the solidification fluid and the concentration of components in these fluids and the time allowed for certain processing steps to occur including drying. Although not currently preferred, such variations may be applied in the case of minibead manufacture to achieve heterogeneity such as, for example, a harder skin and softer core with less than complete immobilization of oil droplets towards the core as opposed to the surface of the bead. Larger (e.g. non-beaded) forms or shapes of the composition according to the invention may particularly be engineered to embody such heterogeneity. However, it is currently preferred to have internally homogenous compositions and, within the minibead embodiment, this can be favoured by conducting the beading/droppletting using a homogeneous medium e.g. a well dispersed colloid. Such homogeneity in the emulsion to be beaded can help avoid the drying conditions affecting symmetry.

The oral composition may be used for a number of applications as discussed elsewhere herein. The active principle(s) may be released immediately (immediate release profile) or be released after some delay and/or over an extended period (delayed and/or extended release profile). For immediate release, the minibeads or other formats may be uncoated or coated enterically to protect against stomach acid for immediate release in the small intestine.

Alternatively, if controlled release is desired (i.e. delayed, extended or site-targeted release etc), or if medium-independent release is desired, it is possible, according to the invention to apply a coat to the minibeads or other formats. Application of the appropriate coat may, for example if colonic release is required, allow for say less than 10% of the active principle to be dissolved (in dissolution medium) at 4 hours and then a burst (sudden release) towards a maximum dissolution (approaching 100%) in the subsequent 24 hours. Many alternative target profiles are possible and this example is purely for illustration.

Thus, the composition may be in the form of minibeads at least some of which bear a coat (i.e. are coated) in order to control release of active principle from the minibead. In one embodiment, the coat is a film and in another embodiment, it is a membrane. The coat, film or membrane comprises one or more substances preferably of a polymeric nature (e.g. methacrylates etc; polysaccharides etc as described in more detail below) or combination of more than one such substance, optionally including other excipients or active principles, such as, for example, plasticizers, described e.g. in the sections above on active principles. Preferred plasticizers, if they are used, include hydrophilic plasticizers for example triethyl citrate (TEC) which is particularly preferred when using the Eudragit family of polymers as coatings as described below. Another preferred plasticiser, described in more detail below in relation to coating with ethyl cellulose, is DBS. Alternative or additional optionally included excipients are glidants. A glidant is a substance that is added to a powder or other medium to improve its flowability. A typical glidant is talc which is preferred when using the Eudragit family of polymers as coatings.

Non-Dried Colloid Formulations

The invention does not require that the steroid be administered as a dried colloidal formulation. The steroid could be incorporated into a minibead comprising a water soluble polymer matrix and not containing a dispersed phase. The steroid may therefore be water soluble and be dissolved and/or dispersed in the water soluble polymer matrix. Alternatively the steroid may be water-insoluble and be dispersed in the water soluble polymer matrix. Such a minibead may be prepared by a method as disclosed herein where the dispersed phase is not added to the mix that forms the minibead.

The steroid may be administered as any suitable formulation which releases the steroid in the desired region(s) of the GIT. For example, the steroid may be budesonide administered as a multi-matrix formulation budesonide MMX®. See WO0076478 for more information as to such multi-matrix formulations; WO0076478 is incorporated herein in its entirety.

The steroid may be budesonide administered as Entocort® EC.

The formulation may comprise the steroid in solution in a liquid, semi-solid or solid, for example in an oily or waxy medium, or in the hydrophobic part of a self-assembly structure.

The steroid may be administered as a multiple mini-unit formulation, comprising a multiplicity of mini-tablets, mini-capsules and or pellets etc. The mini-units may comprise the steroid in solid solution, semi-solid solution or liquid solution. The mini-units may be minibeads. The mini-beads may comprise the steroid in liquid solution.

The steroid may be administered as a two layer minibead. Such a minibeads may be made using an aqueous phase comprising a water soluble polymer and a hydrophobic or water-immiscible phase respectively through the outer and inner orifices of a nozzle having a central inner orifice and, arranged concentrically therearound, an outer orifice. The aqueous phase and the hydrophobic or water-immiscible phase may be as described herein in relation to dried emulsion minibeads. Such two layer minibeads and their manufacture are described, for example, in WO 2008/122967 of Sigmoid Pharma Limited, which is included herein by reference.

Active agents which are more readily water-soluble, e.g. the hydroxylase inhibitor hydralazine, may be incorporated in a hydrophilic phase (e.g. a water-soluble polymer) in dissolved or particulate form.

Solid dosage forms for oral administration include capsules, minicapsules, beads, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Liquid dosage forms for oral administration include pharmaceutically acceptable emulsions, solutions, suspensions, syrups and elixirs. In addition to the steroid, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include excipients such as wetting agents, emulsifying and suspending agents, sweetening, flavoring and perfuming agents. Suspensions, in addition to the steroid, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the steroid with suitable non-irritating excipients or carriers such as cocoa butter, polyethylene glycol or a suppository wax which are solid at room temperature but liquid at body temperature and therefore melt in the rectum or vaginal cavity and release the steroid.

Suitably, the formulations contain a dissolution aid. The dissolution aid is not limited as to its identity so long as it is pharmaceutically acceptable. Examples include non-ionic surfactants; ionic surfactants; and amphoteric surfactants.

The solid dosage forms can be prepared with coatings and shells as well known in the pharmaceutical formulating art and described elsewhere herein. They may optionally contain opacifying agents and may also be of a composition such that they release the active ingredient(s) only, or preferentially, in a certain part of the intestinal tract, and/or in delayed fashion.

A solid dosage form may comprise a waxy phase in which one or more active agents are dissolved. Suitable waxy materials are described elsewhere herein.

Coating

The formulations described herein are typically provided with a controlled release coating. Such a controlled release coating may comprise a polymer or a combination of polymers, as is well known.

In the case of combinations of polymers, combinations may be selected in order to achieve the desired delay (or other change) in the release of the drug and/or poration of the coating and/or exposure of the minibead or other format within the coating to allow egress of drug and/or dissolution of the immobilization matrix. In one embodiment, two types of polymers are combined into the same polymeric material, or provided as separate coats that are applied to the minibeads.

It has previously been stated that the formulations may comprise more than one population of minibeads. Within the coating embodiment, the differences between populations may lie in the coat i.e. two (or more) populations of minibeads may differ in a number of respects one of which is the coating.

The coat may be applied as described below and may vary as to thickness and density. The amount of coat is defined by the additional weight added to (gained by) the dried composition (e.g. minibead) of the invention. Weight gain is preferably in the range 0.1% to 50%, preferably from 1% to 15% of the dry weight of the bead, more preferably in the range 3% to 10%, or in the range 3%-7%, or in the range 5-12%, or in the range 8-12%.

The polymeric coating material may comprise methacrylic acid co-polymers, ammonio methacrylate co-polymers, or mixtures thereof. Methacrylic acid co-polymers such as, for example, EUDRAGIT™ S and EUDRAGIT™ L (Evonik) are particularly suitable. These polymers are gastroresistant and enterosoluble polymers. Their polymer films are insoluble in pure water and diluted acids. They may dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit solubility at a variety of pH levels, e.g. between the pHs at which EUDRAGIT™ L and EUDRAGIT™ S are separately soluble.

The trademark "EUDRAGIT" is used hereinafter to refer to methacrylic acid copolymers, in particular those sold under the EUDRAGIT™ by Evonik.

The coating can comprise a polymeric material comprising a major proportion (e.g., greater than 50% of the total polymeric coating content) of at least one pharmaceutically acceptable water-soluble polymer, and optionally a minor proportion (e.g., less than 50% of the total polymeric content) of at least one pharmaceutically acceptable water insoluble polymer. Alternatively, the membrane coating can comprise a polymeric material comprising a major proportion (e.g., greater than 50% of the total polymeric content) of at least one pharmaceutically acceptable water insoluble polymer, and optionally a minor proportion (e.g., less than 50% of the total polymeric content) of at least one pharmaceutically acceptable water-soluble polymer.

Ammonio methacrylate co-polymers such as, for example, EUDRAGIT™ RS and EUDRAGIT™ RL (Evonik) are suitable for use in the present invention. These polymers are insoluble in pure water, dilute acids, buffer solutions, and/or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMCl) groups in the polymer. For example, those polymers having EA:MMA:TAMCl ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability. A particularly preferred diffusion-controlled pH-independent polymer in this family is RS 30 D which is a copolymer of ethyl acrylate, methyl methacrylate and a low content of methacrylic acid ester with quaternary ammonium groups present as salts to make the polymer permeable. RS 30 D is available as an aqueous dispersion.

The amino methacrylate co-polymers can be combined in any desired ratio, and the ratio can be modified to modify the rate of drug release. For example, a ratio of EUDRAGIT™ RS:EUDRAGIT™ RL of 90:10 can be used. Alternatively, the ratio of EUDRAGIT™ RS:EUDRAGIT™ RL can be about 100:0 to about 80:20, or about 100:0 to about 90:10, or any ratio in between. In such formulations, the less permeable polymer EUDRAGIT™ RS generally comprises the majority of the polymeric material with the more soluble RL, when it dissolves, permitting gaps to be formed through which solutes can come into contact with the minibead allowing pre-dissolved pharmaceutical actives to escape in a controlled manner.

The amino methacrylate co-polymers can be combined with the methacrylic acid co-polymers within the polymeric material in order to achieve the desired delay in the release of the drug and/or poration of the coating and/or exposure of the minibead within the coating to allow egress of drug and/or dissolution of the immobilization or water-soluble polymer matrix. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the minibeads.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. A further example is EUDRAGIT® L 30D-55 which is an aqueous dispersion of anionic polymers with methacrylic acid as a functional group. It is available as a 30% aqueous dispersion.

In addition to the EUDRAGIT™ polymers described above, a number of other such copolymers can be used to control drug release. These include methacrylate ester copolymers such as, for example, the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg. 109-114, the entirety of which is incorporated herein by reference.

Several derivatives of hydroxypropyl methylcellulose (HPMC) also exhibit pH dependent solubility and may be used in the invention for coating. These include hydroxypropyl methylcellulose phthalate (HPMCP), which rapidly dissolves in the upper intestinal tract and hydroxypropyl methylcellulose acetate succinate (HPMCAS) in which the presence of ionizable carboxyl groups causes the polymer to solubilize at high pH (>5.5 for the LF grade and >6.8 for the HF grade). These polymers are commercially available from Shin-Etsu Chemical Co. Ltd. As with other polymers described herein as useful for coatings, HPMC and derivatives may be combined with other polymers e.g. EUDRAGIT RL-30 D.

It is particularly preferred according to the invention to use a polymeric coating substance which is pH-independent in its dissolution profile and/or in its ability to release active principles incorporated in the minibeads of the invention. Examples have already been given (e.g., Eudragit RS and RL). Another example of a pH-independent polymeric coating substance is ethylcellulose. It will be understood that an ethylcellulose composition for use in coating a dosage form for may comprise in addition to ethylcellulose and, in the case of a liquid composition, a liquid vehicle, one or more other components. The other components may serve to modulate the properties of the composition, e.g. stability. The ethylcellulose may be the sole controlled release polymer in such a composition. The ethylcellulose may be in an amount of at least 50%, at least 60%, at least 70%, at least 80%, at least 90% or at least 95% by weight of the dry weight of composition for use in coating a dosage form.

Accordingly, an ethylcellulose coating may include other components in addition to the ethycellulose. The ethylcellulose may be in an amount of at least 50%, at least 60%, at least 70%, at least 80%, at least 90% or at least 95% by weight of the ethylcellulose coating.

A particular ethylcellulose coating composition which may be applied to the compositions of the invention is a dispersion of ethylcellulose in a sub-micron to micron particle size range, e.g. from about 0.1 to 10 microns in size, homogeneously suspended in water with the aid of an emulsification agent, e.g. ammonium oleate. The ethylcellulose dispersion may optionally and preferably contain a plasticizer, for example dibutyl sebacate (DBS) or medium chain triglycerides. Such ethylcellulose dispersions may, for example, be manufactured according to U.S. Pat. No. 4,502,888, which is incorporated herein by reference. One such ethylcellulose dispersion suitable for use in the present invention and available commercially is marketed under the trademark Surelease®, by Colorcon of West Point, Pa. USA. In this marketed product, the ethylcellulose particles are, e.g., blended with oleic acid and a plasticizer, then optionally extruded and melted. The molten plasticized ethylcellulose is then directly emulsified, for example in ammoniated water optionally in a high shear mixing device, e.g. under pressure. Ammonium oleate can be formed in situ, for instance to stabilize and form the dispersion of plasticized ethylcellulose particles. Additional purified water can then be added to achieve the final solids content. See also U.S. Pat. No. 4,123,403, which is incorporated herein by reference.

The trademark "Surelease®" is used hereinafter to refer to ethylcellulose coating materials, for example a dispersion of ethylcellulose in a sub-micron to micron particle size range, e.g. from about 0.1 to 10 microns in size, homogeneously suspended in water with the aid of an emulsification agent, e.g. ammonium oleate. In particular, the trademark "Surelease®" is used herein to refer to the product marketed by Colorcon under the Surelease® trademark.

Surelease® dispersion is an example of a combination of film-forming polymer, plasticizer and stabilizers which may be used as a coating to adjust rates of active principle release with reproducible profiles that are relatively insensitive to pH. The principal means of drug release is by diffusion through the Surelease® dispersion membrane and is directly controlled by film thickness. Use of Surelease® is particularly preferred and it is possible to increase or decrease the quantity of Surelease® applied as coating in order to modify the dissolution of the coated minibead. Unless otherwise stipulated, use of the term "Surelease" may apply to Surelease E-7-19020, E-7-19030, E-7-19040 or E-7-19050. E-7-19020 comprises ethylcellulose blended with oleic acid and dibutyl sebacate, then extruded and melted. The molten plasticized ethylcellulose is then directly emulsified in ammoniated water in a high shear mixing device under pressure. Ammonium oleate is formed in situ to stabilize and form the dispersion of plasticized ethylcellulose particles. Additional purified water is then added to achieve the final solids content. E-7-19030 additionally comprises colloidal anhydrous silica dispersed into the material. E-7-19040 is like E-7-19020 except that it comprises medium chain triglycerides instead of dibutyl sebacate. E-7-19050 derives from blending ethylcellulose with oleic acid before melting and extrusion. The molten plasticized ethylcellulose is then directly emulsified in ammoniated water in a high shear mixing device under pressure. Ammonium oleate is formed in situ to stabilize and form the dispersion of plasticized ethylcellulose particles. However, E-7-19040 is preferred.

The invention also contemplates using combinations of Surelease with other coating components, for example sodium alginate, e.g. sodium alginate available under the trade name Nutrateric™.

In addition to the EUDRAGIT™ and Surelease® polymers discussed above, other enteric, or pH-dependent, polymers can be used. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate. Additionally, where compatible, any combination of polymer may be blended to provide additional controlled- or targeted-release profiles.

The coating can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as, for example, sodium lauryl sulfate and polysorbates, organic acids such as, for example, acetic acid, adipic acid, citric acid, fumaric acid, glutaric acid, malic acid, succinic acid, and tartaric acid, sugars such as, for example, dextrose, fructose, glucose, lactose, and sucrose, sugar alcohols such as, for example, lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566 all of which are incorporated herein by reference in their entirety.

As noted above, pH-independent coating polymers may be used, for example ethylcellulose, as previously discussed. In the case of a dosage form targeting the steroid and any other actives to the ileum and/or colon, the addition to an ethylcellulose (e.g. Surelease™) or other pH-independent coating of a second polymer (e.g. a polysaccharide, especially a heteropolysaccharide) which is susceptible to degradation by bacterial enzymes but not by digestive enzymes, e.g. human digestive enzymes, helps ensure that the barrier function of the coating is destroyed by the action of such enzymes in the terminal ileum and/or colon, thereby ensuring release of the actives in the ileum and/or colon. The inclusion of such a bacterial enzyme-degradable polymer in a pH-independent coating, e.g. ethylcellulose, provides flexibility in modulating the amount of polymer added to the minibeads of the invention in order to achieve optimal dissolution profiles. In general terms, therefore, the disclosure includes formulations as described herein which comprise a coating comprising a combination of a delayed release material, for example an erodible polymer e.g.

ethylcellulose, and a polymer susceptible of degradation by bacterial enzymes in the colon, e.g. a polysaccharide and particularly a water-soluble polysaccharide, particularly a pectin.

The disclosure therefore includes a coating for compositions intended to release their active payload in the colon which is a combination of ethylcellulose (preferably formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon. Such polysaccharides include chondroitin sulphate, pectin, dextran, guar gum and amylase, chitosan etc and derivatives of any of the foregoing. Chitosan is particularly preferred in connection with obtaining a colon-specific release profile. The disclosure also includes a composition comprising a combination of ethylcellulose (preferably formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon; the composition may include a liquid vehicle, e.g. water.

The use of polysaccharides by themselves for coating purposes has been tried with limited success. Most of the non-starch polysaccharides suffer from the drawback of lacking good film forming properties. Also, they tend to swell in the GI tract and become porous, resulting in the early release of the drug. Even amorphous amylose, which is resistant to degradation by pancreatic alpha amylase but capable of degradation by colonic bacterial enzymes has the disadvantage of swelling in aqueous media although this can be controlled by incorporating insoluble polymers like, ethyl cellulose and acrylates into the amylose film. Amylose however is not water-soluble and although water-soluble polysaccharides are not excluded, the present inventors have found that use of a water-soluble polysaccharide (WSP) susceptible of bacterial enzymic degradation brings particularly advantageous results when used as a coating in accordance with this embodiment of the present invention. A particularly preferred polysaccharide in this embodiment of the present invention is pectin. Various kinds of pectin may be used including pectin of different grades available i.e. with differing degrees of methylation (DM), i.e. percentage of carbonyl groups esterified with methanol, for example pectins with a DM of more than 50%, known as High Methoxy (HM) Pectins or Low Methoxy (LM) pectins, or a pectin combination comprising an HM pectin and an LM pectin. It is also possible in this embodiment to use pectins having various degrees of acetylation (DAc). Taken together, the DM and DAc or the degree of substitution is known as Degree of Esterification (DE). Pectins of various DE's may be used according to the invention. As an alternative to pectin, sodium alginate may be used as a polysaccharide according to an embodiment of the invention. However, other embodiments may conveniently include amylose and/or starch which contains amylose. Various grades of starch, containing different percentages of amylose may be used including for example Hylon V (National Starch Food Innovation) which has an amylose percentage of 56% or Hylon VII which has an amylose percentage of 70%. The remaining percentage is amylopectin. The polysaccharides pectin, amylose and sodium alginate are particularly preferred for achieving colon delivery i.e. for compositions intended to release active principles in the colon.

It has been found that pectin can act as a former of pores in the coating otherwise provided by ethylcellulose (preferably Surelease). By "pores" is not meant shaft-like holes from the surface to the core of the minibead, rather areas of weakness or absence of coating occurring stochastically on and within the coating of the invention.

Pore formers have been described before in connection with Surelease (see e.g. US 2005/0220878) but in relation to "gastro-insoluble" substances such as, for example, alginate.

Where the water-soluble polysaccharide (WSP) is pectin, the proportion of ethylcellulose or Surelease™ to pectin is ideally in the range 90:10 to 99:1, preferably, 95:5 to 99:1, more preferably 98:2 to 99:1.

In this particularly preferred combination (ethylcellulose or Surelease™+WSP e.g. pectin) the weight gain and ratio between ethylcellulose or Surelease™ and WSP can be varied to refine the behaviour of the coating and the composition of the invention when it bears such a coat. Thus to the inventors/applicant's surprise, the advantages of this preferred combination of coating polymers were further pronounced by selecting a weight gain in the range 0 to 30% (preferably 5 to 10%) and a weight ratio of ethylcellulose or Surelease to pectin in the range 95:5 to 99.5:0.5 preferably 97:3 to 99:1 inclusive. Particularly favoured weight gains using ethylcellulose or Surelease are those in the range 5-12% or in the range 8-12%.

Although the focus above has been on extending and/or sustaining release of active principles from minibeads or other formats, also contemplated are uncoated or simple enteric coated minibeads or other formats providing early, small intestinal API release with sufficient enteric coating merely to protect the minibeads from dissolution in the stomach.

It is preferred to dry the minibeads before they are coated with a suitable polymeric coat (as described in more detail above/below). It is also preferred, in certain embodiments to apply a first coat before applying a second. In general the first coat and the second coat may be of the same or different materials and be chosen from any of the classes of coating material described herein. In specific embodiments, the first coat optionally protects the core (bead) from interaction with the second coat and/or prevents leaching of bead contents into the second coat. For example, the first coat may comprise or be hypromellose, e.g. it may be made with a mixture of hypromellose, titanium dioxide and polyethylene glycol; the first coat may comprise at least 50 wt % hypromellose and optionally at least 75 wt % hypromellose, e.g. at least 80 wt % or at least 85 wt % or 90 wt % hypromellose. The coating material used to form the first coat may therefore comprise a dry weight percentage of hypromellose mentioned in the preceding sentence. The second (outer) coat may be an enteric coating as described above or comprise a mixture of polymers including a polymer degradable by bacterial or other enzymes, for example be made of the Surelease-pectin mixture described above. If it is desired for the first coat to use a mixture of hypromellose, titanium dioxide and polyethylene glycol, commercial products corresponding to such mixtures are available including Opadry White, a product commercialised by Colorcon. More generally, various products commercialised under the trade name Opadry and Opadry II. Further nonlimiting examples include Opadry YS-1-7706-G white, Opadry Yellow 03B92357, Opadry Blue 03B90842). These compositions are available as dry film coating compositions that can be diluted in water shortly before use. Opadry and Opadry II formulations comprise a cellulosic film forming polymer (e.g., HPMC and/or HPC), and may contain polydextrose, maltodextrin, a plasticizer (e.g., triacetin, polyethylene glycol), polysorbate 80, a colorant (e.g., titanium dioxide, one or more dyes or lakes), and/or other suitable film-forming polymers (e.g., acrylate-methacrylate copolymers). Suitable OPADRY or OPADRY II formulations may comprise a plasticizer and one or more of maltodextrin, and polydextrose (including but not limited to a) triacetin and polydextrose or maltodextrin or lactose, or b) polyethylene glycol and polydextrose or maltodextrin). Particularly preferred commercial products are Opadry White (HPMC/HPC-based) and Opadry II White (PVA/PEG-based). Alternative (non-Opadry) products for initial protective coats include polyvinyl alcohol-polyethylene glycol graft copolymers such as is available commercially under the name Kollicoat IR and methyl methacrylate ammonium-based copolymers such as are available commercially under the name Eudragit E. Another preferred example is low molecular weight HPMC. The optional inner coat is applied in the same manner as is the outer (or sole) coat (or coating layer).

The coating process can be carried out by any suitable means such as, for example, by use of a coating machine which applies a solution of a polymer coat (as described above in particular) to the minibeads. Polymers for coating are either provided by the manufacturer in ready-made solutions for direct use or can be made up before use following manufacturers' instructions.

Appropriate coating machines are known to persons skilled in the art and include, for example, a perforated pan or fluidized-bed system for example the GLATT, Vector (e.g. CF 360 EX), ACCELACOTA, Diosna, O'Hara and/or HICOATER processing equipment. To be mentioned is the MFL/01 Fluid Bed Coater (Freund) used in the "Bottom Spray" configuration.

Typical coating conditions are as follows:

| Process Parameter | Values |
| --- | --- |
| Fluidising airflow (m3/h) | 20-60 (preferably 30-60) |
| Inlet air temperature (° C.) | 20-65 |
| Exhaust air temperature (° C.) | 38-42 |
| Product temperature (° C.) | 38-42 |
| Atomizing air pressure (bar) | Up to 1.4 e.g. 0.8-1.2 |
| Spray rate (g/min) | 2-10 and 3-25 RPM |

Whether as part of the polymeric coat or independently thereof, the minibeads of the disclosure may be coated with additional drug layers using methods conventional in the art of pharmaceutical science (such as for example using coating machines as just described) to produce a composition having one or more layer(s), each layer containing one or more active pharmaceutical or other ingredient/excipient as described elsewhere herein. Drug layering means the deposition of at least one or successive layers of drug entities from solution, suspension or dry powder on nuclei e.g. minibeads as described herein. Drug layering includes solution/suspension layering, powder layering and powder drug layering. In solution/suspension layering, drug particles are dissolved or suspended in a binding liquid. In powder layering, complete dissolution does not occur, due to low liquid saturation, irrespective of the solubility of the active agent in the binding liquid. In powder drug layering, a binder solution is first sprayed onto previously prepared inert seeds e.g. minibeads as described herein, followed by the addition of powder. Conventional pan coaters may be used as described above for polymer coating although modified forms of pan coaters are preferred including fluidised-bed and centrifugal rotary granulators. Examples of suitable granulators include the Rotor granulator. (Glatt), the Rotor-processor (Aeromatic), the Spir-a-Flow (Freund) and the CF-granulator (Freund). In applying a drug layer, the drug to be layered onto the minibead may optionally first be admixed with appropriate excipients such as, for example, binders as described elsewhere herein. A particularly preferred binder in this context is polyvinyl pyrrolidone (also spelt polyvinylpyrrolidone and also known as PVP or povidone). PVPs of various K-values may be used. The K-value of PVP is a function of its average molecular weight, the degree of polymerization, and the intrinsic viscosity. It is particularly preferred to use PVP K-32. Up to 5% of the dry weight of the composition of the invention in this embodiment may be made up of such binders. Approximately 1% or less is preferred. Other suitable binders which may be used in drug-layering include gelatin, carboxymethyl cellulose, hydroxypropyl methylcellulose and hydrolysed starches e.g. maltodextrins. Compositions embodying drug layering may also optionally be coated with a polymer coating, or include a polymer layer, to control release as described more generally above including the option to include the same or a different active principle in this polymer coat.

The layered bead or minibead may have a plurality of layers, e.g. 2, 3, 4 or 5 layers, comprising an active principle, wherein the active principle of each layer is selected independently from the active principle of each other layer. In one embodiment, each layer comprises the same active principle as each other layer; in another embodiment, no two layers comprise the same active principle. The term "active principle" in this paragraph embraces both a single active entity and a combination of active entities. The layered bead or minibead may comprise one or more polymer layers, to control release as described more generally above. Such a polymer layer may contain an active principle and therefore constitute a drug layer as well as a release control layer. Alternatively, a polymer layer may be free of active principle. A polymer layer, whether or not it contains an active principle, may be located between the core and a drug layer outside the polymer layer, or between two drug layers, or may form an outer layer.

The polymer layer may be located between the core and the active principle layer. The polymer layer may be located externally of the active principle layer. The layered bead or minibead may comprise a plurality of active principle layers and, additionally or alternatively, it may comprise a plurality of polymer layers. In some embodiments, there is at least one active principle layer which comprises a release-controlling polymer. In some embodiments, the outermost layer comprises a release-controlling polymer, which may contain an active principle or, in another implementation, be free of active principle.

The optionally coated minibeads may be formulated directly following their manufacture in the ways described above. In an alternative embodiment, it may be desired to impart different properties to the minibeads and/or to a final solid dosage product. One way of achieving this according to the invention is through granulation e.g. to improve the flow of powder mixtures of minibeads with other components as e.g. described above in relation to binders. Granules of intact or broken minibeads may be obtained by adding liquids (e.g. binder or solvent solutions) and effecting a granulating step as described in the prior art. Larger quantities of granulating liquid produce a narrower particle size range and coarser and harder granules, i.e. the proportion of fine granulate particles decreases. The optimal quantity of liquid needed to get a given particle size may be chosen in order to minimise batch-to-batch variations. According to this embodiment, wet granulation is used to improve flow, compressibility, bio-availability, homogeneity, electrostatic properties, and stability of the composition of the invention presented as a solid dosage form. The particle size of the granulate is determined by the quantity and feeding rate of granulating liquid. Wet granulation may be used to improve flow, compressibility, bio-availability, and homogeneity of low dose blends, electrostatic properties of powders, and stability of dosage forms. A wet granulation process according to this embodiment may employ low or high shear mixing devices in which a low viscosity liquid (preferably water) is added to a powder blend containing binder previously dry mixed with the rest of the formulation including minibeads. Alternative granulation approaches which may be utilized include high-shear, extrusion and conventional wet granulation.

The invention contemplates a treatment that attains one or more of the following objectives as compared to those now available: (i) greater efficacy; (ii) fewer side effects; (iii) reduced systemic drug levels; (iv) reduced cost; (v) improved manufacturing method, (vi) an alternative treatment or prophylactic.

The invention further includes the subject matter of the following clauses:
1. A steroid for use in enteral administration and for use in treating intestinal fibrosis.
2. A steroid for use of clause 1 for use in oral administration.
3. A steroid for use of clause 1 or clause 2 which is selected from aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives, and combinations thereof.
4. A steroid for use of any preceding clause which is susceptible to first pass metabolism.
5. A steroid for use of clause 4 which is selected from budesonide, flunisolide, fluticasone proprionate, rimexolone, butixocort, tixocortol and beclomethasone and the salts, esters, conjugates and prodrugs thereof.
6. A steroid for use of clause 1 or clause 2 which is budesonide, or a prodrug, ester or conjugate thereof.
7. A steroid for use of any preceding clause which is dissolved in a liquid or in a wax which has a melting temperature of no more than 37° C.
8. A steroid for use of clause 7 wherein the liquid or wax comprises a macrogol ester.
9. A steroid for use of clause 8 wherein the macrogol ester is macrogol-15-hydroxystearate.
10. A steroid for use of clause 7 wherein the liquid comprises a medium chain triglyceride.
11. A steroid for use of any preceding clause which is comprised in an oral formulation adapted to release the steroid at least in the colon.
12. A steroid for use of any preceding clause which is comprised in an oral formulation adapted to release the steroid at least in the ileum.
13. A steroid for use of any preceding clause which is comprised in an oral formulation adapted to release the steroid at least in the duodenum.
14. A steroid for use of any of clauses 1 to 6 which is comprised in an immediate release formulation.
15. A steroid for use of any preceding clause which is in solution in a controlled release formulation.
16. A steroid for use of any of any preceding clause wherein the controlled release formulation is a multiple minibead formulation.
17. A steroid for use of clause 16 wherein the minibeads comprise a water soluble polymer matrix having dispersed therein the steroid.
18. A steroid for use of any of clauses 1 to 15 wherein the steroid is comprised in a formulation obtainable by a process comprising:
    (i) dissolving a water-soluble polymer in water to form an aqueous solution;
    (ii) dissolving or dispersing the steroid in a liquid which will mix with the water to form a colloid to form a steroid solution or dispersion;
    (iii) mixing the aqueous solution and the steroid solution or dispersion to form a colloid;
    (iv) ejecting the colloid through a nozzle to form droplets; and
    (v) causing or allowing the water-soluble polymer to gel or form a solid.
19. A steroid for use of any of clauses 1 to 15 wherein the steroid is comprised in a formulation obtainable by a process comprising:
    (a) dissolving in water a water-soluble polymer and dissolving or dispersing in the water a steroid to form a solution or dispersion;
    (b) ejecting the solution or dispersion through a nozzle to form droplets; and
    (c) causing or allowing the water-soluble polymer to gel or form a solid,
the process optionally further comprising between steps (a) and (b) a step (b1):
    (b1) mixing the solution or dispersion and a liquid which will mix with water to form a colloid, thereby to form a colloid.
20. A steroid for use of any preceding clause for use in combination therapy with one, two or three of active agents (a), (b) and (c) below:
    (a) an immunosuppressant;
    (b) a promoter of the expression or activity of HIF, for example a hydroxylase inhibitor;
    (c) another anti-fibrotic agent.
21. A steroid for use of any of clauses 1 to 19 for use in combination therapy with the following active agent(s):
    (i) cyclosporin A; or
    (ii) DMOG; or
    (iii) hydralazine; or
    (iv) cyclosporin A and DMOG; or
    (v) cyclosporin A and hydralazine.

22. A steroid for use of clause 20 or clause 21 wherein the steroid and the active agent or agents with which the steroid is for use in combination therapy are all comprised in a fixed combination.

23. A steroid for use of any preceding clause which is for use in treating a patient having at least one disease selected from an inflammatory bowel disease and an enteropathy.

24. A steroid for use of any preceding clause wherein the treatment is to inhibit, delay and/or reduce progression and/or initiation of intestinal fibrosis.

25. A method for treating intestinal fibrosis in a subject, comprising enterally administering a steroid to the subject.

26. A method of clause 25 wherein the steroid is administered orally.

27. A method of clause 25 or clause 26 wherein the steroid is selected from aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives, and combinations thereof.

28. A method of any of clauses 25 to 27 wherein the steroid is susceptible to first pass metabolism.

29. A method of clause 28 wherein the steroid is selected from budesonide, flunisolide, fluticasone proprionate, rimexolone, butixocort, tixocortol and beclomethasone and the salts, esters, conjugates and prodrugs thereof.

30. A method of clause 25 or clause 26 wherein the steroid is budesonide, or a prodrug, ester or conjugate thereof.

31. A method of any of clauses 25 to 30 wherein the steroid is dissolved in a liquid or in a wax which has a melting temperature of no more than 37° C.

32. A method of clause 31 wherein the liquid or wax comprises a macrogol ester.

33. A method of clause 32 wherein the macrogol ester is macrogol-15-hydroxystearate.

34. A method of clause 31 wherein the liquid comprises a medium chain triglyceride.

35. A method of any of clauses 25 to 34 wherein the steroid is comprised in an oral formulation adapted to release the steroid at least in the colon.

36. A method of any of clauses 25 to 35 wherein the steroid is comprised in an oral formulation adapted to release the steroid at least in the ileum.

37. A method of any of clauses 25 to 36 wherein the steroid is comprised in an oral formulation adapted to release the steroid at least in the duodenum.

38. A method of any of clauses 25 to 34 wherein the steroid is comprised in an immediate release formulation.

39. A method of any of clauses 25 to 34 wherein the steroid is in solution in a controlled release formulation.

40. A method of any of clauses 25 to 39 formulation is a multiple minibead formulation.

41. A method of clause 40 wherein the minibeads comprise a water soluble polymer matrix having dispersed therein the steroid.

42. A method of any of clauses 25 to 39 wherein the steroid is comprised in a formulation obtainable by a process comprising:
　(i) dissolving a water-soluble polymer in water to form an aqueous solution;
　(ii) dissolving or dispersing the steroid in a liquid which will mix with the water to form a colloid to form a steroid solution or dispersion;
　(iii) mixing the aqueous solution and the steroid solution or dispersion to form a colloid;
　(iv) ejecting the colloid through a nozzle to form droplets; and
　(v) causing or allowing the water-soluble polymer to gel or form a solid.

43. A method of any of clauses 25 to 39 wherein the steroid is comprised in a formulation obtainable by a process comprising:
　(a) dissolving in water a water-soluble polymer and dissolving or dispersing in the water a steroid to form a solution or dispersion;
　(b) ejecting the solution or dispersion through a nozzle to form droplets; and
　(c) causing or allowing the water-soluble polymer to gel or form a solid,
the process optionally further comprising between steps (a) and (b) a step (b1):
　(b1) mixing the solution or dispersion and a liquid which will mix with water to form a colloid, thereby to form a colloid.

44. A method of clause 42 or clause 43 which further comprises drying the solid.

45. A method of any of clauses 25 to 44 which further comprises administering to the subject one, two or three of active agents (a), (b) and (c) below:
　(a) an immunosuppressant;
　(b) a promoter of the expression or activity of HIF, for example a hydroxylase inhibitor;
　(c) another anti-fibrotic agent.

46. A method of any of clauses 25 to 44 which further comprises administering to the subject the following active agent(s):
　(i) cyclosporin A; or
　(ii) DMOG; or
　(iii) hydralazine; or
　(iv) cyclosporin A and DMOG; or
　(v) cyclosporin A and hydralazine.

47. A method of clause 45 or clause 46 wherein the steroid and the further active agent or agents are all comprised in a fixed combination.

48. A method of clause 45 or clause 46 wherein the steroid and the further active agent or agents are administered simultaneously, separately or sequentially.

49. A method of any of clauses 25 to 48 wherein the subject has at least one disease selected from an inflammatory bowel disease and an enteropathy, and combinations thereof.

50. A method of any of clauses 25 to 49 wherein the treatment is to inhibit, delay and/or reduce progression and/or initiation of intestinal fibrosis.

EXAMPLES

Example 1—Manufacturing of Budesonide Minibeads Containing Kolliphor HS15

Preparation of the Dispersed Phase

Budesonide is dissolved in Kolliphor HS 15 under constant stirring at a concentration ranging from 1.19 to 1.88% w/w until a clear solution is obtained. The temperature is kept at 40° C. to maintain Solutol HS 15 liquid.

Preparation of the Aqueous Phase

The components of the aqueous phase are added to water, which is then heated up to 60-70° C. The aqueous phase is stirred constantly until all components are dissolved.

Mixing of the Two Phases

The dispersed phase and the aqueous phase are mixed at a 1:7 or 1:12 w/w ratio. The resulting mixture is stirred at 60-70° C. to achieve homogeneity. The homogeneous solution was ejected through a pipette, having a single orifice, to form droplets which fall into a cooling oil medium (a capric/caprylic triglyceride marketed as Miglyol 810N) at 8-10° C.

After approximately 30 minutes within the cooling oil medium, beads are recovered, centrifuged to eliminate excess oil and then dried at room temperature. Examples of beads obtained by this method are now given.

Budesonide Minibeads Containing Kolliphor HS15

Example 2

A summary of the formulations prepared is presented in Table 1 below:

TABLE 1

| Formulation | % Budesonide loaded | Dispersed phase Components | Aqueous phase Components | Dispersed phase to Aqueous phase ratio (w/w) | Test Performed |
|---|---|---|---|---|---|
| 1 | 0.5 | Solutol HS 15, | Gelatin, D-Sorbitol, SDS. | 1:12 | Content Assay (83.5%), Dissolution |
| 2 | 0.5 | Solutol HS 15, | Gelatin, D-Sorbitol, SDS, NaOH, HPMCP. | 1:12 | Content Assay (85.4%) |
| 3 | 0.5 | Solutol HS 15, | Gelatin, D-Sorbitol. | 1:12 | Content Assay (86.9%), in vivo study in fibrosis-induced mice |
| 4 | 0.5 | Solutol HS 15, | Gelatin, Glycerin | 1:12 | Content Assay (77.8%) |
| 5 | 0.5 | Solutol HS 15, | Gelatin, D-Sorbitol, NaOH, HPMCP. | 1:12 | Content Assay (87.6%) |
| 6 | 0.5 | Solutol HS 15, | Gelatin, D-Sorbitol. | 1:7 | Content Assay (84.4%) |

Example 3

The weight percentage amounts of the dry materials introduced into the process to form the minibeads of Table 1, Formulation 1 are indicated the table below.

| Composition | % w/w |
|---|---|
| Budesonide | 0.5 |
| D-Sorbitol | 5.8 |
| SDS | 4.1 |
| Gelatin | 60.5 |
| Solutol HS 15 | 29.1 |

These minibeads were submitted to an in vitro dissolution test performed in distilled water containing 0.2% w/v SDS. The percent release of budesonide over time for the dissolution test are shown in Table 2 below.

TABLE 2

| Timepoint (min) | % Budesonide released |
|---|---|
| 30 | 72.8 |
| 60 | 83.4 |
| 80 | 84.6 |
| 100 | 84.8 |
| 150 | 85.1 |

Example 4

The weight percentage amounts of the dry materials introduced into the process to form the minibeads of Table 1, Formulation 2 are indicated in the table below.

| Composition (dry basis) | % w/w |
|---|---|
| Budesonide | 0.5 |
| NaOH | 1.0 |
| HPMCP | 9.9 |
| D-Sorbitol | 5.2 |
| SDS | 3.9 |
| Gelatin | 53.4 |
| Solutol HS 15 | 26.2 |

Example 5

The weight percentage amounts of the dry materials introduced into the process to form the minibeads of Table 1, Formulation 3 are indicated in the table below. These beads are uncoated.

| Composition (dry basis) | % w/w |
| --- | --- |
| Budesonide | 0.50 |
| D-Sorbitol | 5.4 |
| Gelatin | 63.4 |
| Solutol HS 15 | 30.8 |

Example 6

The beads of Example 5 were coated with Surelease™ and pectin (98:2 ratio Surelease:pectin) to have the following weight percentage amounts of the dry materials.

| Composition (dry basis) | % w/w |
| --- | --- |
| Budesonide | 0.5 |
| D-Sorbitol | 5.0 |
| Gelatin | 58.3 |
| Solutol HS 15 | 28.3 |
| Surelease | 7.8 |
| Pectin | 0.2 |

The coated beads of Example 6 were used in the mouse model of fibrosis of Example 12.

Example 7

The weight percentage amounts of the dry materials introduced into the process to form the minibeads of Table 1, Formulation 4 are indicated in the table below.

| Composition (dry basis) | % w/w |
| --- | --- |
| Budesonide | 0.5 |
| Glycerin | 5.5 |
| Gelatin | 63.6 |
| Solutol HS 15 | 30.3 |

Example 8

The weight percentage amounts of the dry materials introduced into the process to form the minibeads of Table 1, Formulation 5 are indicated in the table below.

| Composition (dry basis) | % w/w |
| --- | --- |
| Budesonide | 0.5 |
| NaOH | 1.1 |
| HPMCP | 10.2 |
| D-Sorbitol | 5.2 |
| Gelatin | 56.1 |
| Solutol HS 15 | 26.9 |

Example 9

The weight percentage amounts of the dry materials introduced into the process to form the minibeads of Table 1, Formulation 6 are indicated in the table below.

| Composition (dry basis) | % w/w |
| --- | --- |
| Budesonide | 0.5 |
| D-Sorbitol | 4.4 |
| Gelatin | 52.1 |
| Solutol HS 15 | 42.9 |

Example 10

The weight percentage amounts of the dry materials introduced into the process to form the minibeads of Formulation 7 are indicated in the table below.

| Composition (dry basis) | % w/w |
| --- | --- |
| Budesonide | 0.5 |
| D-Sorbitol | 5.9 |
| SDS | 4.1 |
| Gelatin | 60.4 |
| Solutol HS 15 | 29.1 |

Budesonide Minibeads without Kolliphor HS 15

Example 11

The minibeads of Example 11 were prepared according to the method of Example 1 except the aqueous phase contained gelatin, D-Sorbitol and SDS and the dispersed phase contained budesonide, Transcutol P, Miglyol 810N and Cremophor EL.

The weight percentage amounts of the dry materials introduced into the process to form the minibeads of Example 11 are indicated in the table below.

| Composition (dry basis) | % w/w |
| --- | --- |
| Budesonide | 0.5 |
| D-Sorbitol | 5.9 |
| SDS | 4.2 |
| Gelatin | 60.3 |
| Transcutol P | 16.1 |
| Miglyol 810N | 4.4 |
| Cremophor EL | 8.8 |

Example 12—Mouse Model of Fibrosis

The effectiveness of minicapsules of Example 6 on controlling clinical manifestations of fibrosis was investigated using a mouse model of colitis.

The animal model uses dextran sodium sulphate (DSS) to induce inflammation of the colon, followed by a recovery phase to allow the development of fibrosis. The DSS induced model for studying fibrosis is reported in "Analysis of intestinal fibrosis in chronic colitis in mice induced by dextran sulfate sodium" (Kenji Suzuki et al *Pathology International* 2011; 61: 228-238). C57/B16 female mice (10-12 weeks old) were used in the study. There were 4 test groups of mice:

Healthy control—mice in this group were not administered with DSS or budesonide minispheres;

DSS no recovery—mice in this group were administered with 2.5% DSS in drinking water for 5 days and sacrificed at the end of DSS dosing (Day 5);

DSS recovery—mice in this group were administered with 2.5% DSS in drinking water for 5 days and allowed to recover naturally without receiving any budesonide;

DSS recovery Bud—mice in this group were administered with 2.5% DSS in drinking water for 5 days and allowed to recover with treatment with 2 minispheres of Example 6. The 2 minispheres were administered orally using a stainless steel oral gavage needle along with 0.1 ml saline using standard 1 ml syringe.

The weight change of each test group was recorded throughout the experiment. FIG. 1 shows the weight change of each test group as a percentage of their original weight. It can be seen from FIG. 1 that all three test groups given DSS rapidly lost weight with all three groups experiencing a very similar weight change when the DSS administration was stopped at day 5. After DSS administration was stopped and budesonide minicapsules were administered there was a nearly immediate improvement in the weight of the test group given budesonide (DSS 2.5% recovery Bud). In contrast the test group allowed to recover naturally (DSS 2.5% recovery) had a delayed recovery and continued to lose weight after the DSS had stopped being administered. Furthermore, the test group given budesonide (DSS 2.5% recovery Bud) recovered to a higher percentage of their original weight compared to the natural recovery group (DSS 2.5% recovery).

To measure induction of inflammation and to monitor disease progression, the disease activity index (DAI) is determined. The DAI is calculated as the sum of scores of weight loss, stool consistency and blood in faeces. Scoring of the disease activity index is shown in Table 3.

Normal stool=formed pellets loose stool=pasty and semiformed stool which do not stick to the anus diarrhoea=liquid stools that stick to the anus.

TABLE 3

| Score | Weight loss | Stool consistency | Blood in feces |
|---|---|---|---|
| 0 | None | Normal | None |
| 1 | 1-5% | | |
| 2 | 5-10% | Loose | Hemoccult+ |
| 3 | 10-20% | | |
| 4 | >20% | Diarrhoea | Gross bleeding |

Figure 2:
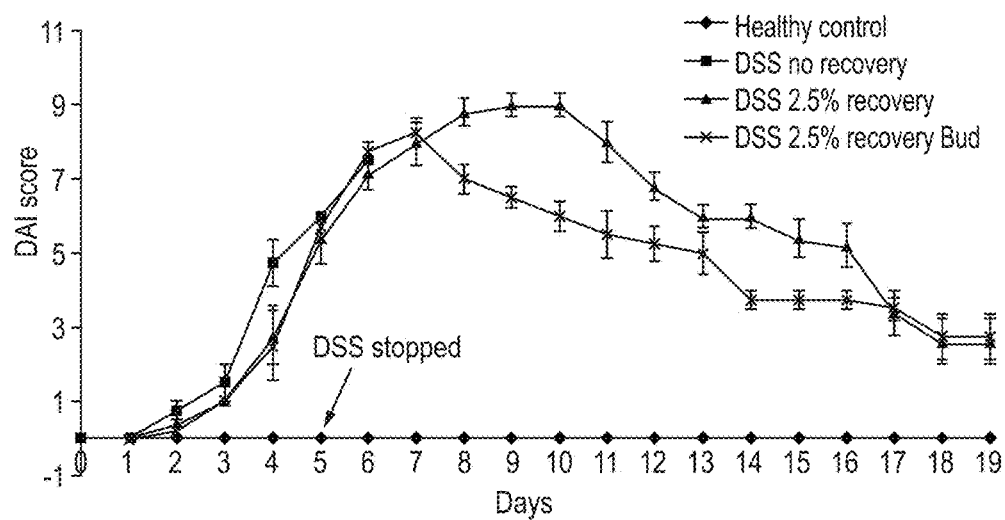
FIG. 2 is a plot of Disease Activity Index (DAI) showing the effect of a budesonide formulation of the invention (DSS recovery—Bud), see Example 12.

A graph of the DAI values the 4 test groups for the duration of the experiment is shown in FIG. 2. It can be seen from FIG. 2 that the three test groups that were administered with DSS had progressively worse DAI scores as the DSS administration continued. As in the weight change graph of FIG. 1 where the weight change was similar when DSS administration was stopped, the DAI values were very similar in all three test groups when DSS administration was stopped. A much quicker reduction in the DAI score was observed for mice treated with budesonide, the DSS 2.5% recovery—Bud group, compared with mice in the natural recovery group (DSS 2.5% recovery).

The weight change data and disease activity data shown in FIGS. 1 and 2 shows that DSS causes a negative effect on the tested mice which is more rapidly counteracted when the mouse is administered with budesonide, as opposed to allowing natural recovery.

At the end of the experiment, the mice were euthanized by standard cervical dislocation. The following examinations of the colon were carried out:

Colon weight—the colon is emptied of the fecal matter and weight of each colon was recorded;

Colon length—the length of each colon was recorded; and

Colon histology—approximately 10 mm of mid-colon is fixed in 10% buffered formaline and paraffin embedded. 4 µm sections were stained with Hematoxyline and Eosin stain to determine the degree of inflammation and Masson trichrome stain for evaluation of fibrosis by measurement of Collagen III. The stained sections were examined under light microscopy.

Figure 3:
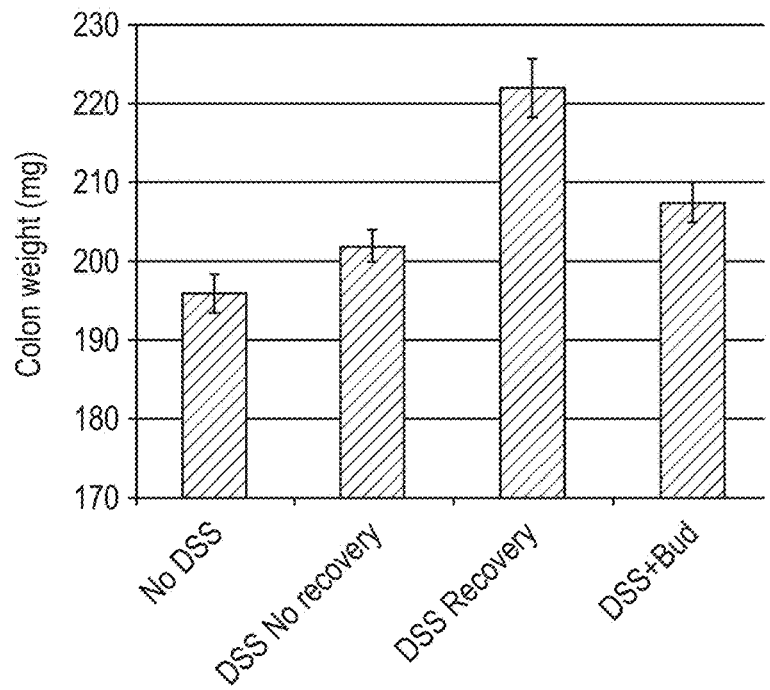
FIG. 3 is a bar chart showing colon weight (mg) from the four mouse groups in the DSS model of fibrosis, see Example 12.

Colon weight is an indicator of colon health. A healthy colon will weigh less than an unhealthy colon which has become inflamed and fibrotic. The results of the analysis of colon weight of the test groups are shown in FIG. 3. The colon weight in mg is shown for each test group.

Figure 4:
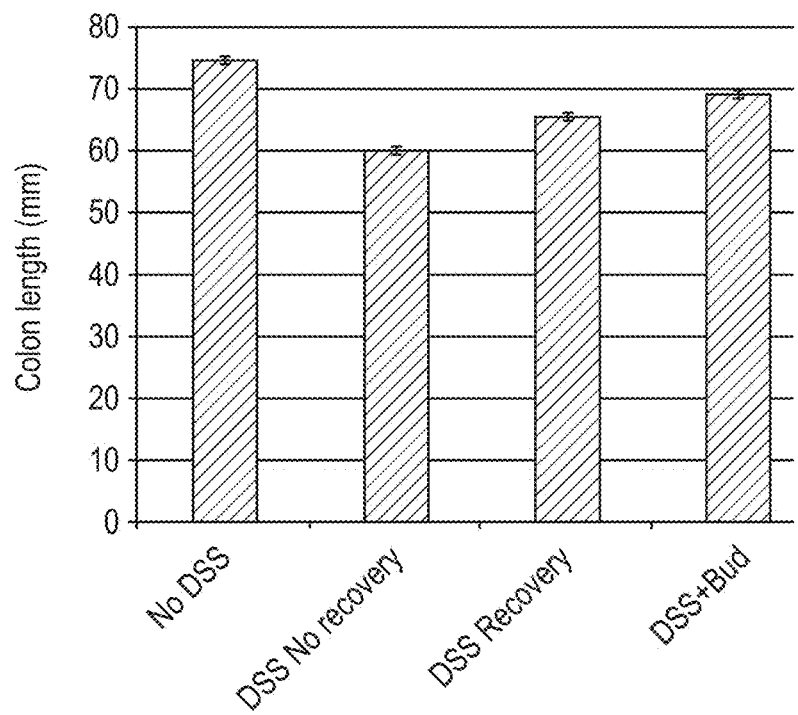
FIG. 4 is a bar chart showing colon length (mm) from the four mouse groups in the DSS model of fibrosis, see Example 12.

Colon length is also an indicator of colon health. A healthy colon is longer than an unhealthy colon, as is evident by comparing the colon length of the No DSS group against the colon length of the three groups administered with DSS in FIG. 4. The colon weight and colon length results also suggest that treatment with budesonide is effective in the 14 day recovery period.

Figure 5:
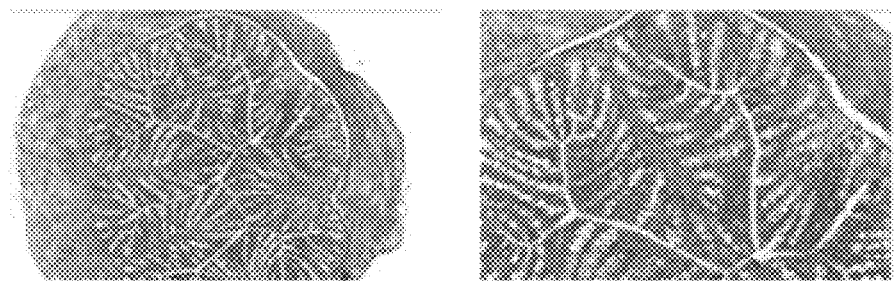
FIG. 5 is histology images of colonic tissue of healthy control specimens in the DSS model of fibrosis, see Example 12.
Figure 6:
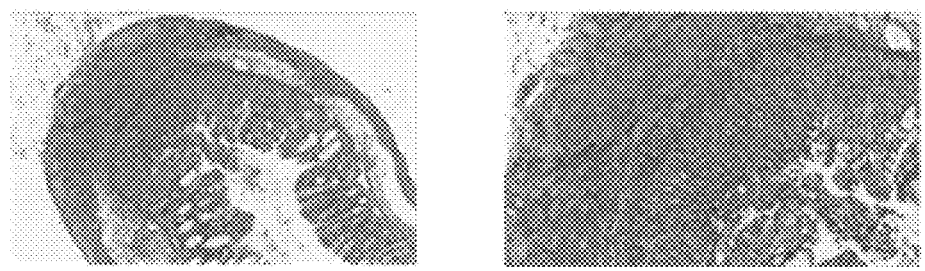
FIG. 6 is histology images of colonic tissue of DSS no recovery specimens in the DSS model of fibrosis, see Example 12.
Figure 7:
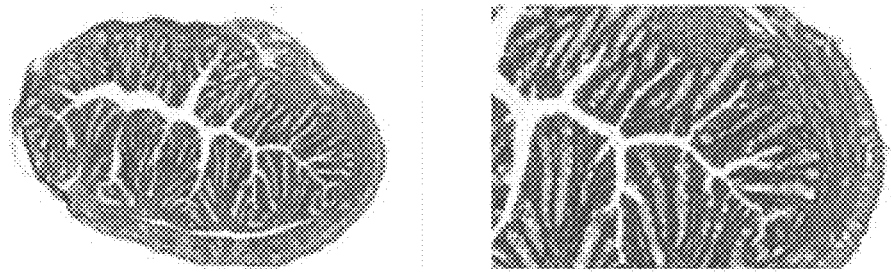
FIG. 7 is histology images of colonic tissue of DSS recovery (natural recovery) specimens after 14 days of recovery in the DSS model of fibrosis, see Example 12.
Figure 8:
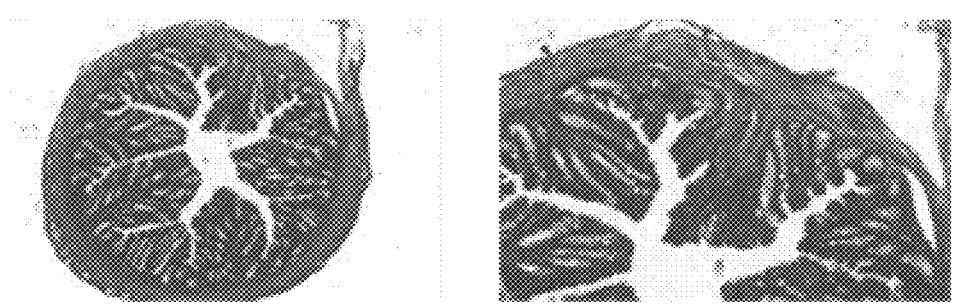
FIG. 8 is histology images of colonic tissue of DSS recovery—Bud (recovery with treatment with budesonide) specimens after 14 days of recovery in the DSS model of fibrosis, see Example 12.

FIGS. 5 to 8 show colon histology of each test group stained with Hematoxyline and Eosin. The colon histology of the healthy control specimens show a healthy colon (FIG. 5). In contrast, the mice that were euthanised at Day 5 and did not have any recovery time (DSS 2.5% noo recovery) show a damaged colon with a thickened submucosa and irregular epithelial structure (FIG. 6). The two test groups that were allowed to recover for 14 days, DSS 2.5% recovery (FIG. 7) and DSS 2.5% recovery—Bud (FIG. 8), displayed improved colonic health with a reduction in the colonic wall thickness and an ordered mucosa. (Note that the term "Bud" refers to budesonide). The histology of colonic tissues suggests that treatment with budesonide is effective at treating fibrosis in the 14 day recovery period.

Figure 9:
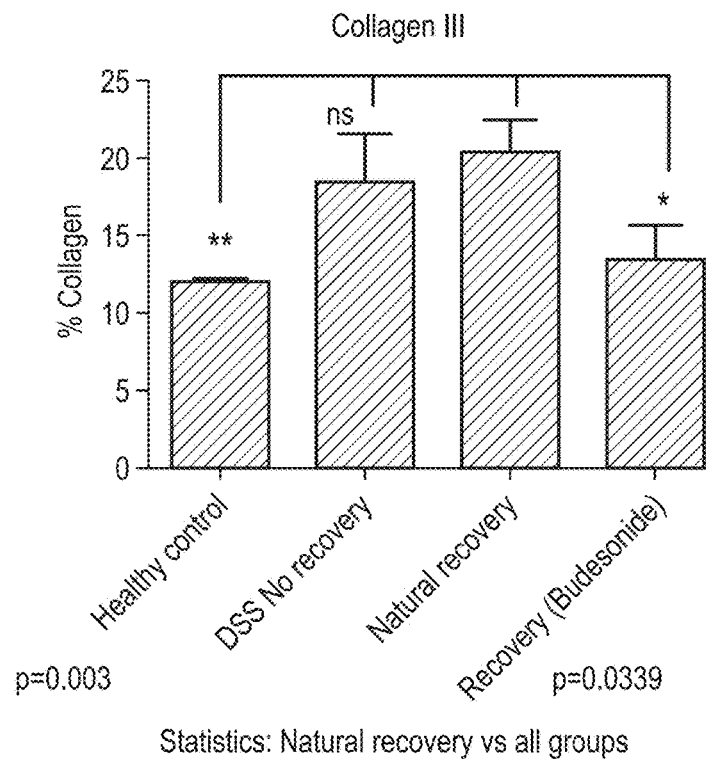
FIG. 9 is a bar chart showing the % Collagen III identified from colonic histology samples of each of the four mouse groups in the DSS fibrosis model, see Example 12.

FIG. 9 indicates the amount of collagen type III in the histological samples. Collagen type III level is an important indicator in the fibrosis model. Data from a study on collagen type III synthesis by fibroblasts isolated from patients' strictures resulting from Crohn's disease provides evidence that the different reactivity of mesenchymal cells to cytokines in terms of synthesizing type III collagen fibrils, which is a major component of collagen fibrils, may play an important role in the pathogenesis of fibrosis and stricture formation in chronic inflammatory bowel diseases.

The levels of collagen III in the group treated with budesonide are lower than the collagen III levels in the natural recovery group (DSS recovery) with statistical significance (unpaired t-test, one-tailed—95% confidence interval). The collagen levels are also statistically significantly lower for the healthy control and DSS no recovery groups compared to the DSS recovery group.

The above result shows that there is a statistically significant difference when comparing the collagen type III level in a budesonide treated group with the DSS recovery group. Therefore, the conclusion that budesonide has a beneficial effect against fibrosis can be drawn.

Example 13—Preparation of Budesonide and Cyclosporin a Minicapsules

The minibeads of Example 13 were prepared according to the method of Example 1 except the aqueous phase contained gelatin, D-Sorbitol and SDS and the dispersed phase contained budesonide, cyclosporin A, Transcutol P, Miglyol 810N and Cremophor EL.

The weight percentage amounts of the dry materials introduced into the process to form the minibeads of Example 13 are indicated in the table below.

| Composition (dry basis) | % w/w |
|---|---|
| Cyclosporine | 10.1 |
| Budesonide | 0.8 |
| Transcutol P | 16.6 |
| Cremophor EL | 9.3 |
| Miglyol 810 N | 4.6 |
| Gelatin | 48.7 |
| D-Sorbitol | 5.7 |
| SDS | 4.3 |

Example 14

The minicapsules of Example 13 were coated with 5.9% weight gain of a Surelease/pectin mixture (98:2 ratio of Surelease:pectin) to give a weight percentage amount of the dry materials as shown in the table below.

| Composition (dry basis) | % w/w |
|---|---|
| Cyclosporine | 9.5 |
| Budesonide | 0.7 |
| Transcutol P | 15.7 |
| Cremophor EL | 8.8 |
| Miglyol 810 N | 4.3 |
| Gelatin | 46.0 |
| D-Sorbitol | 5.4 |
| SDS | 4.0 |
| Surelease | 5.5 |
| Pectin | 0.1 |

Example 15—Preparation of Budesonide and Hydralazine Minicapsules

The minibeads of Example 15 were prepared according to the method of Example 1 except the aqueous phase contained hydralazine, gelatin, D-Sorbitol and SDS and the dispersed phase contained budesonide, Transcutol P, Miglyol 810N and Cremophor EL.

The weight percentage amounts of the dry materials introduced into the process to form the minibeads of Example 13 are indicated in the table below.

| Composition (dry basis) | % w/w |
|---|---|
| Hydralazine | 10.2 |
| Budesonide | 0.8 |
| Transcutol P | 16.8 |
| Miglyol 810N | 4.7 |
| Cremophor EL | 9.2 |
| Gelatin | 49.5 |
| D-Sorbitol | 5.0 |
| SDS | 3.8 |

Example 16

The minicapsules of Example 15 were coated with 5.1% weight gain of a Surelease/pectin (98:2 ratio of Surelease:pectin) mixture to give a weight percentage amount of the dry materials as shown in the table below.

| Composition (dry basis) | % w/w |
|---|---|
| Hydralazine | 9.7 |
| Budesonide | 0.8 |
| Transcutol P | 16.0 |
| Miglyol 810N | 4.5 |
| Cremophor EL | 8.7 |
| Gelatin | 47.1 |
| D-Sorbitol | 4.8 |
| SDS | 3.6 |
| Surelease | 4.8 |
| Pectin | 0.1 |

Example 17—Mouse Model of Fibrosis

The coated budesonide and cyclosporin A minicapsules of Example 14 and the budesonide and hydralazine minicapsules of Example 16 were investigated for effectiveness in controlling clinical manifestations of intestinal fibrosis using a mouse model of colitis.

The animal model was the same as the model used in Example 12 using dextran sodium sulphate (DSS) to induce inflammation of the colon, followed by a recovery phase to allow the development of fibrosis. C57/B16 female mice (10-12 weeks old) were used in the study. There were 4 test groups of mice:

Healthy control—mice in this group were not administered with DSS or budesonide minispheres;

DSS no recovery—mice in this group were administered with 2.5% DSS in drinking water for 5 days and sacrificed at the end of DSS dosing (Day 5);

DSS recovery—mice in this group were administered with 2.5% DSS in drinking water for 5 days and allowed to recover naturally without receiving any budesonide; and DSS recovery with administration of a test formulation—mice in this group were administered with 2.5% DSS in drinking water for 5 days and allowed to recover with treatment with 2 minispheres of a test formulation. The 2 minispheres were administered orally using a stainless steel oral gavage needle along with 0.1 ml saline using standard 1 ml syringe.

There were four test formulations that were administered to mice. The four test formulations are given below:

DSS recovery—Bud+CyA (uncoated)—minicapsules of Example 13;

DSS recovery—Bud+CyA (coated)—minicapsules of Example 14;

DSS recovery—Bud+HyA (uncoated)—minicapsules of Example 15; and

DSS recovery—Bud+HyA (coated)—minicapsules of Example 16.

Each of the four test formulations was compared to the healthy control, DSS no recovery and the DSS recovery test groups for DAI scores, colon histology, submucosal collagen type I levels and submucosal collagen type III levels.

To measure induction of inflammation and to monitor disease progression, the disease activity index (DAI) was determined, as explained above for Example 12.

A graph of the DAI values of each of the four test formulations correlated against the healthy control, DSS no recovery and the DSS recovery test groups for the duration of the experiment is shown in FIGS. 10 to 13.

Figure 10:
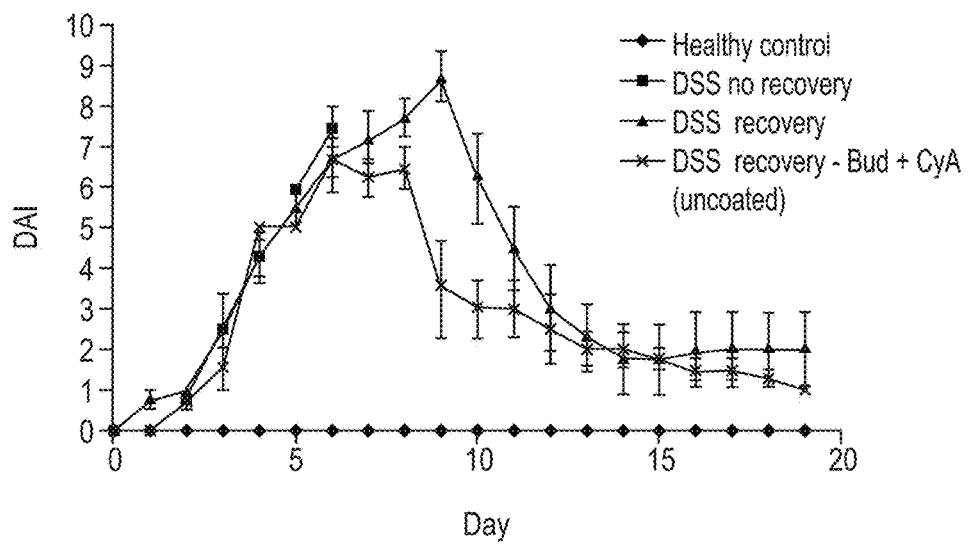
FIG. 10 is a plot of Disease Activity Index (DAI) showing the effect of a budesonide-cyclosporin combination formulation of the invention (DSS recovery—Bud+CyA (uncoated)), see Example 17.
Figure 11:
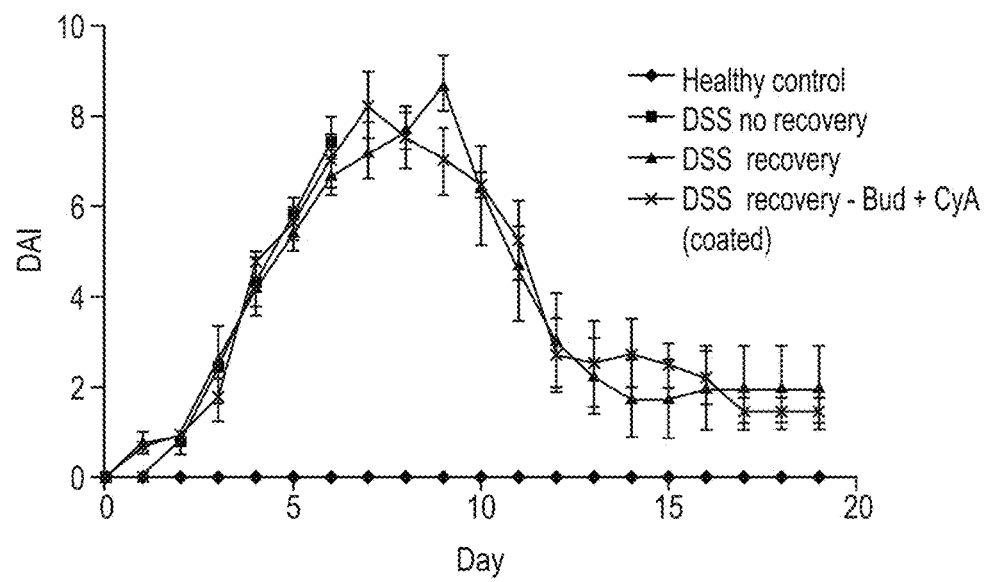
FIG. 11 is a plot of Disease Activity Index (DAI) graph showing the effect of a budesonide-cyclosporin combination formulation of the invention (DSS recovery—Bud+CyA (coated)), see Example 17.

FIG. 10 shows the DAI scores of the test formulation containing a combination of budesonide and cyclosporin in uncoated minicapsules (Example 13). When administration of DSS is stopped and administration of the test formulation starts there is a rapid reduction in the DAI score, whereas a delayed reduction of the DAI was seen in the natural recovery test group. The same minicapsules coated with Surelease/pectin (Example 14) produced a similar reduction in the DAI to the natural recovery test group (FIG. 11). However, the final DAI score for the DSS recovery—Bud+CyA (coated) test group was lower than the natural recovery group.

Figure 12:
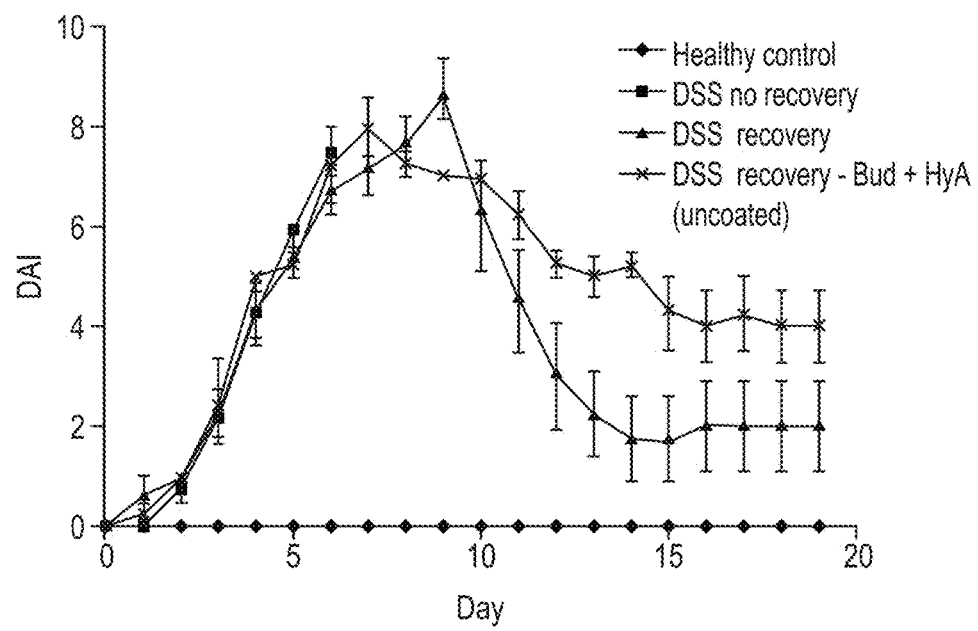
FIG. 12 is a plot of Disease Activity Index (DAI) graph showing the effect of a budesonide-hydralazine combination formulation of the invention (DSS recovery—Bud+HyA (uncoated)), see Example 17.
Figure 13:
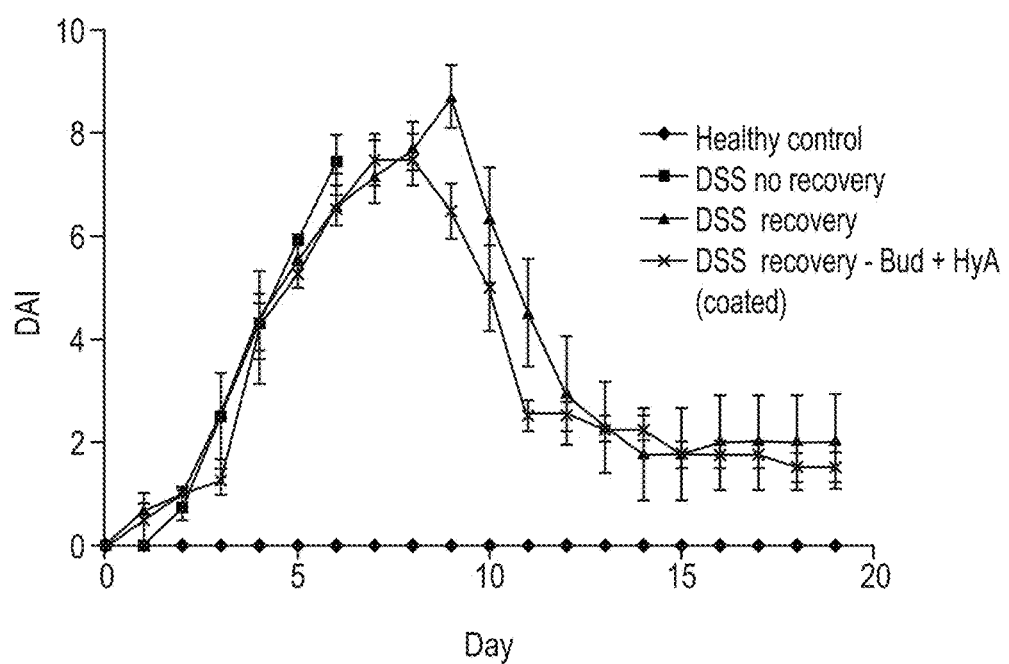
FIG. 13 is a plot of Disease Activity Index (DAI) graph showing the effect of a budesonide-hydralazine combination formulation of the invention (DSS recovery—Bud+HyA (coated)), see Example 17.

FIG. 12 and FIG. 13 show plots of the DAI scores for the DSS recovery—Bud+HyA (uncoated) and DSS recovery—Bud+HyA (coated) test formulation respectively. The coated budesonide and hydralazine test formulation (Example 16) showed improved DAI scores over the natural recovery test group.

At the end of the experiment, the mice were euthanized by standard cervical dislocation and examinations of the colon histology were carried out. Approximately 10 mm of mid-colon was fixed in 10% buffered formaline and paraffin embedded. 4 µm sections were stained with Masson trichrome stain for evaluation of fibrosis by measurement of submucosal collagen I and submucosal collagen III. The stained sections were examined under light microscopy.

Figure 14:
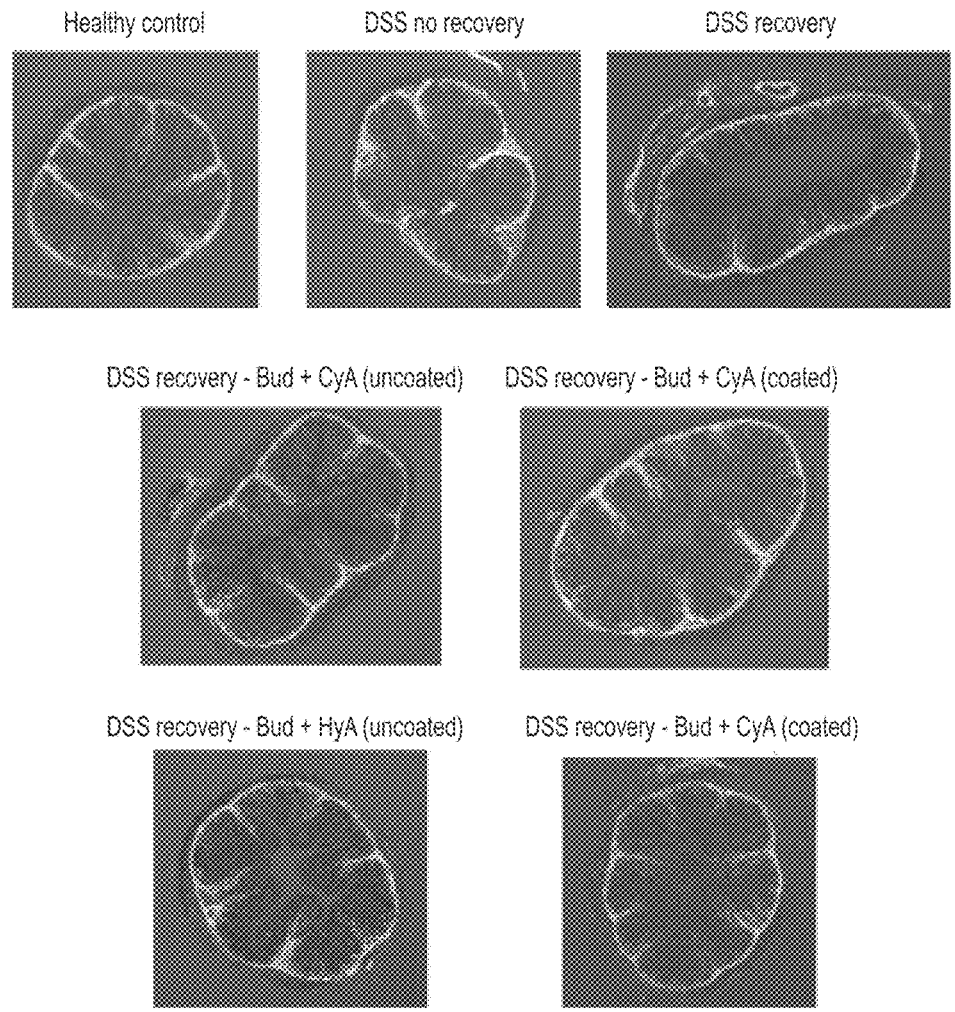
FIG. 14 shows images of histology of colonic tissue stained with Masson trichrome showing the incidence of collagen, see Example 17.

FIG. 14 shows colon histology of each test group stained with Masson trichrome. This stain colors collagen and gives different types of collagen different colours. In this experiment collagen type I and type II were of interest and these two types of collagen are stained red and green respectively. The colon histology of the healthy control specimens show a healthy colon with submucosal collagen. In contrast, the mice that were euthanised at Day 5 and did not have any recovery time (DSS 2.5% no recovery) show a distended submucosal layer with prolific levels of collagen. The test group that was allowed to recover naturally for 14 days displays improved colonic health with a thinner submucosal layer. The histology of the colon of mice in the test groups that received one of the test formulations also showed an improvement in colonic health with a noticeably thinner submucosa.

Figure 15:
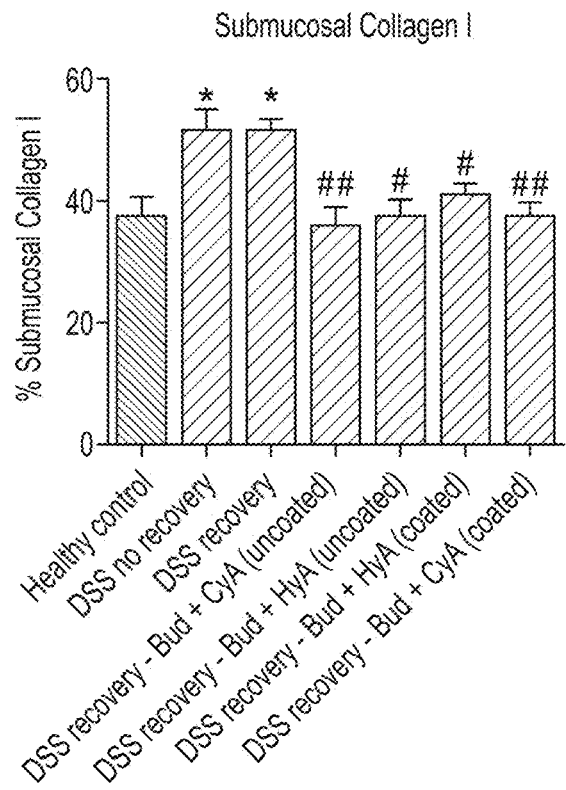
FIG. 15 is a bar chart showing the % submucosal collagen I in colonic histology samples of the test groups of Example 17.
Figure 16:
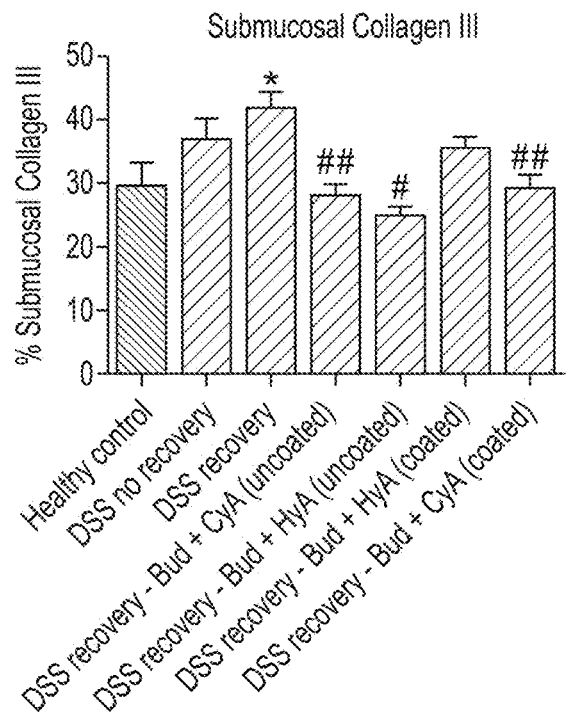
FIG. 16 is a bar chart showing the % submucosal collagen III in colonic histology samples of the test groups of Example 17.

The colon histology was then examined under light microscopy and the levels of collagen type I and type II were quantified to give the bar charts in FIGS. 15 and 16. FIG. 15 shows the levels of collagen type I for each of the test groups and each of the test formulations. It is immediately apparent from this data that collagen I levels in the test groups given one of the test formulations are comparable with the collagen levels in the healthy control. In contrast, the test groups that were not allowed to recovery and the test group that recovered naturally have a higher level of collagen I than the healthy control and the test groups given one of the four test formulations. Interestingly, the healthy recovery test group has virtually the same level of collagen I as the test group that was not allowed to recover. This implies that collagen levels are not reduced when recovery is allowed to progress naturally, although the test group showed an improvement in DAI; therefore, fibrosis is not affected by natural recovery. However, each of the test formulations reduced the collagen I levels to a comparable level to the healthy control.

This clearly shows that the test formulations are effective at reducing collagen I levels which have been raised by inflammation and the test formulation are effective treatments of fibrosis.

FIG. 16 shows the levels of collagen type III for each of the test groups and each of the test formulations. As in the results for collagen I, in the test group that was not allowed to recover (DSS no recovery) and the test group allowed to recover naturally (DSS recovery) the level of collagen III increased compared to the healthy control. Interestingly, in this case the DSS recovery group had higher levels of collagen III than the DSS no recovery group. This implies that collagen III synthesis may continue after the DSS administration is stopped, and the source of inflammation is removed. It can be concluded that allowing recovery to occur naturally does not have any beneficial effect on the level of collagen II and hence fibrosis. In contrast to the DSS recovery group and relative thereto, the test groups given one of the four test formulations showed a reduced level of collagen III. The test groups treatment with uncoated budesonide+cyclosporin, Example 13, coated budesonide+cyclosporin, Example 14, and uncoated budesonide+hydralazine, Example 15, gave a level of collagen III comparable to the healthy control.

In the same way that the collagen I data does; this data clearly shows that the test formulations are effective at reducing collagen III levels, especially for the formulations of Examples 13-15, which have been raised by inflammation. Therefore, the test formulation are effective treatments of fibrosis.

Suggest inclusion of other DSS data here. I believe that there is a strong enough correlation between short term DSS studies and the recovery model to support examples of other drugs with anti-fibrotic efficacy, assuming that fibrosis is a complication associated with inflammation, regardless of cause.

Example 17—Aspect Ratio

Minibeads were made generally following the procedure of Example 1 by extrusion from a nozzle to fall into a cooling medium. Some of the minibeads were then coated as described herein with a Surelease™ and pectin mixture. Sample populations of the coated minibeads and sample populations of uncoated minibeads were both typically found to have an average aspect ratio of 1.2 when measured using an Eyecon™ particle characteriser.

We claim:

1. A method for treating intestinal fibrosis in a subject, wherein the subject is medically considered to be suffering from intestinal fibrosis and from a condition selected from Crohn's disease, ulcerative colitis, gluten-sensitive enteropathy, a celiac disease, radiation enteropathy, graft-versus-host disease, collagenous colitis, eosinophilic enteropathy, drug-induced enteropathy, sigmoid diverticulitis, solitary rectal ulcer, cystic fibrosis, an intra-peritoneal fibrotic adhesion, desmoplastic reaction in a gastrointestinal tumors, a desmoid tumor, a gastrointestinal stromal tumor (GIST), a post-surgical intestinal adhesion, a post-surgical intestinal stricture, hemorrhagic enteropathy, protein-losing enteropathy, autoimmune enteropathy, colorectal carcinoma and adenocarcinoma, the method comprising enterally administering a steroid to the subject, wherein the steroid is selected from:
    (i) steroids susceptible to first pass metabolism,
    (ii) corticosteroids, and
    (iii) aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives, and combinations thereof.

2. A method of claim 1 wherein the subject is medically considered to be suffering from gluten-sensitive enteropathy.

3. A method of claim 1 wherein the subject is medically considered to be suffering from celiac disease.

4. A method of claim 1 wherein the steroid is susceptible to first pass metabolism.

5. A method of claim 1 wherein the steroid is budesonide, or a prodrug, ester or conjugate thereof.

6. A method of claim 1 wherein the steroid is exposed to the small intestine and/or the large intestine.

7. A method of claim 1 wherein the steroid is comprised in an oral formulation adapted to release the steroid at least in the colon.

8. A method of claim 1 wherein the steroid is comprised in an oral formulation adapted to release the steroid at least in the ileum.

9. A method of claim 1 wherein the steroid is comprised in a formulation obtainable by a process selected from processes (A) and (B):
   (A) a process comprising:
      (i) dissolving a water-soluble polymer in water to form an aqueous solution;
      (ii) dissolving or dispersing the steroid in a liquid to form a steroid solution or dispersion;
      (iii) mixing the aqueous solution and the steroid solution or dispersion to form a colloid;
      (iv) ejecting the colloid through a nozzle to form droplets; and
      (v) causing or allowing the water-soluble polymer to gel or form a solid,
   (B) a process comprising:
      (a) dissolving in water a water-soluble polymer and dissolving or dispersing in the water a steroid to form a solution or dispersion;
      (b) ejecting the solution or dispersion through a nozzle to form droplets; and
      (c) causing or allowing the water-soluble polymer to gel or form a solid, the process optionally further comprising between steps (a) and (b) a step (b1):
      (b1) mixing the solution or dispersion and a liquid thereby to form a colloid.

10. A method of claim 9 wherein the process further comprises drying the solid.

11. A method of claim 1 which further comprises administering to the subject the following active agent(s):
   (i) cyclosporin A; or
   (ii) dimethyloxalylglycine (DMOG); or
   (iii) hydralazine; or
   (iv) cyclosporin A and DMOG; or
   (v) cyclosporin A and hydralazine.

12. A method of claim 1 wherein the steroid is administered orally and is comprised in a multiple minibead formulation wherein the minibeads comprise a water soluble polymer matrix in which the steroid is distributed.

13. A method of claim 12 wherein the minibeads are seamless minibeads that comprise the water-soluble polymer matrix and, dispersed in the matrix, a disperse phase comprising materials selected from hydrophobic and amphiphilic materials, and combinations thereof, steroid being included in the disperse phase.

14. A method for maintaining, restoring or improving the gastrointestinal health of a subject who has displayed or is displaying a clinical or sub-clinical symptom of gastrointestinal fibrosis, comprising enterally administering a steroid to the subject, wherein the steroid is selected from:
   (i) steroids susceptible to first pass metabolism,
   (ii) corticosteroids, and
   (iii) aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives, and combinations thereof.

15. A method of claim 14 wherein the steroid is susceptible to first pass metabolism.

16. A method of claim 14 wherein the steroid is budesonide, or a prodrug, ester or conjugate thereof.

17. A method of claim 14 wherein the steroid is exposed to the small intestine and/or the large intestine.

18. A method of claim 14 wherein the steroid is comprised in an oral formulation adapted to release the steroid at least in the colon.

19. A method of claim 14 wherein the steroid is comprised in an oral formulation adapted to release the steroid at least in the ileum.

20. A method of claim 14 wherein the steroid is comprised in a formulation obtainable by a process selected from processes (A) and (B):
   (B) a process comprising:
      (vi) dissolving a water-soluble polymer in water to form an aqueous solution;
      (vii) dissolving or dispersing the steroid in a liquid to form a steroid solution or dispersion;
      (viii) mixing the aqueous solution and the steroid solution or dispersion to form a colloid;
      (ix) ejecting the colloid through a nozzle to form droplets; and
      (x) causing or allowing the water-soluble polymer to gel or form a solid, (B) a process comprising:
- (d) dissolving in water a water-soluble polymer and dissolving or dispersing in the water a steroid to form a solution or dispersion;
- (e) ejecting the solution or dispersion through a nozzle to form droplets; and
- (f) causing or allowing the water-soluble polymer to gel or form a solid, the process optionally further comprising between steps (a) and (b) a step (b1):
- (b1) mixing the solution or dispersion and a liquid thereby to form a colloid.

21. A method of claim 20 wherein the process further comprises drying the solid.

22. A method of claim 14 which further comprises administering to the subject the following active agent(s):
- (vi) cyclosporin A; or
- (vii) dimethyloxalylglycine (DMOG); or
- (viii) hydralazine; or
- (ix) cyclosporin A and DMOG; or
- (x) cyclosporin A and hydralazine.

23. A method of claim 14 wherein the steroid is administered orally and is comprised in a multiple minibead formulation wherein the minibeads comprise a water soluble polymer matrix in which the steroid is distributed.

24. A method of claim 23 wherein the minibeads are seamless minibeads that comprise the water-soluble polymer matrix and, dispersed in the matrix, a disperse phase comprising materials selected from hydrophobic and amphiphilic materials, and combinations thereof, steroid being included in the disperse phase.

25. A method of claim 14 wherein the gastrointestinal fibrosis is an intestinal fibrosis.

26. A method for arresting, reducing or delaying the development of a clinical or sub-clinical symptom of gastrointestinal fibrosis, wherein the subject is medically considered to be suffering from gastrointestinal fibrosis, comprising enterally administering a steroid to the subject, wherein the steroid is selected from:
- (i) steroids susceptible to first pass metabolism,
- (ii) corticosteroids, and
- (iii) aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives, and combinations thereof.

27. A method of claim 26, wherein arresting, reducing or delaying the development of a clinical or sub-clinical symptom is of a relapse of gastrointestinal fibrosis.

28. A method of claim 26 wherein the steroid is susceptible to first pass metabolism.

29. A method of claim 26 wherein the steroid is budesonide, or a prodrug, ester or conjugate thereof.

30. A method of claim 26 wherein the steroid is exposed to the small intestine and/or the large intestine.

31. A method of claim 26 wherein the steroid is comprised in an oral formulation adapted to release the steroid at least in the colon.

32. A method of claim 26 wherein the steroid is comprised in an oral formulation adapted to release the steroid at least in the ileum.

33. A method of claim 26 wherein the steroid is comprised in a formulation obtainable by a process selected from processes (A) and (B):
- (C) a process comprising:
  - (xi) dissolving a water-soluble polymer in water to form an aqueous solution;
  - (xii) dissolving or dispersing the steroid in a liquid to form a steroid solution or dispersion;
  - (xiii) mixing the aqueous solution and the steroid solution or dispersion to form a colloid;
  - (xiv) ejecting the colloid through a nozzle to form droplets; and
  - (xv) causing or allowing the water-soluble polymer to gel or form a solid,
- (B) a process comprising:
  - (g) dissolving in water a water-soluble polymer and dissolving or dispersing in the water a steroid to form a solution or dispersion;
  - (h) ejecting the solution or dispersion through a nozzle to form droplets; and
  - (i) causing or allowing the water-soluble polymer to gel or form a solid, the process optionally further comprising between steps (a) and (b) a step (b1):
  - (b1) mixing the solution or dispersion and a liquid thereby to form a colloid.

34. A method of claim 33 wherein the process further comprises drying the solid.

* * * * *